US009079950B2

(12) United States Patent
Drummer et al.

(10) Patent No.: US 9,079,950 B2
(45) Date of Patent: Jul. 14, 2015

(54) MODIFIED HEPATITIS C VIRUS PROTEINS

(75) Inventors: Heidi Drummer, Ascot Vale (AU);
Kathleen McCaffrey, Singapore (SG);
Pantelis Poumbourios, Ascot Vale (AU)

(73) Assignee: The Macfarlane Burnet Institute for Medical Research and Public Health Ltd, Melbourne (AU)

( * ) Notice: Subject to any disclaimer, the term of this patent is extended or adjusted under 35 U.S.C. 154(b) by 64 days.

(21) Appl. No.: 13/813,929

(22) PCT Filed: Aug. 4, 2011

(86) PCT No.: PCT/AU2011/000991
§ 371 (c)(1),
(2), (4) Date: Apr. 12, 2013

(87) PCT Pub. No.: WO2012/016290
PCT Pub. Date: Feb. 9, 2012

(65) Prior Publication Data
US 2013/0224246 A1      Aug. 29, 2013

(30) Foreign Application Priority Data

Aug. 4, 2010   (AU) ............................... 2010903478

(51) Int. Cl.
| C07K 14/18 | (2006.01) |
| G01N 33/569 | (2006.01) |
| A61K 39/12 | (2006.01) |
| C07K 16/10 | (2006.01) |
| C12N 7/00 | (2006.01) |
| C07K 14/005 | (2006.01) |

(52) U.S. Cl.
CPC ............ C07K 14/1833 (2013.01); A61K 39/12 (2013.01); C07K 14/005 (2013.01); C07K 16/109 (2013.01); C12N 7/00 (2013.01); G01N 33/56983 (2013.01); C07K 2317/76 (2013.01); C12N 2770/24222 (2013.01); C12N 2770/24261 (2013.01); C12N 2770/24262 (2013.01)

(58) Field of Classification Search
CPC .. A61K 39/12; C07K 14/005; C07K 14/1833; C07K 16/109; C07K 2317/76; C12N 7/00; C12N 2770/24261; C12N 2770/24262; C12N 2770/24222; G01N 33/56983
See application file for complete search history.

(56) References Cited

U.S. PATENT DOCUMENTS

| 5,227,487 A | 7/1993 | Haugland et al. ............... 546/15 |
| 5,274,113 A | 12/1993 | Kang et al. .................... 548/405 |
| 5,326,692 A | 7/1994 | Brinkley et al. .................. 435/6 |
| 5,405,975 A | 4/1995 | Kuhn et al. .................... 549/347 |
| 5,433,896 A | 7/1995 | Kang et al. .................... 252/700 |
| 5,442,045 A | 8/1995 | Haugland et al. ........... 530/391.3 |
| 5,451,663 A | 9/1995 | Kang et al. .................... 530/367 |
| 5,453,517 A | 9/1995 | Kuhn et al. .................... 549/227 |
| 5,459,276 A | 10/1995 | Kuhn et al. ....................... 33/52 |
| 5,516,864 A | 5/1996 | Kuhn et al. .................... 526/263 |
| 5,573,909 A | 11/1996 | Singer et al. ...................... 435/6 |
| 5,648,270 A | 7/1997 | Kuhn et al. ..................... 436/74 |
| 5,723,218 A | 3/1998 | Haugland et al. ............. 484/151 |
| 7,413,741 B2 | 8/2008 | Depraetere et al. ......... 424/184.1 |
| 8,535,686 B2 | 9/2013 | McCaffrey et al. ......... 424/228.1 |
| 2011/0014209 A1 | 1/2011 | McCaffrey .................. 424/161.1 |
| 2013/0323282 A1 | 12/2013 | Drummer et al. ........... 424/228.1 |
| 2014/0120127 A1 | 5/2014 | McCaffrey et al. ......... 424/228.1 |

FOREIGN PATENT DOCUMENTS

| WO | WO 93/06121 | 4/1993 |
| WO | WO 03/047617 | 6/2003 |
| WO | WO 2008/022401 | 2/2008 |
| WO | WO 2012/068637 | 5/2012 |

OTHER PUBLICATIONS

A model for the Hepatitis C Virus envelope glycoprotein E2. Proteins: Structure, Function, and Genetics 2000, vol. 40, pp. 355-366.*
Yagnik et al. A Model for the Hepatitis C Virus Envelope Glycoprotein E2. Proteins: Structure, Function and Genetics 2000, vol. 40, pp. 355-366.*
Letter/Written Disclosure of the Information Disclosure Statement, mailed May 2, 2013, U.S. Appl. No. 13/813,929, 2 pages.
International Search Report, issued Feb. 9, 2012, in connection with corresponding International Patent Application, PCT/AU2011/000991, 4 pages.
Written Opinion, issued Feb. 4, 2013, in connection with corresponding International Patent Application, PCT/AU2011/000991, 6 pages.
International Preliminary Report on Patentability, issued Feb. 5, 2013, in connection with corresponding International Patent Application, PCT/AU2011/000991, 7 pages.

(Continued)

*Primary Examiner* — Louise Humphrey
(74) *Attorney, Agent, or Firm* — McKenna Long & Aldridge LLP; Stephanie Seidman

(57) ABSTRACT

A composition comprising a hepatitis C virus (HCV) Envelope 2 (E2) polypeptide including a receptor binding variant, wherein the polypeptide is modified to comprise: (i) a cysteine mutated or disrupted at 2, 3, or 4 cysteines selected from C452, C486, C569, and C597; and wherein the polypeptide forms substantially fewer multimers by intermolecular disulfide bonding relative to the HCV E2 polypeptide without cysteine modification, and substantially retains CD81 binding; and various uses thereof. A method of producing a composition comprising at least 40%, or at least 45%, or at least 50%, or at least 55%, or at least 60%, or at least 65%, or at least 70% monomeric HCV E2 polypeptide, the method comprising expressing a polypeptide in a host cell and isolating the expressed product, wherein the polypeptide is an HCV E2 polypeptide including a receptor binding variant, and wherein the polypeptide is modified to comprise: (i) a cysteine mutated or disrupted at 2, 3, or 4 cysteines selected from C452, C486, C569, and C597.

26 Claims, 24 Drawing Sheets

(56) References Cited

OTHER PUBLICATIONS

Atherton and Sheppard, "Solid phase peptide synthesis: a practical approach," (the Practical Approach Series), Chapter 9, 107-123, (1989).
Ausubel et al., "Cross-reactivity of T-cell clones specific for altered peptide ligands of myelin basic protein," Cell Immunology 193(1): 99-107, (1999).
Ausubel et al., Current Protocols in Molecular Biology, John Wiley & Sons Inc., Unit 2.10.1 to 2.10.16, 16 pages, (1994-1998).
Ausubel et al., Current Protocols in Molecular Biology, John Wiley & Sons Inc., Unit 19.3, 29 pages (1994-1998).
Bandyopadhyay, P. and H. Temin, "Expression of complete chicken thymidine kinase gene inserted in a retrovirus vector," Mol Cell Biol 4(4): 749-754 (1984).
Berglund et al., "Semliki forest virus expression system: production of conditionally infectious recombinant particles," Biotechnology 11(8):916-920 (1993).
Berkner K., "Expression of heterologous sequences in adenovirus vectors," Curr Top Microbiol Immunol 158:39-66 (1992).
Bird et al., "Single-chain antigen-binding proteins," Science 242(4877):423-426 (1988).
Breakefield, X. and A. Geller, "Gene transfer into the nervous system," Mol Neurobiol 1(4):339-371 (1987).
Bressanelli et al., "Structure of a *Flavivirus* envelope glycoprotein in its low-pH-induced membrane fusion conformation," The EMBO J 23: 728-738 (2004).
Buchschacher, G. and A. Panganiban, "Human immunodeficiency virus vectors for inducible expression of foreign genes,"J. Virol. 66(5): 2731-2739 (1992).
Carter et al., "Humanized of an anti-p185HER2 antibody for human cancer therapy," Proc. Natl. Acad. Sci. USA 89(10): 4285-4289 (1992).
Carter et al., "High level *Escherichia coli* expression and production of a bivalent humanized antibody fragment," Biotechnology 10(2): 163-167 (1992).
Ciczora et al., "Contribution of the charged residues of hepatitis C virus glycoprotein E2 transmembrane domain to the functions of the E1E2 heterodimer," J. Gen Virol 86:2793-2798 (2005).
Ciczora et al., "Transmembrane domains of hepatitis C virus envelope glycoproteins: residues invovled in E1E2 heterodimerization and involvement of these domains in virus enry," J. Virol 81(5): 2372-2381 (2007).
Clackson et al., "Making antibody fragments using phage display libraries," Nature 352(6336):624-628 (1991).
Dayhoff et al., "A model of evolutionary change in proteins," in *Atlas of Protein Sequence and Structure*, vol. 5, Supp. 3, The National Biomedical Research Foundation, Silver Spring, MD, pp. 345-352 (1979).
Drummer, H. and P. Poumbourios, "Hepatitis C virus glycoprotein E2 contains a membrane-proximal heptad repeat sequence that is essential for E1E2 glycoprotein heterodimerization and viral entry," J. Biol. Chem. 279(29): 30066-30072 (2004).
Drummer et al., "Identification of the hepatitis C virus E2 glycoprotein binding site on the large extracellular loop of CD81," J. Virol. 76(21): 11143-11147 (2002).
Drummer et al., "A Conserved Gly436-Trp-Leu-Ala-Gly-Leu-Phe-Tyr motif in hepatitis C virus glycoprotein E2 is a determinant of CD81 binding and viral entry," J. Virol. 80(16):7844-7853 (2006).
Drummer et al., "Cell surface expression expression of functional hepatitis C virus E1 and E2 glycoproteins," FEBS Lett 546(2-3):385-390 (2003).
Drummer et al., "Determinants of CD81 dimerization and interaction with hepatitis C virus glycoprotein E2," Biochem Biophys Res Commun 328(1): 251-257 (2005).
Fenouillet et al., "Contribution of redox status to hepatitis C virus E2 envelope protein function and antigenicity," J. Biol. Chem. 283(39): 26340-26348 (2008).
Fink et al., "Gene transfer to neurons using herpes simplex virus-based vectors," Ann. Rev. Neurosci. 19:265-287 (1996).
Fink et al., "In vivo expression of beta-galactosidase in hippocampal neurons by HSV-mediated gene transfer," Hum Gene Ther 3(1):11-19 (1992).
Fraser et al., "Hepatitis C virus (HCV) envelope glycoproteins E1 and E2 contain reduced cysteine residues essential for virus entry," J. Biol. Chem. 286(37): 31984-31992 (2011).
Freese et al., "HSV-1 vector mediated neuronal gene delivery. Strategies for molecular neuroscience and neurology," Biochem Pharmacol 40(10):2189-2199 (1990).
Gonnet et al., "Exhaustive matching of the entire protein sequence database," Science 256(5062): 1443-1445 (1992).
Gorziglia, M. and A. Kapikian, "Expression of the OSU rotavirus outer capsid protein VP4 by an adenovirus recombinant," J. Virol. 66(7):4407-4412 (1992).
Harris et al., "Claudin association with CD81 defines hepatitis C virus entry," J. Biol. Chem. 285(27): 21092-21102 (2010).
Helseth et al., "Rapid complementation assays measuring replicative potential of human immunodeficiency virus type 1 envelope glycoproteins mutants," J. Virol. 64(5): 2416-2420 (1990).
Huston et al., "Protein engineering of antibody binding sites: recovery of specific activity in an anti-digoxin single-chain Fv analogue produced in *Escherichia coli*," Proc. Natl. Acad. Sci. USA 85(16): 5879-5883 (1988).
Johnson et al., "Cytotoxicity of a replication-defective mutant of herpes simplex virus type 1," J. Virol. 66(5): 2952-2965 (1992).
Jones et al., "Replacing the complementarity-determining regions in a human antibody with those from a mouse," Nature 321(6069): 522-525 (1986).
Keck et al., "Hepatitis C virus E2 has three immunogenic domains containing conformational epitopes with distinct properties and biological functions," J. Virol. 78(17): 9224-9232 (2004).
Keck et al., "Analysis of a highly flexible conformational immunogenic domain A in hepatitis C virus E2," J. Virol. 79(21): 13199-13208 (2005).
Kielian, M. and F. Rey, "Virus membrane-fusion proteins: more than one way to make a hairpin," Nat. Rev. Microbiol. 4(1): 67-76 (2006).
Kohler, G. and C. Milstein, "Continuous culture of fused cells secreting antibody of predefined specificity," Nature 256: 495-499 (1975).
Kortt et al., "Single-chain Fv fragments of anti-neuraminidase antibody NC10 containing five- and ten-residue linkers form dimers and with zero-residue linker a trimer," Protein Engineering 10(4): 423-433 (1997).
Kozak, M. and A. Shatkin, "Characterization of translational initiation regions from eukaryotic messenger RNAs," Methods Enzymol 60: 360-375 (1979).
Kozak M, "The Scanning model for translation: an update," J Cell Biol 108(2): 229-241 (1989).
Kozak M., "Determinants of translational fidelity and efficiency in vertebrate mRNAs," Biochimie 76(9): 815-821 (1994).
Kozak, M., "Interpreting cDNA sequences: some insights from studies on translation," Mamm Genome 7(8):563-574 (1996).
Krey et al., "The Disulfide bonds in glycoprotein E2 of hepatitis C virus reveal the tertiary organization of the molecule," PLoS Pathogens 6(2): e1000762, 11 pages (2010).
Kunkel T., "Rapid and efficient site-specific mutagenesis without phenotypic selection," Proc. Natl. Acad. Sci. 82:488-492 (1985).
Larrick et al., "Polymerase chain reaction using mixed primers: cloning of human monoclonal antibody variable region genes from single hybridoma cells," Biotechnology 7:934-938 (1989).
Liu et al., "Chimeric mouse-human IgG1 antibody that can mediate lysis of cancer cells," Proc. Natl. Acad. Sci. 84: 3439-3443 (1987).
Madzak et al., "Efficient in vivo encapsidation of a shuttle vector in pseudo-simian virus 40 virions using a shuttle virus as helper," J. Gen. Virol. 73: 1533-1536 (1992).
Mann, R. and D. Baltimore, "Varying the position of a retrovirus packaging sequence results in the encapsidation of both unspliced and spliced RNAs," J. Virol. 54(2):401-407 (1985).
Margolskee R., "Esptein-Barr virus based expression vectors," Curr Top Microbiol Immunol 158: 67-95 (1992).
Marks et al., "By-passing immunization. Human antibodies from V-gene libraries displayed on phage," J. Mol Biol 222(3): 581-597 (1991).

(56) References Cited

OTHER PUBLICATIONS

McCaffrey et al., "Expression and characterization of a minimal hepatitis C virus glycoprotein E2 core domain that retains CD81 binding," J Virol. 81:9584-9590 (2007).
Miller et al., "Design of retrovirus vectors for transfer and expression of the human beta-globin gene," J. Virol. 62(11):4337-4345 (1988).
Miller et al., "Generation of helper-free amphotropic retroviruses that transduce a dominant-acting, methotrexate-resistant dihydrofolate reductase gene," Mol Cell Biol 5(3):431-437 (1985).
Miller A., "Retroviral vectors," Curr Top Microbiol Immunol 158:1-24 (1992).
Morrison et al., "Chimeric human antibody molecules: mouse antigen-binding domains with human constant region domains," Proc. Natl. Acad. Sci. U.S.A. 81(21):6851-6855 (1984).
Moss B., "Genetically engineered poxviruses for recombinant gene expression, vaccination, and safety," Proc. Natl. Acad. Sci. USA 93:11341-11348 (1996).
Moss B., "Poxvirus expression vectors," Curr Top Microbiol Immunol 158:25-38 (1992).
Muzyczka N, "Use of adeno-associated virus as a general transduction vector for mammalian cells," Curr Top Microbiol Immunol 158:92-129 (1992).
Naldini et al., "In vivo gene delivery and stable transduction of nondividing cells by a lentiviral vector," Science 272(5259):263-267, (1996).
Ohi et al., "Construction and replication of an adeno-associated virus expression vector that contains human beta-globin cDNA," Gene 89(2):279-282 (1990).
Owisanka et al., "Identification of conserved residues in the E2 envelope glycoprotein of the hepatitis C virus that are critical for CD81 binding," J. Virol. 80(17):8695-8704 (2006).
Padlan, E., "A Possible procedure for reducing the immunogenicity of antibody variable domains while preserving their ligand-binding properties," Mol Immunol 28(4-5): 489-498 (1991).
Page et al., "Construction and use of a human immunodeficiency virus vector for analysis of virus infectivity," J. Virol 64(11): 5270-5276, (1990).
Patel et al., "Covalent interactions are not required to permit or stabilize the non-covalent association of hepatitis C virus glycoproteins E1 and E2," J. Gen. Virol. 80: 1681-1690 (1990).
Pedersen et al., "Comparison of surface accessible residues in human and murine immunoglobulin Fv domains. Implication for humanization of murine antibodies," J. Mol. Biol. 235(3): 959-973 (1994).
Petropoulos et al., "Using avian retroviral vectors for gene transfer," J. Virol. 66(6):3391-3397 (1992).
Presta et al., "Antibody engineering," Curr. Opin. Biotechnol. 3(4): 394-398 (1992).
Quantin et al., "Adenovirus as an expression vector in muscle cells in vivo," Proc. Natl. Acad. Sci. USA 89: 2581-2584 (1992).
Reichmann et al., "Reshaping human antibodies for therapy," Nature 332(6162):323-329 (1988).
Roberge et al., "A Strategy for a convergent synthesis of N-linked glycopeptides on a solid support," Science 269(5221): 202-204 (1995).
Roccasecca et al., "Binding of the hepatitis C virus E2 glycoprotein to CD81 is strain specific and is modulated by a complex interplay between hypervariable regions 1 and 2," J Virol 77(3):1856-1867 (2003).
Rosenfeld et al., "In vivo transfer of the human cystic fibrosis transmembrane conductance regulator gene to the airway epithelium," Cell 68(1):143-155 (1992).
Russell, D. and R. Hirata, "Human gene targeting by viral vectors," Nature Genetics 18:325-330 (1998).
Sambrook et al., Molecular Cloning: A Laboratory Manual, Cold Spring Harbor Laboratory, Cold Spring Harbor, N.Y. Sections 1.101 to 1.104, 16 and 17, 1989.
Samreen et al., "Hepatitis C virus entry: role of host and viral factors," Infect Genet Evol 12(8):1699-1709 (2012).

Schiedner et al., "Genomic DNA transfer with a high-capacity adenovirus vector results in improved in vivo gene expression and decreased toxicity," Nature Genetics 18:180-183 (1998).
Sharp, P. and E. Cowe, "Synonymous codon usage in Saccharomyces cerevisiae," Yeast 7(7): 657-678 (1991).
Shimada et al., "Targeted and highly efficient gene transfer into CD4+ cells by a recombinant human immunodeficiency virus retroviral vector,"J Clin. Invest. 88(3): 1043-1047 (1991).
Sorge et al., "Amphotropic retrovirus vector system for human cell gene transfer," Mol. Cell Biol. 4(9):1730-1737 (1984).
Stratford-Perricaudet, "Evaluation of the transfer and expression in mice of an enzyme-encoding gene using a human adenovirus vector," Hum Gene Ther 1(3): 241-256 (1990).
van Anken et al., "Only five of 10 strictly conserved disulfide bonds are essential for folding and eight for function of the HIV-1 envelope glycoprotein," Mol Biol Cell 19(10): 4298-4309 (2008).
Vieyres et al., "Characterization of the envelope glycoproteins associated with infectious hepatitis C virus," J Virol. 84:10159-10168, (2010).
Vieyres et al., "Characterization of antibody-mediated neutraliiation directed against the hypervariable region 1 of hepatitis C virus E2 glycoprotein," J. Gen. Virol. 92:494-506 (2011).
Wahid et al., "Disulfide bonds in hepatitis C virus glycoprotein E1 control the assembly and entry functions of E2 glycoprotein," J. Virol. 87(3):1605-1617 (2013).
Ward et al., "Binding activities of a repertoire of single immunoglobulin variable domains secreted from Escherichia coli," Nature 341(6242): 544-546 (1989).
Whidby et al., "Blocking hepatitis C virus infection with recombinant form of envelope protein 2 ectodomain," J. Virol. 83(21): 11078-11089 (2009).
Wilkinson, G. and A. Akrigg, "Constitutive and enhanced expression from the CMV major IE promoter in a defective adenovirus vector," Nucleic Acids Research 20(9):2233-2239 (1992).
Winter, G. and W. Harris, "Humanized antibodies," Trends Pharmacol. Sci 14(5):139-143 (1993).
Wittig et al., "Blue native PAGE," Nature Protocols, 1(1): 418-428 (2006).
Letter/Written Disclosure of the Information Disclosure Statement, filed on Aug. 25, 2014, 2 pages.
Angus, A. and A. Patel, "Immunotherapeutic potential of neutralizing antibodies targeting conserved regions of the HCV envelope glycoprotein E2," Future Microbiol 6():279-294 (2011).
Bartosch et al., "Cell entry of hepatitis C virus requires a set of co-receptors that include the CD81 tetraspanin and the SR-B1 scavenger receptor," J. Biol. Chem. 278(43):41624-41630 (2008).
Berkner, K., "Development of adenovirus vectors for the expression of heterologous genes," BioTechniques 6:616-629 (1988).
Boo et al., "Distinct roles in folding, CD81 receptor binding and viral entry for conserved histidine residues of hepatitis C virus glycoprotein E1 and E2," Biochem J. 443(1):85-94 (2012).
Drummer et al., "Challenges to the development of vaccines to hepatitis C virus that elicit neutralizing antibodies," Front Microbiol. 5:329, 10 pages (2014).
Drummer et al., "Mutagenesis of a conserved fusion peptide-like motif and membrane-proximal heptad-repeat region of hepatitis C virus glycoprotein E1," J. Gen. Virol. 88:1144-1148 (2007).
Grove et al., "Identification of a residue in hepatitis C virus E2 glycoprotein that determines scavenger receptor B1 and CD81 receptor dependency and sensitivity to neutralizing antibodies," J Virol. 82(24):12020-12029 (2008).
Kabat et al., Sequences of Proteins of Immunological Interest, 5th Ed, US Department of Health and Human Services, PHS, NIH, NIH Publication No. 91-3242, 3 pages (1991).
Kunkel et al., "Rapid and efficient site-specific mutagenesis without phenotypic selection," Methods in Enzymol., 154:367-382 (1987).
Law et al., "Broadly neutralizing antibodies protect against hepatitis C virus quasispecies challenge," Nature Medicine 14(1):25-27 (2008).
Mancini et al., "Hepatitis C virus (HCV) infection may elicit neutralizing antibodies targeting epitopes conserved in all viral genotypes," PLoS One 4:e8254, 7 pp. (2009).

(56) References Cited

OTHER PUBLICATIONS

McCaffrey et al., "Role of conserved cysteine residues in hepatitis C virus glycoprotein E2 folding and function," J. Virol. 86(7): 3961-3974 (2012).

McCaffrey et al., "The variable regions of hepatitis C virus glycoprotein E2 have an essential structural role in glycoprotein assembly and virion infectivity," J. Gen. Virol. 92(1):112-121 (2011).

McKeating et al., "Diverse hepatitis C virus glycoproteins mediate viral infection in a CD81-dependent manner," J. Virol. 78(16):8496-8505 (2004).

Pestka et al., "Rapid induction of virus-neutralizing antibodies and viral clearance in a single-source outbreak of hepatitis C," Proc. Natl. Acad. Sci. USA 104(14):6025-6030 (2007).

Pileri et al., "Binding of hepatitis C virus to CD81," Science 282:938-941 (1998).

Poumbourios, P. and H. Drummer, "Recent advances in our understanding of receptor binding, viral fusion and cell entry of hepatitis C virus: new targets for the design of antiviral agents," Antivir Chem Chemother. 18(4):169-189 (2007).

Rodriguez-Rodriguez et al., "Structural properties of the ectodomain of hepatitis C virus E2 envelope protein," Virus Research 139(1):91-99 (2009).

Stamataki et al., "Hepatitis C virus entry and neutralization," Clinics in Liver Disease 12(3):693-712 (2008).

Wang et al., "Alanine scanning mutagenesis of hepatitis C virus E2 cysteine residues: Insights into E2 biogenesis and antigenicity," Virology 448:229-237 (2014).

Zhang et al., "CD81 is required for hepatitis C virus glycoprotein-mediated viral infection," J. Virol. 78(3):1448-1455 (2004).

International Preliminary Report on Patentability, issued May 28, 2013, in connection with corresponding International Patent Application, PCT/AU2011/001534, 5 pages.

Written Opinion of the International Searching Authority, issued Jan. 10, 2012, in connection with corresponding International Patent Application, PCT/AU2011/001534, 4 pages.

International Search Report, issued Jan. 10, 2012, in connection with corresponding International Patent Application, PCT/AU2011/001534, 4 pages.

Response to Rule 161(2) and 162 communication, submitted Sep. 30, 2013, in connection with European Patent Patent Application No. 11 813 954.2, 7 pages.

Extended European Search Report and Written Opinion, issued Nov. 27, 2013, in connection with corresponding European Patent Application No. 11 813 954.2, 6 pages.

Examination Report, issued May 21, 2014, in connection with corresponding Australian Patent Application No. 2011286168, 3 pages.

Response to Search Report and Written Opinion, submitted Jun. 23, 2014, in connection with corresponding European Patent Patent Application No. 11 813 954.2, 7 pages.

Letter/Written Disclosure of the Information Disclosure Statement for the above-referenced application, mailed on May 21, 2015, 2 pages.

Notice of Acceptance, issued May 14, 2015, in connection with Australian Patent Application No. 2011286168, 5 pages.

* cited by examiner

A

B

SEQUENCE LISTING

```
<160> NUMBER OF SEQ ID NOS: 4

<210> SEQ ID NO 1
<211> LENGTH: 299
<212> TYPE: PRT
<213> ORGANISM: Hepatitis C virus

<400> SEQUENCE: 1

Met Asn Pro Leu Leu Ile Leu Thr Phe Val Ala Ala Ala Leu Ala Glu
1               5                   10                  15

Thr His Val Thr Gly Gly Asn Ala Gly Arg Thr Thr Ala Gly Leu Val
            20                  25                  30

Gly Leu Leu Thr Pro Gly Ala Lys Gln Asn Ile Gln Leu Ile Asn Thr
        35                  40                  45

Asn Gly Ser Trp His Ile Asn Ser Thr Ala Leu Asn Cys Asn Glu Ser
    50                  55                  60

Leu Asn Thr Gly Trp Leu Ala Gly Leu Phe Tyr Gln His Lys Phe Asn
65                  70                  75                  80

Ser Ser Gly Cys Pro Glu Arg Leu Ala Ser Cys Arg Arg Leu Thr Asp
                85                  90                  95

Phe Ala Gln Gly Trp Gly Pro Ile Ser Tyr Ala Asn Gly Ser Gly Leu
            100                 105                 110

Asp Glu Arg Pro Tyr Cys Trp His Tyr Pro Pro Arg Pro Cys Gly Ile
        115                 120                 125

Val Pro Ala Lys Ser Val Cys Gly Pro Val Tyr Cys Phe Thr Pro Ser
    130                 135                 140

Pro Val Val Val Gly Thr Thr Asp Arg Ser Gly Ala Pro Thr Tyr Ser
145                 150                 155                 160

Trp Gly Ala Asn Asp Thr Asp Val Phe Val Leu Asn Asn Thr Arg Pro
                165                 170                 175
```

```
Pro Leu Gly Asn Trp Phe Gly Cys Thr Trp Met Asn Ser Thr Gly Phe
            180                 185                 190

Thr Lys Val Cys Gly Ala Pro Pro Cys Val Ile Gly Val Gly Asn
        195                 200                 205

Asn Thr Leu Leu Cys Pro Thr Asp Cys Phe Arg Lys His Pro Glu Ala
        210                 215                 220

Thr Tyr Ser Arg Cys Gly Ser Gly Pro Trp Ile Thr Pro Arg Cys Met
225                 230                 235                 240

Val Asp Tyr Pro Tyr Arg Leu Trp His Tyr Pro Cys Thr Ile Asn Tyr
                245                 250                 255

Thr Ile Phe Lys Val Arg Met Tyr Val Gly Gly Val Glu His Arg Leu
            260                 265                 270

Glu Ala Ala Cys Asn Trp Thr Arg Gly Glu Arg Cys Asp Leu Glu Asp
        275                 280                 285

Arg Asp Arg Ser Glu His His His His His
        290                 295

<210> SEQ ID NO 2
<211> LENGTH: 299
<212> TYPE: PRT
<213> ORGANISM: Hepatitis C virus

<400> SEQUENCE: 2

Met Asn Pro Leu Leu Ile Leu Thr Phe Val Ala Ala Leu Ala Glu
1               5                   10                  15

Thr His Val Thr Gly Gly Asn Ala Gly Arg Thr Thr Ala Gly Leu Val
            20                  25                  30

Gly Leu Leu Thr Pro Gly Ala Lys Gln Asn Ile Gln Leu Ile Asn Thr
            35                  40                  45

Asn Gly Ser Trp His Ile Asn Ser Thr Ala Leu Asn Cys Asn Glu Ser
        50                  55                  60

Leu Asn Thr Gly Trp Leu Ala Gly Leu Phe Tyr Gln His Lys Phe Asn
65                  70                  75                  80

Ser Ser Gly Ala Pro Glu Arg Leu Ala Ser Cys Arg Arg Leu Thr Asp
                85                  90                  95

Phe Ala Gln Gly Trp Gly Pro Ile Ser Tyr Ala Asn Gly Ser Gly Leu
            100                 105                 110

Asp Glu Arg Pro Tyr Ala Trp His Tyr Pro Pro Arg Pro Cys Gly Ile
            115                 120                 125

Val Pro Ala Lys Ser Val Cys Gly Pro Val Tyr Cys Phe Thr Pro Ser
        130                 135                 140

Pro Val Val Val Gly Thr Thr Asp Arg Ser Gly Ala Pro Thr Tyr Ser
145                 150                 155                 160

Trp Gly Ala Asn Asp Thr Asp Val Phe Val Leu Asn Asn Thr Arg Pro
                165                 170                 175

Pro Leu Gly Asn Trp Phe Gly Cys Thr Trp Met Asn Ser Thr Gly Phe
            180                 185                 190

Thr Lys Val Cys Gly Ala Pro Pro Ala Val Ile Gly Val Gly Asn
        195                 200                 205

Asn Thr Leu Leu Ala Pro Thr Asp Ala Phe Arg Lys His Pro Glu Ala
        210                 215                 220

Thr Tyr Ser Arg Ala Gly Ser Gly Pro Trp Ile Thr Pro Arg Cys Met
225                 230                 235                 240

Val Asp Tyr Pro Tyr Arg Leu Trp His Tyr Pro Cys Thr Ile Asn Tyr
                245                 250                 255
```

```
Thr Ile Phe Lys Val Arg Met Tyr Val Gly Val Glu His Arg Leu
        260                 265                 270

Glu Ala Ala Cys Asn Trp Thr Arg Gly Glu Arg Ala Asp Leu Glu Asp
            275                 280                 285

Arg Asp Arg Ser Glu His His His His His
        290                 295

<210> SEQ ID NO 3
<211> LENGTH: 248
<212> TYPE: PRT
<213> ORGANISM: Hepatitis C virus

<400> SEQUENCE: 3

Met Asn Pro Leu Leu Ile Leu Thr Phe Val Ala Ala Leu Ala Glu
1               5                   10                  15

Thr His Gln Asn Ile Gln Leu Ile Asn Thr Asn Gly Ser Trp His Ile
            20                  25                  30

Asn Ser Thr Ala Leu Asn Cys Asn Glu Ser Leu Asn Thr Gly Trp Leu
        35                  40                  45

Ala Gly Leu Phe Tyr Gln His Lys Phe Asn Ser Ser Gly Cys Pro Glu
    50                  55                  60

Arg Leu Ala Ser Cys Gly Ser Ser Gly Cys Trp His Tyr Pro Pro Arg
65                  70                  75                  80

Pro Cys Gly Ile Val Pro Ala Lys Ser Val Cys Gly Pro Val Tyr Cys
                85                  90                  95

Phe Thr Pro Ser Pro Val Val Val Gly Thr Thr Asp Arg Ser Gly Ala
            100                 105                 110

Pro Thr Tyr Ser Trp Gly Ala Asn Asp Thr Asp Val Phe Val Leu Asn
        115                 120                 125

Asn Thr Arg Pro Pro Leu Gly Asn Trp Phe Gly Cys Thr Trp Met Asn
    130                 135                 140

Ser Thr Gly Phe Thr Lys Val Cys Gly Ala Pro Pro Cys Gly Ser Ser
145                 150                 155                 160

Gly Cys Pro Thr Asp Cys Phe Arg Lys His Pro Glu Ala Thr Tyr Ser
                165                 170                 175

Arg Cys Gly Ser Gly Pro Trp Ile Thr Pro Arg Cys Met Val Asp Tyr
            180                 185                 190

Pro Tyr Arg Leu Trp His Tyr Pro Cys Thr Ile Asn Tyr Thr Ile Phe
        195                 200                 205

Lys Val Arg Met Tyr Val Gly Gly Val Glu His Arg Leu Glu Ala Ala
    210                 215                 220

Cys Asn Trp Thr Arg Gly Glu Arg Cys Asp Leu Glu Asp Arg Asp Arg
225                 230                 235                 240

Ser Glu His His His His His
                245

<210> SEQ ID NO 4
<211> LENGTH: 248
<212> TYPE: PRT
<213> ORGANISM: Hepatitis C virus

<400> SEQUENCE: 4

Met Asn Pro Leu Leu Ile Leu Thr Phe Val Ala Ala Leu Ala Glu
1               5                   10                  15

Thr His Gln Asn Ile Gln Leu Ile Asn Thr Asn Gly Ser Trp His Ile
            20                  25                  30
```

-continued

```
Asn Ser Thr Ala Leu Asn Cys Asn Glu Ser Leu Asn Thr Gly Trp Leu
        35              40              45
Ala Gly Leu Phe Tyr Gln His Lys Phe Asn Ser Ser Gly Ala Pro Glu
 50              55              60
Arg Leu Ala Ser Cys Gly Ser Ser Gly Ala Trp His Tyr Pro Pro Arg
 65              70              75              80
Pro Cys Gly Ile Val Pro Ala Lys Ser Val Cys Gly Pro Val Tyr Cys
             85              90              95
Phe Thr Pro Ser Pro Val Val Val Gly Thr Thr Asp Arg Ser Gly Ala
            100             105             110
Pro Thr Tyr Ser Trp Gly Ala Asn Asp Thr Asp Val Phe Val Leu Asn
            115             120             125
Asn Thr Arg Pro Pro Leu Gly Asn Trp Phe Gly Cys Thr Trp Met Asn
            130             135             140
Ser Thr Gly Phe Thr Lys Val Cys Gly Ala Pro Pro Ala Gly Ser Ser
145             150             155             160
Gly Ala Pro Thr Asp Ala Phe Arg Lys His Pro Glu Ala Thr Tyr Ser
            165             170             175
Arg Ala Gly Ser Gly Pro Trp Ile Thr Pro Arg Cys Met Val Asp Tyr
            180             185             190
Pro Tyr Arg Leu Trp His Tyr Pro Cys Thr Ile Asn Tyr Thr Ile Phe
            195             200             205
Lys Val Arg Met Tyr Val Gly Gly Val Glu His Arg Leu Glu Ala Ala
            210             215             220
Cys Asn Trp Thr Arg Gly Glu Arg Ala Asp Leu Glu Asp Arg Asp Arg
225             230             235             240
Ser Glu His His His His His His
                245
```

MODIFIED HEPATITIS C VIRUS PROTEINS

RELATED APPLICATIONS

This application is the National Stage of International Application. No. PCT/AU2011/000991, filed 4 Aug. 2011, which claims benefit of priority to AU2010903478, filed 4 Aug. 2010, the specification of which is incorporated by reference herein.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file was created on Jan. 28, 2013, is 10 kilobytes in size, and titled 752USseqUS1.txt.

FIELD

The present invention relates to modified Hepatitis C virus (HCV) E2 proteins and methods of producing and using same.

BACKGROUND

Bibliographic details of the publications referred to by author in this specification are collected at the end of the description.

Reference to any prior art in this specification is not, and should not be taken as, an acknowledgment or any form of suggestion that that prior art forms part of the common general knowledge in any country.

Hepatitis C virus (HCV) is a major public health problem with over 123 million chronic infections estimated worldwide. There is no vaccine or post-exposure prophylaxis available. Currently available therapeutic treatment is limited to administration of ribivirin and pegylated interferon which displays limited efficacy of between 40-80% and causes severe side effects. HCV is the only member of the genus, Hepacivirus within the Flaviviridae family and is grouped into six major genotypes (1-6) and various subtypes (a, b, c, etc.). The high degree of sequence diversity proves a major challenge to the development of a universal vaccine to prevent HCV infection.

HCV encodes two envelope glycoproteins, E1 and E2, present as a heterodimer at the virion surface that mediate viral attachment and fusion to facilitate virus entry. The E1 and E2 glycoproteins are targets for the host immune response, vaccine strategies and the development of antiviral agents.

HCV cellular entry factors include the tetraspanin CD81, scavenger receptor class-B type-I (SR-B1), and the tight-junction membrane proteins Claudin 1, 6, or 9 and Occludin. Several discontinuous CD81-binding motifs have been identified within E2 and are proposed to assemble during folding including polypeptide residue $Trp^{420}$, $Trp^{437}$, Leu438, $Leu^{441}$, $Phe^{442}$, $Tyr^{577}$, $Trp^{529}$, $Gly^{530}$ and $Asp^{535}$ as well as amino-acids within the region 613-618. Interactions between the HCV glycoproteins and either Claudin or Occludin have not yet been described although both are essential cofactors for viral entry.

E1 and E2 are type-I transmembrane proteins that are heavily modified during biosynthesis at 4 or 5 and 11 N-linked glycosylation sites, respectively. Expression of E1 and E2 in cis is required for the formation of the functional heterodimer that appears to undergo a slow, cooperative folding pathway facilitated by ER chaperones. Several heterodimerization determinants have been identified within the transmembrane domains of both glycoproteins, the membrane-proximal region of E2 and the $W^{487}HY$ motif within the E2 ectodomain.

Within glycoprotein E2, an independent folding domain (polyprotein residue 384-661) can be efficiently expressed and secreted from cells with the retention of CD8 1 and SR-B1 receptor binding. Located within this receptor-binding domain (RBD; $E2_{661}$) are three discrete variable regions; the N-terminal hypervariable region 1 (HVR1), HVR2 and the intergenotypic variable region (igVR). Both HVR2 and igVR are flanked by pairs of conserved cysteine residues and all 3 variable regions are believed to be solvent exposed and excluded from the core domain. The E2 RBD is connected to the transmembrane domain (TMD) via a membrane-proximal region containing a conserved heptad-repeat that appears to have structural and functional features analogous to the 'stem' region of the flavivirus class II fusion protein glycoprotein E and suggested that E2 may also represent a class II fusion protein.

Glycoproteins E1 and E2 possess 8 and 18 cysteine residues within their respective ectodomains that are conserved across the six major genotypes (FIG. 1A). The arrangement of cysteines and disulfide bonds within these proteins is under investigation, however, it is assumed that they play a role in forming or stabilizing protein folds and therefore play a role in viral binding to host cells, entry into host cells and immunogenicity within the host. Krey et al., *PLoS Pathog* 6(2): e1000762, 2010 have recently assigned the nine disulfide-bonds formed by these residues within the E2 ectodomain using trypsin proteolysis, redox chemistry and mass spectrometry analysis (Krey et al., 2010 (supra)). The strict conservation of cysteines is indicative of the critical role disulfide bonds play in scaffolding the three-dimensional structure of proteins. Together with secondary structure prediction modeling, Krey et al., 2010 (supra) further proposed a model of E2 as a class II fusion protein; a class of proteins that occur in a number of viruses within the Flaviviridae family (FIG. 1B).

In this class II model of HCV E2, the known CD81-binding regions mapped to the interface of domains I and III. Disulfides 1 and 5 stabilize the domain I β-sheet sandwich while 6, 7 and 8 are located within domain III. The igVR forms a 'hinge' between these two domains and disulfides 1 5 and 6. Disulfide 7 was not formally identified in any of the tryptic digests but is assumed to form a disulfide pair. HVR1 is an N-terminal extension external to domain I. Domain II is predicted to form a relatively unstructured domain containing three short-range disulfide pairs: disulfides 2 and 3 flanking HVR2 and disulfide 4 stabilizing the candidate fusion 'loop' represented by a sequence of glycine-rich hydrophobic residues between 502-520. Disulfide pair 9 is predicted to lie at the edge of domain III with C677 located within the membrane-proximal or proposed 'stem' region of E2.

The formation of disulfide-bonded aggregates and heterogeneous forms of E2 or E1E2 heterodimers when these proteins are recombinantly expressed in a range of expression systems has hindered structural and function studies of HCV. A modified HCV E2 protein that produces conformationally competent polypeptides without these disadvantages is highly sought after.

SUMMARY

Throughout this specification, unless the context requires otherwise, the word 'comprise', or variations such as 'comprises' or 'comprising', will be understood to imply the inclusion of a stated element or integer or group of elements or integers but not the exclusion of any other element or integer or group of elements or integers.

As used herein the singular forms 'a', 'an' and 'the' include plural aspects unless the context clearly dictates otherwise. Thus, for example, reference to 'a mutation' includes a single mutation, as well as two or more mutations; reference to 'a polypeptide' includes one polypeptide, as well as two or more polypeptides; and so forth.

Each embodiment in this specification is to be applied mutatis mutandis to every other embodiment unless expressly stated otherwise.

In one embodiment, the specification enables a composition comprising a hepatitis C virus (HCV) Envelope 2 (E2) polypeptide including a receptor binding variant, wherein the polypeptide is modified to comprise: (i) a cysteine mutated or disrupted at 2, 3, or 4 cysteines selected from C452, C486, C569, and C597; and wherein the polypeptide forms substantially fewer multimers by intermolecular disulfide bonding relative to the HCV E2 polypeptide without cysteine modification. In some embodiments, the modified polypeptide substantially retains CD81 binding.

In other embodiments, the polypeptide further comprises a cysteine mutated or disrupted at 1, 2, 3 or 4 of C581, C585, C652 and C677.

In some embodiments, the polypeptide further comprises mutation or disruption of C581 and C585.

In other embodiments, the polypeptide further comprises mutation or disruption of C652 or C652 and C677.

In another illustrative embodiment, C452, C486, C569, C597, C581 and C585 are mutated or disrupted.

In yet another embodiment, C452, C486, C569, C597, C581, C585, and C652 are mutated or disrupted.

In another embodiment, the specification enables a composition comprising a hepatitis C virus (HCV) Envelope 2 (E2) polypeptide including a receptor binding variant, wherein the polypeptide is modified to comprise: (i) a cysteine mutated or disrupted at 2, 3, or 4 cysteines selected from C452, C486, C569, and C597; and wherein the polypeptide forms substantially fewer multimers by intermolecular disulfide bonding relative to the HCV E2 polypeptide without cysteine modification. In some embodiments, the modified polypeptide substantially retains H53-binding.

In another aspect, the specification enables a composition comprising a hepatitis C virus (HCV) Envelope 2 (E2) polypeptide including a receptor binding variant, wherein the polypeptide is modified to comprise: (i) a cysteine mutated or disrupted at 2, 3, or 4 cysteines selected from C452, C486, C569, and C597 wherein the polypeptide folds as at least 40%, or at least 45%, or at least 50%, or at least 55%, or at least 60%, or at least 65%, or at least 70% monomers.

In some embodiments, the polypeptide folds as less than 70% multimers, or less than 65%, or less than 60%, or less than 55%, or less than 50%, or less than 45% or less than 40% multimers by intermolecular disulfide bonding relative to the HCV E2 polypeptide without cysteine modification.

In another embodiment, the polypeptide further comprises a cysteine mutated or disrupted at 1, 2, 3 or 4 of C581, C585, C652 and C677.

In some embodiments, the HCV E2 polypeptide is E2661 or a receptor binding portion or variant thereof.

In other embodiments, the HCV E2 polypeptide comprises a deletion in 1, 2, or 3 variable regions selected from HVR2, HVR1 and IgVR.

In another embodiment, the compositions further comprise a physiologically or pharmaceutically acceptable carrier and/or diluent.

These HCV E2 polypeptides, and the ability to produce the subject polypeptides will be useful in a wide range of diagnostic, therapeutic (e.g. immunisation, antibody production, vaccines or targeting agents), screening, manufacturing and research applications. In particular, the specification enables a composition comprising a hepatitis C virus (HCV) Envelope 2 (E2) polypeptide including a receptor binding variant, wherein the polypeptide is modified to comprise: (i) a cysteine mutated or disrupted at 2, 3, or 4 cysteines selected from C452, C486, C569, and C597; and wherein the polypeptide forms substantially fewer multimers by intermolecular disulfide bonding relative to the HCV E2 polypeptide without cysteine modification. In some embodiments, the modified polypeptide substantially retains H53-binding for use in the treatment or prevention of HCV infection or for use in the diagnosis or monitoring of HCV infection or monitoring of an anti-HCV treatment protocol or for use in screening for binding agents that prevent host cell entry by hepatitis C virus.

In some embodiments, the polypeptide further comprises a cysteine mutated or disrupted at 1, 2, 3 or 4 of C581, C585, C652 and C677. In some embodiments, the polypeptide further comprises a cysteine mutated or disrupted at C581 and C585. In other embodiments, the polypeptide further comprises mutation or disruption of C652 or C652 and C677. In another illustrative embodiment, C452, C486, C569, C597, C581 and C585 are mutated or disrupted. In yet another embodiment, C452, C486, C569, C597, C581, C585, and C652 are mutated or disrupted.

In another embodiment, the specification enables host cells or host cell cultures comprising a hepatitis C virus (HCV) Envelope 2 (E2) polypeptide including a receptor binding variant, wherein the polypeptide is modified to comprise: (i) a cysteine mutated or disrupted at 2, 3, or 4 cysteines selected from C452, C486, C569, and C597; and wherein the polypeptide forms substantially fewer multimers by intermolecular disulfide bonding relative to the HCV E2 polypeptide without cysteine modification. In some embodiments, the modified polypeptide substantially retains H53-binding.

In some embodiments, the polypeptide further comprises a cysteine mutated or disrupted at 1, 2, 3 or 4 of C581, C585, C652 and C677. In some embodiments, the polypeptide further comprises a cysteine mutated or disrupted at C581 and C585. In other embodiments, the polypeptide further comprises mutation or disruption of C652 or C652 and C677. In another illustrative embodiment, C452, C486, C569, C597, C581 and C585 are mutated or disrupted. In yet another embodiment, C452, C486, C569, C597, C581, C585, and C652 are mutated or disrupted.

In another aspect, the specification provides a method of producing an antibody in a subject, the method comprising administering to the subject a composition according to any one of claims 1 to 11 for a time and under conditions suitable to elicit an antibody response, wherein the composition comprising a hepatitis C virus (HCV) Envelope 2 (E2) polypeptide including a receptor binding variant, wherein the polypeptide is modified to comprise: (i) a cysteine mutated or disrupted at 2, 3, or 4 cysteines selected from C452, C486, C569, and C597; and wherein the polypeptide forms substantially fewer multimers by intermolecular disulfide bonding relative to the HCV E2 polypeptide without cysteine modification. In some embodiments, the modified polypeptide substantially retains H53-binding.

In some embodiments, the polypeptide further comprises a cysteine mutated or disrupted at 1, 2, 3 or 4 of C581, C585, C652 and C677. In some embodiments, the polypeptide further comprises a cysteine mutated or disrupted at C581 and C585. In other embodiments, the polypeptide further comprises mutation or disruption of C652 or C652 and C677. In another illustrative embodiment, C452, C486, C569, C597, C581 and C585 are mutated or disrupted. In yet another embodiment, C452, C486, C569, C597, C581, C585, and C652 are mutated or disrupted.

In another aspect, the specification provides a method of eliciting an immune response in a subject or patient, the method comprising administering to the subject a composition comprising a hepatitis C virus (HCV) Envelope 2 (E2) polypeptide including a receptor binding variant, wherein the polypeptide is modified to comprise: (i) a cysteine mutated or disrupted at 2, 3, or 4 cysteines selected from C452, C486, C569, and C597; and wherein the polypeptide forms substantially fewer multimers by intermolecular disulfide bonding relative to the HCV E2 polypeptide without cysteine modification. In some embodiments, the modified polypeptide substantially retains H53-binding for a time and under conditions suitable to elicit an immune response.

In some embodiments, the polypeptide further comprises a cysteine mutated or disrupted at 1, 2, 3 or 4 of C581, C585, C652 and C677. In some embodiments, the polypeptide further comprises a cysteine mutated or disrupted at C581 and C585. In other embodiments, the polypeptide further comprises mutation or disruption of C652 or C652 and C677. In another illustrative embodiment, C452, C486, C569, C597, C581 and C585 are mutated or disrupted. In yet another embodiment, C452, C486, C569, C597, C581, C585, and C652 are mutated or disrupted.

In another aspect, the specification provides a diagnostic kit or a solid substrate comprising a composition comprising a hepatitis C virus (HCV) Envelope 2 (E2) polypeptide including a receptor binding variant, wherein the polypeptide is modified to comprise: (i) a cysteine mutated or disrupted at 2, 3, or 4 cysteines selected from C452, C486, C569, and C597; and wherein the polypeptide forms substantially fewer multimers by intermolecular disulfide bonding relative to the HCV E2 polypeptide without cysteine modification. In some embodiments, the modified polypeptide substantially retains H53-binding.

In other embodiments, the polypeptide further comprises a cysteine mutated or disrupted at 1, 2, 3 or 4 of C581, C585, C652 and C677. In some embodiments, the polypeptide further comprises a cysteine mutated or disrupted at C581 and C585. In other embodiments, the polypeptide further comprises mutation or disruption of C652 or C652 and C677. In another illustrative embodiment, C452, C486, C569, C597, C581 and C585 are mutated or disrupted. In yet another embodiment, C452, C486, C569, C597, C581, C585, and C652 are mutated or disrupted.

In another aspect the specification provides method of producing a composition comprising at least 40%, or at least 45%, or at least 50%, or at least 55%, or at least 60%, or at least 65%, or at least 70% monomeric HCV E2 polypeptide, the method comprising expressing a polypeptide in a host cell and isolating the expressed product, wherein the polypeptide is an HCV E2 polypeptide including a receptor binding variant, and wherein the polypeptide is modified to comprise: (i) a cysteine mutated or disrupted at 2, 3, or 4 cysteines selected from C452, C486, C569, and C597.

In some embodiments, the polypeptide further comprises a cysteine mutated or disrupted at 1, 2, 3 or 4 of C581, C585, C652 and C677

In other embodiments, the polypeptide further comprises a cysteine mutated or disrupted C581 and C585 are mutated or disrupted.

In other embodiments, C652 or C652 and C677 are mutated or disrupted.

In some embodiments, C452, C486, C569, C597, C581 and C585 are mutated or disrupted.

In some embodiments, C452, C486, C569, C597, C581, C585, and C652 are mutated or disrupted.

In another expression of the invention, the specification provides a composition comprising HCV E2 polypeptide including a receptor binding variant, wherein the polypeptide is modified to comprise: (i) 1 cysteine mutated or disrupted at 2, 3, or 4 disulfides selected from disulfides 2, 3, 5, and 7; and wherein the polypeptide forms substantially fewer multimers by intermolecular disulfide bonding relative to the HCV E2 polypeptide without a modified cysteine.

In some embodiments, the polypeptide further comprises 1 or 2 cysteines mutated or disrupted at 1 or 2 disulfides selected from disulfides 6 and 9.

In accordance with this aspect, in some embodiments, the cysteine mutated or disrupted at 2, 3, or 4 disulfides selected from disulfides 2, 3, 5 and 7 are selected from: C452 leaving a free thiol at C459, C486 leaving a free thiol at C494, C569 leaving a free thiol at C564, and C597 leaving a free thiol at C620.

The above summary is not and should not be seen in any way as an exhaustive recitation of all embodiments of the present invention.

In accordance with this aspect, in some embodiments, the cysteine mutated or disrupted at 2, 3, or 4 disulfides selected from disulfides 2, 3, 5 and 7 are selected from: C452, C486, C569, and C597.

Reducing SDS-PAGE analysis of purified proteins as detected by radioisotope imaging was also included as a loading control (bottom panel). The expected migration of monomeric, dimeric, trimeric and higher molecular mass forms of $E2_{661}$-his are indicated. B. Quantitative analysis of different $E2_{661}$-his oligomers indicated as detected by native-PAGE. Bands corresponding in molecular mass to monomer, dimer, trimer and higher molecular mass forms of $E2_{661}$-his were quantitated using ImageQuant software and the percentage of each species calculated. Data shown is the average of two independent experiments.

Figure 9:
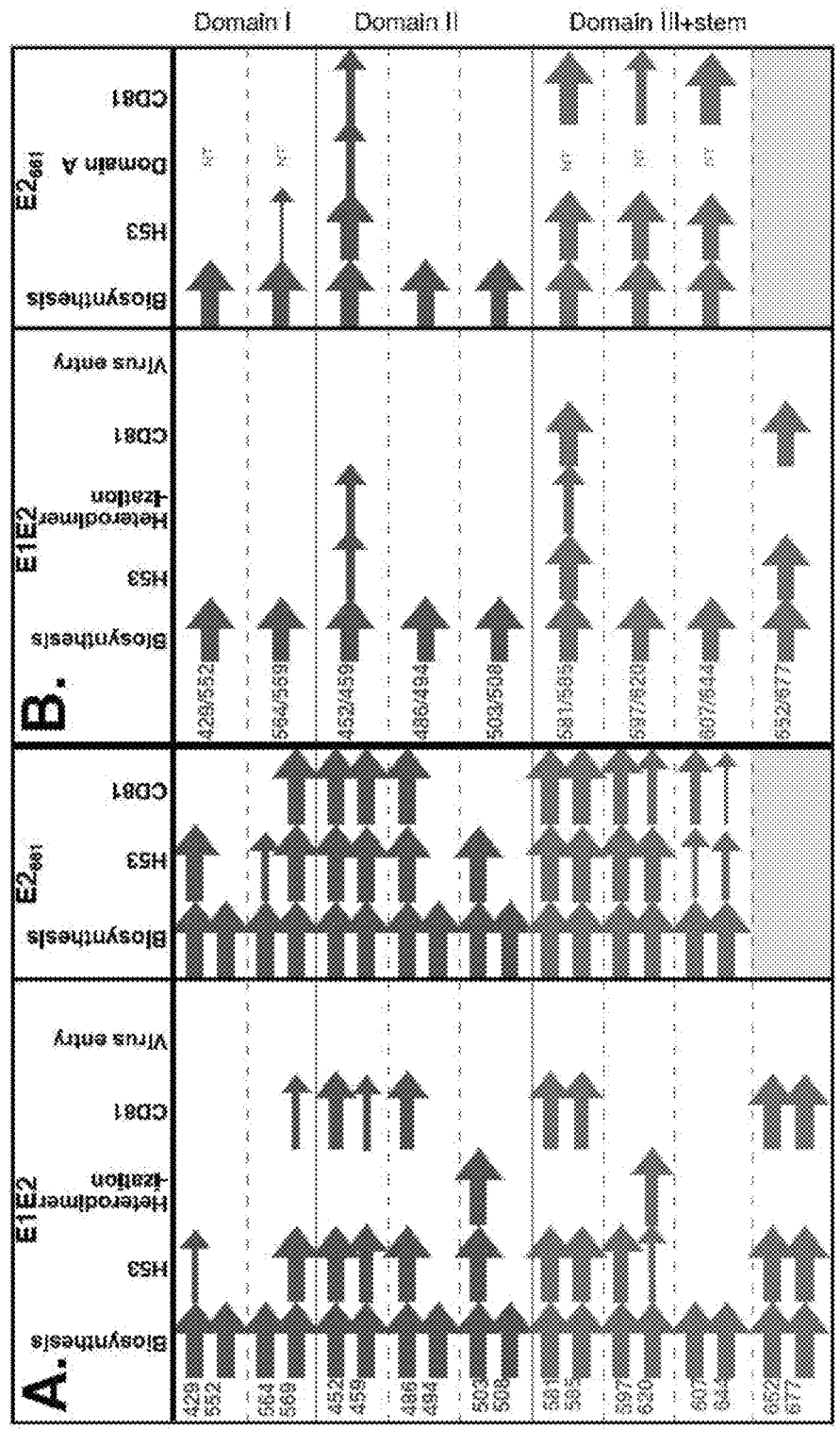

FIG. 9 is diagrammatic representation illustrating the hierarchy of phenotypes observed for (A) individual cysteine mutations and (B) disulfides in E1E2 and $E2_{661}$. Data derived from FIGS. 2 and 4(A) and 3 and 5(B).

Figure 10:
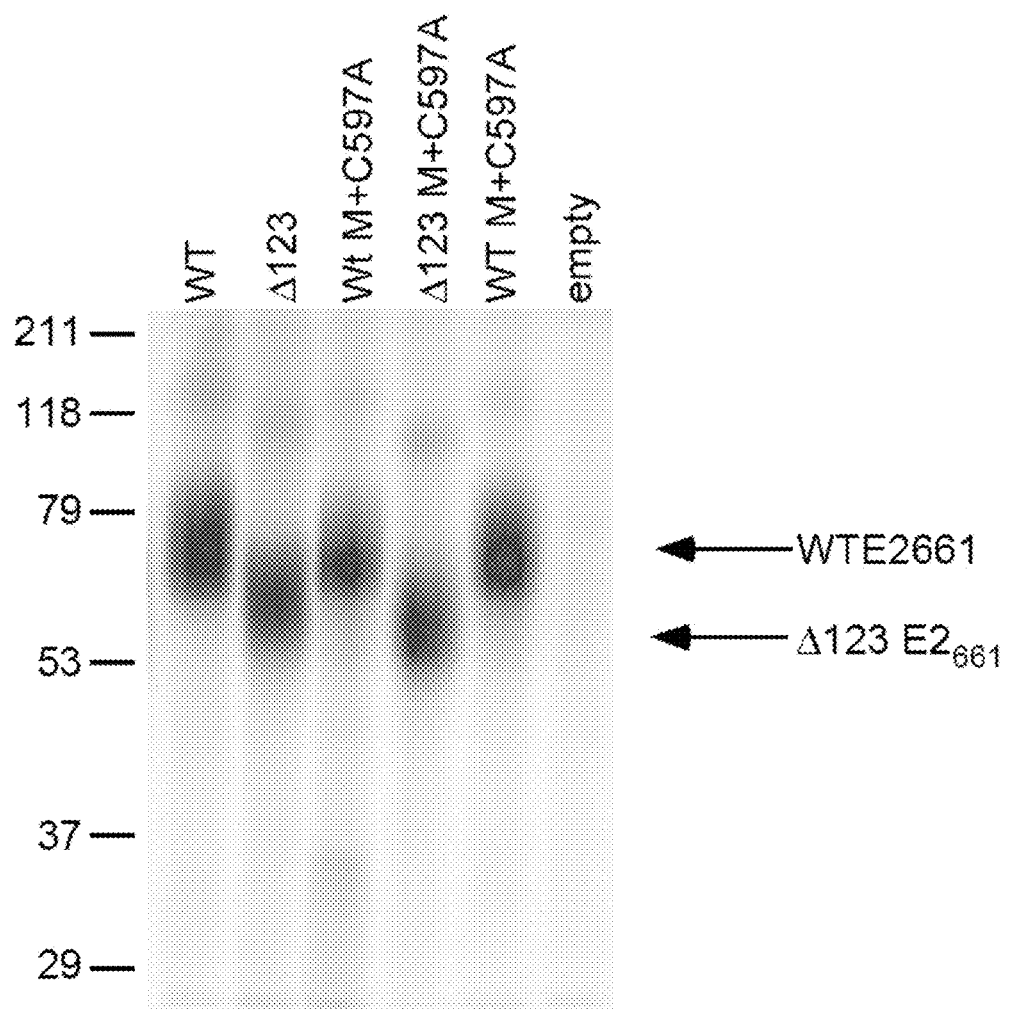
Figure 11A:
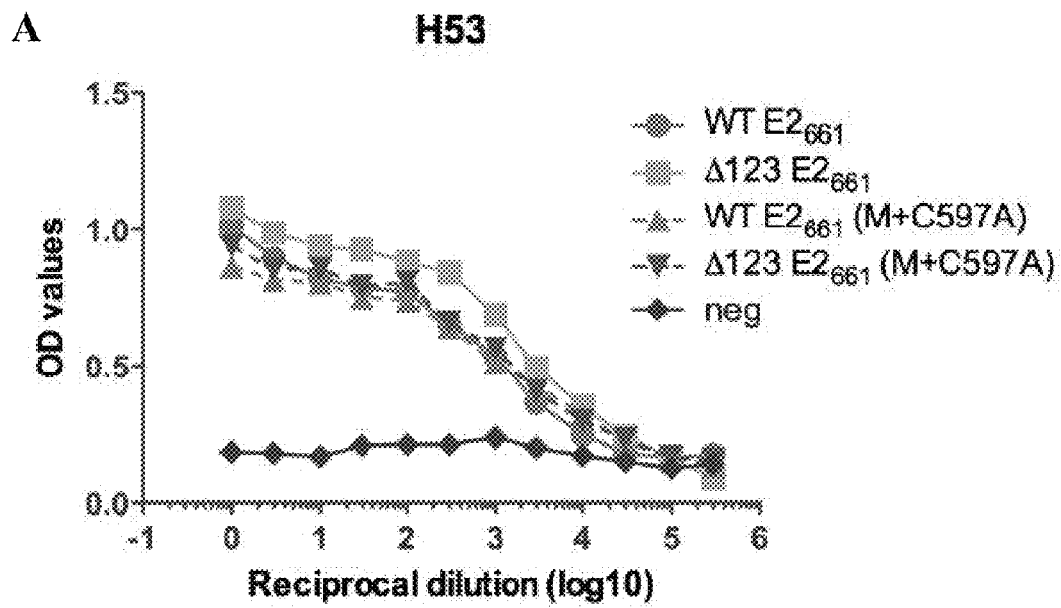
Figure 11B:
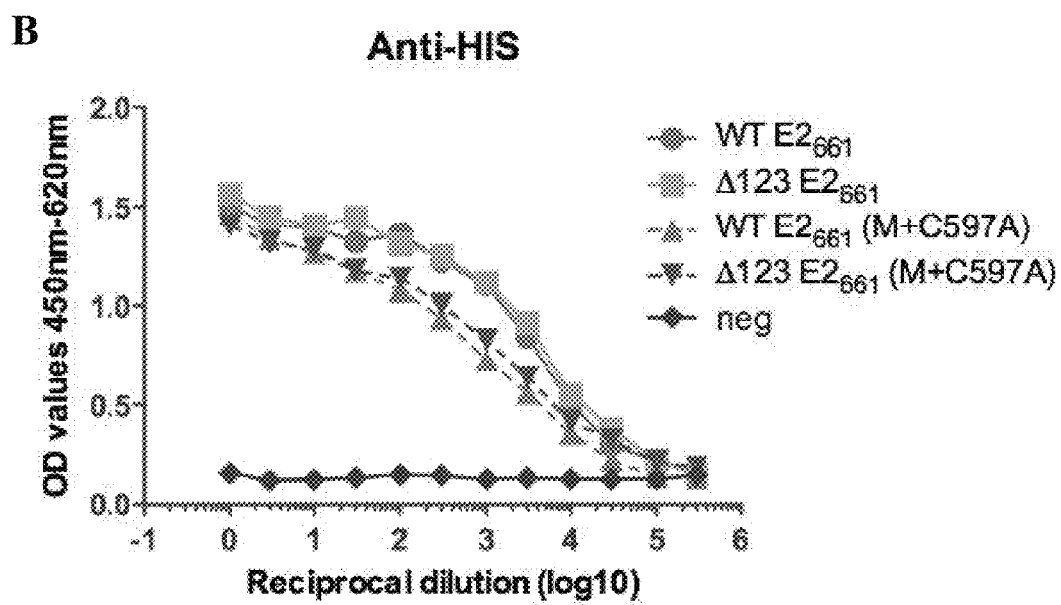
Figure 11C:
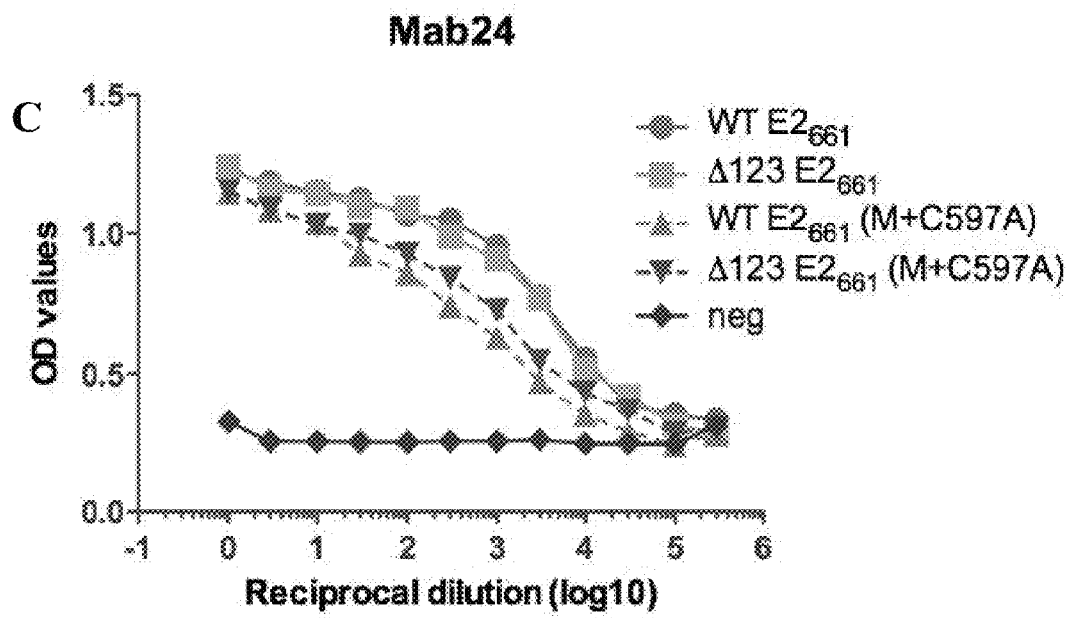
Figure 11D:
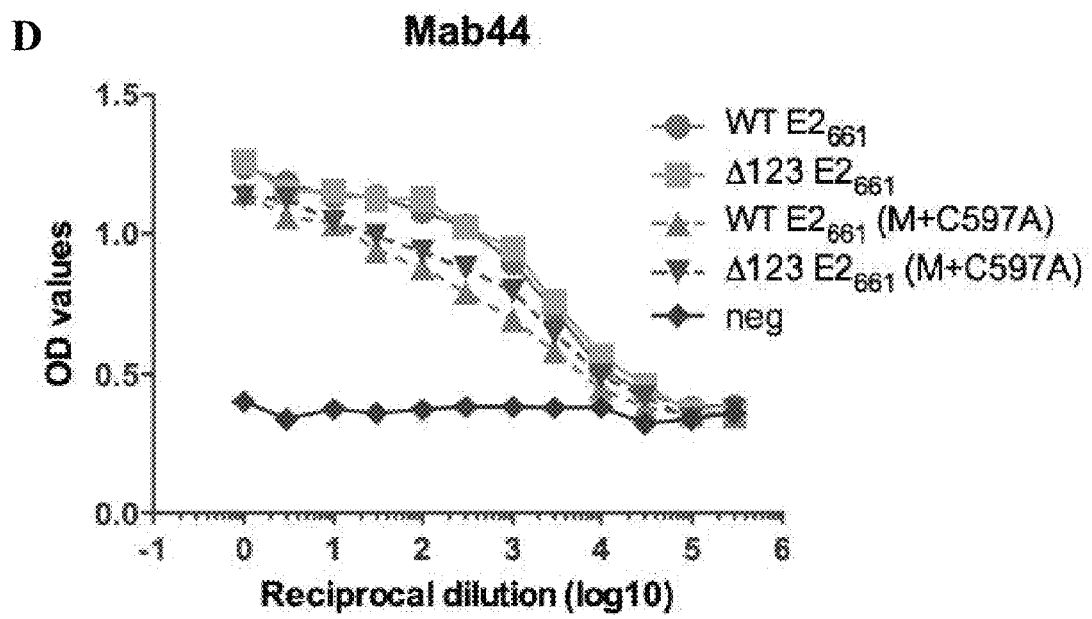

FIG. 10 is a photographic representation of gel separation showing simultaneous mutation of C452A, C486A, C569A, C581A, C585A, C597A and C652A (M+C597A) in both wild-type $E2_{661}$ and $\Delta 123$ $E2_{661}$ result in the expression of a secreted form of E2 that is recognized by conformation dependent monoclonal antibody H53. Transfected 293T cells were biosynthetically labeled with $^{35}$S-Met/Cys overnight. The tissue culture fluid was then collected and immunoprecipitated with MAb H53 and protein G sepharose. Samples were run under non-reducing conditions on 10% SDS-PAGE and phosphorimaged. Molecular weight markers are shown to the left and the position of WT $E2_{661}$ and the $\Delta 123$ $E2_{661}$ shown on the right.

FIG. 11A through D is a graphical representation of data showing ability of WT $E2_{661}$ (M+C597A) and $\Delta 123$ $E2_{661}$ (M+C597A) proteins to be recognized by neutralizing monoclonal antibodies and conformation dependent antibody H53. Enzyme immunoassay plates were coated with GNA lectin followed by $E2_{661}$ at 100 ng/well. Antibodies were serially diluted across plates and bound immunoglobulin detected using rabbit anti-mouse horse-radish peroxidase conjugated antibodies. Absorbance was measured at 450 nm with background subtraction at 620 nm.

Figure 12A:
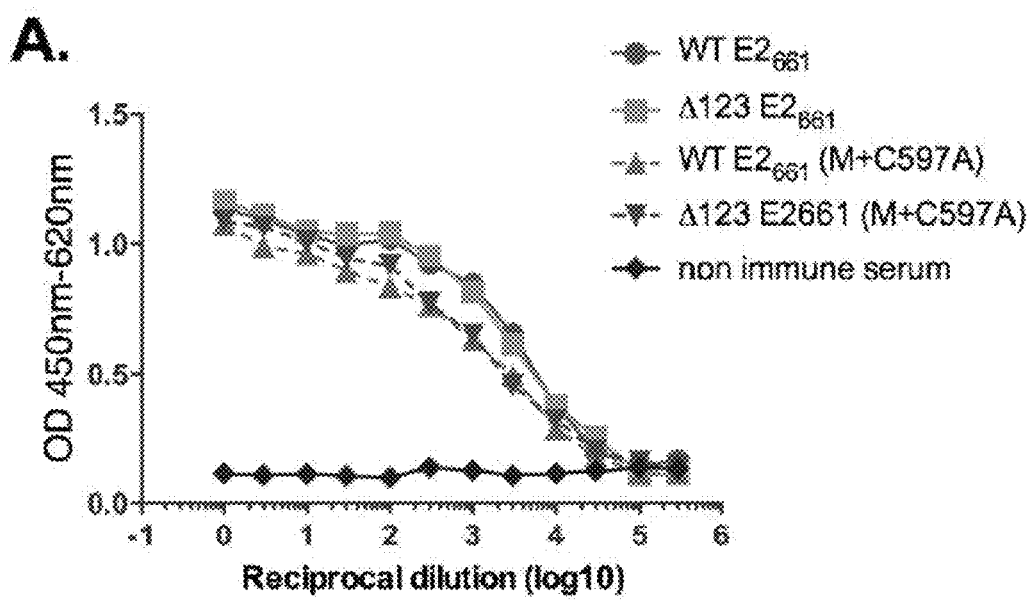
Figure 12B:
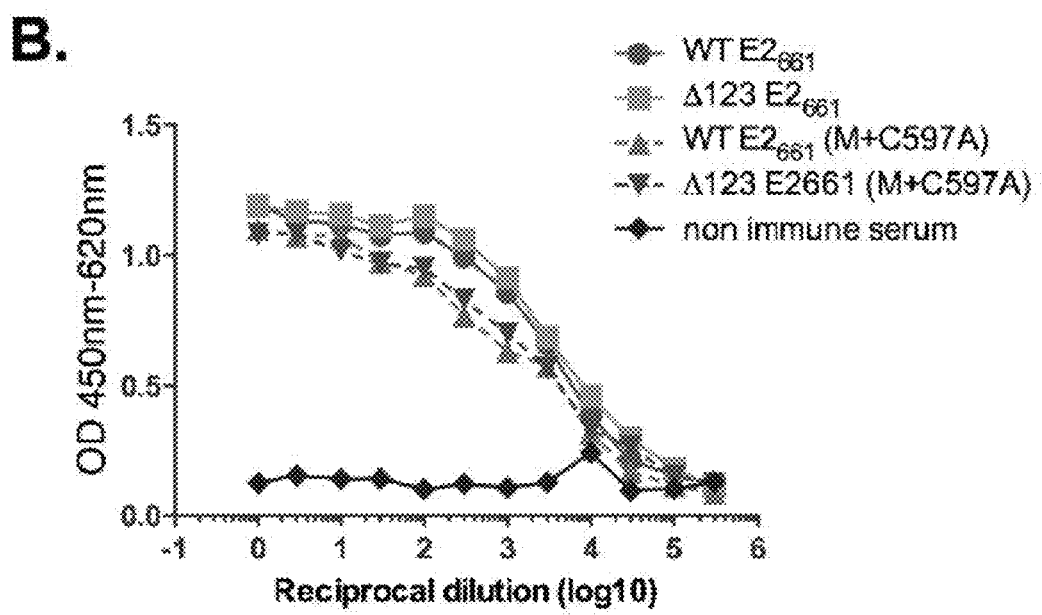

FIG. 12A through B is a graphical representation of data showing ability of WT $E2_{661}$ (M+C597A) and $\Delta 123$ $E2_{661}$ (M+C597A) proteins to be recognized by immune serum raised to WT $E2_{661}$ and $\Delta 123$ $E2_{661}$. Enzyme immunoassay plates were coated with GNA lectin followed by $E2_{661}$ at 100 ng/well. Antibodies were serially diluted across plates and bound immunoglobulin detected using anti-guinea pig horse-radish peroxidase conjugated antibodies. Absorbance was measured at 450 nm with background subtraction at 620 nm. Immune serum was generated in guinea pigs vaccinated with either WT $E2_{661}$(A) or $\Delta 123$ $E2_{661}$ (B).

Figure 13:
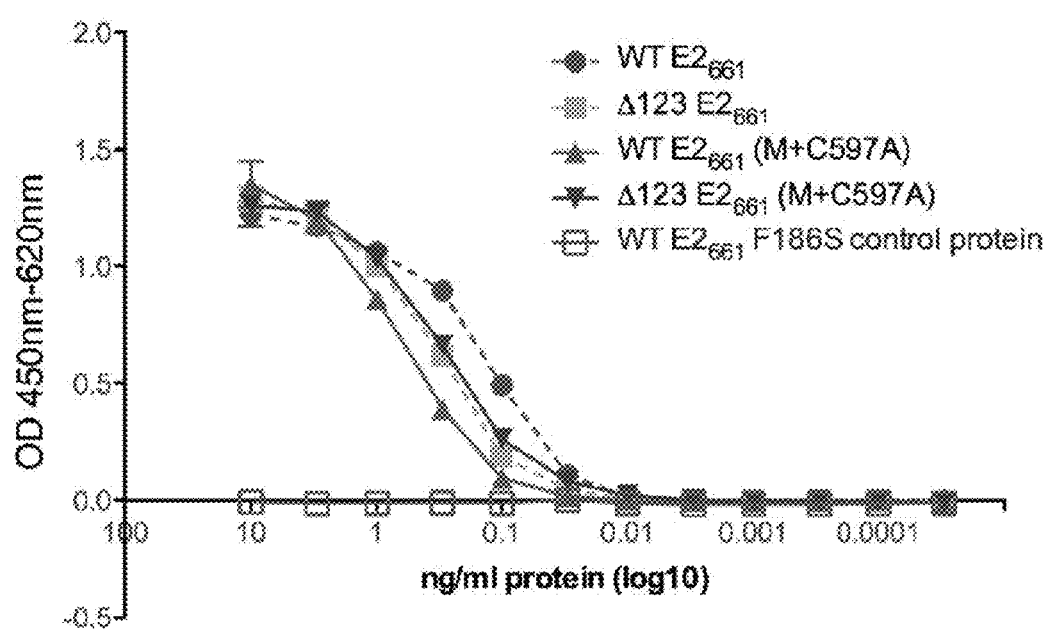

FIG. 13 is a graphical representation of data showing ability of WT $E2_{661}$ (M+C597A) and $\Delta 123$ $E2_{661}$ (M+C597A) proteins to bind CD81. Enzyme immunoassay plates were coated with MBP-LEL$^{113-201}$ and E2 protein serially diluted across plates. Bound E2 was detected with rabbit anti-His immunoglobulins and goat anti-rabbit horse-radish peroxidase conjugated antibodies. Absorbance was measured at 450nm with background subtraction at 620 nm. The control MBP-LEL$^{113-201}$ protein containing the mutation F186S in the E2 binding region was included to reveal the background of the assay using WT $E2_{661}$ protein (open squares).

Figure 14A:
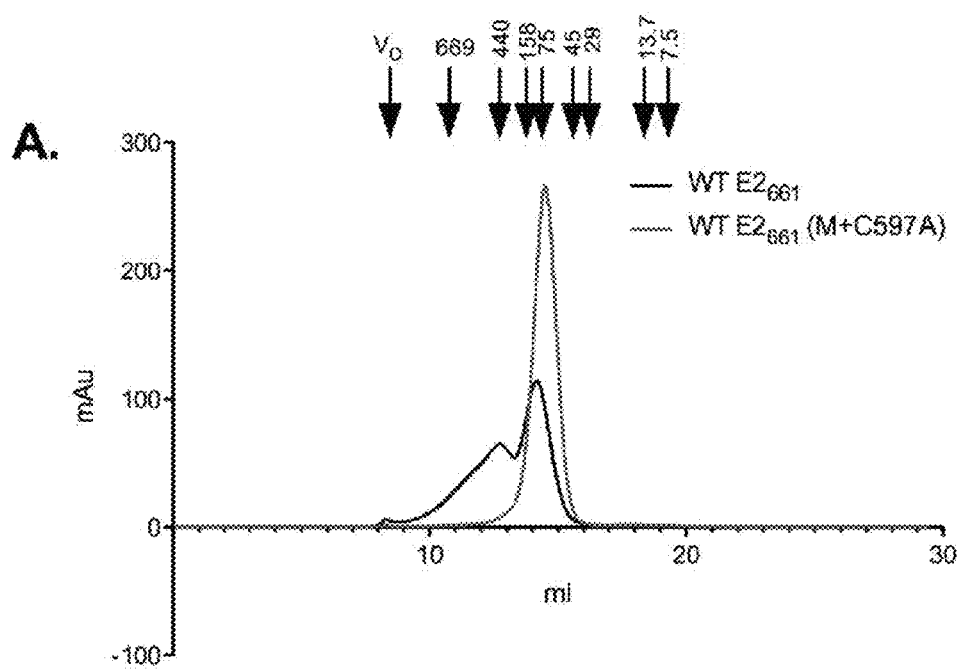
Figure 14B:
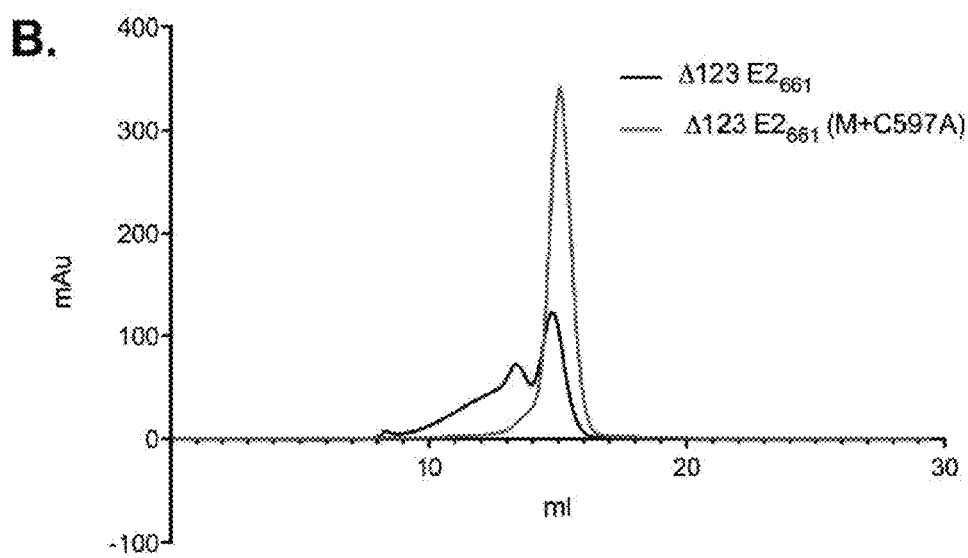

FIG. 14A through B is a graphical representation of data showing gel filtration chromatography of (A) WT $E2_{661}$ (M+C597A) and (B) $\Delta 123$ $E2_{661}$ (M+C597A) proteins. Superdex200 column was equilibrated in S buffer. Protein (~300 μg) was loaded onto columns and run at 0.5 ml/min. For comparison ~300 μg of the parental non mutated forms of WT $E2_{661}$ and $\Delta 123$ $E2_{661}$ were analysed.

BRIEF DESCRIPTION OF THE TABLES

Table 1 provides the location of the cysteine to alanine mutations in HCV glycoprotein E2. The location of the conserved cysteines within E2 are listed according to the amino acid numbering of the HCV polyprotein derived from the genotype 1a H77c isolate. The relative position of each cysteine numbered from 1 to 18 in the linear sequence is shown (1-18, N to C terminal) and the domain assignment shown according to Krey et al., 2010 (supra).

Table 2 provides disulfide pairing of the 18 Cys residues of HCV glycoprotein E2. Disulfide pairs as identified by Krey et al., 2010 (supra) and their domain assignment.

Table 3 provides a list of suitable naturally occurring proteogenic amino acids.

Table 4 provides an amino acid sub-classification.

Table 5 provides exemplary amino acid substitutions.

DETAILED DISCUSSION OF PREFERRED EMBODIMENTS

The subject invention is not limited to particular screening procedures for agents, specific formulations of agents and various medical methodologies, as such may vary. The terminology used herein is for the purpose of describing particular embodiments only and is not intended to be limiting.

Unless defined otherwise, all technical and scientific terms used herein have the same meanings as commonly understood by one of ordinary skill in the art to which this invention belongs. Any materials and methods similar or equivalent to those described herein can be used to practise or test the present invention. Practitioners are particularly directed to Ream et al., eds., *Molecular Biology Techniques: An Intensive Laboratory Course*, Academic Press, 1998; Newton and Graham eds., *PCR, Introduction to Biotechniques Series, 2nd ed.*, Springer Verlag, 1997; Sambrook et al., *Molecular Cloning: A Laboratory Manual*, Cold Spring Harbor Laboratory, Cold Spring Harbor, N.Y., 1989, Coligan et al., *Current Protocols in Protein Science*, John Wiley & Sons, Inc., 1995-1997, in particular Chapters 1, 5 and 6, and Ausubel et al., *Cell Immunol.*, 193(1): 99-107, 1999; Colowick and Kaplan, eds., *Methods In Enzymology*, Academic Press, Inc.; Weir and Blackwell, eds., *Handbook of Experimental Immunology, Vols. I-IV*, Blackwell Scientific Publications, 1986; Joklik ed., *Virology, 3rd Edition*, 1988; Fields and Knipe, eds, *Fundamental Virology, 2nd Edition*, 1991; Fields et al., eds, *Virology, 3rd Edition*, Lippincott-Raven, Philadelphia, Pa., 1996.

The term 'HCV E2 polypeptide', 'E2 polypeptide' or 'HCV E2' and the like includes an E2 polypeptide from any genotype of HCV. As known in the art, recombinant E2 ectodomain absent the transmembrane domain is secreted after folding in the presence of E1. The terms further include variants, including portions of the full length E2 polypeptide that, for example, mediate receptor binding, antibody binding by one or more antibodies that recognise conformation or other epitopes and/or mediate E1E2 dimer formation. One illustrative HCV E2 polypeptide is a receptor binding portion of E2 polypeptide comprising amino acids 384-661 of genotype H77 1a ($E2_{661}$ or E2e) or a corresponding portion from another HCV genotype. Accordingly, E2 polypeptides enabled includes all or part of the ectodomain that is required for CD81-binding absent the transmembrane domain. Further variants may include the addition or deletion/disruption of sequences necessary for cleavage or secretion. For example, $E^{384}$TH may be included, deleted or modified to modify signal peptide cleavage and glycoprotein secretion (McCaffrey et al., 2007 (supra)). Variants encompassing a range of mutations are described further herein.

In another embodiment, the C-terminal boundary, of the subject modified polypeptides includes from amino acid 661 to amino acid 771 including amino acids 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770 and 771.

The envelope glycoproteins of HCV are likely to exist on the surface of infectious virions as disulfide linked multimers. Evidence for this can be found in Fraser et al., *J Biol Chem* 2011, In print and in Vieyres et al., *J Virol* 84(19): 10159-10168, 2010; Vieyres et al., *J Virol* 1810-10, 2011. However, evidence that E2 may also exist as a monomer is found in Krey et al., *PLoS Pathog* 6(2): e1000762, 2010 and in the original work from Chiron. In some embodiments, it is proposed that E1E2 exist prior to attachment to receptors, as a disulfide linked multimer. Once the virus has attached to cells, a conformational change occurs that causes a thiol isomerization event to occur where labile disulfides are reduced allowing the protein to fold into a lower energy conformation. This conformation may be a monomer of E2 and may facilitate fusion peptide insertion and further conformational changes that drive membrane fusion. Therefore, a monomer of E2 may represent a folding intermediate of the virus entry cascade and represents an important antigen for immunisations and antibody generation.

Accordingly, in some embodiments, the more homogenous or monomeric form of E2 found in the subject modified HCV E2 polypeptide including M+C597A may be more representative of the folding intermediate and elicit antibodies that block entry at a later stage of the virus entry cascade.

A 'part' or 'portion' or 'region' or 'domain' of an HCV E2 polypeptide as having a minimal size of at least about 100 amino acids or about 100 to 200 amino acids or about 120 to 350 amino acids. This definition includes all sizes in the range 100 to 350 amino acids including 100, 200, 300 and 332 amino acids.

The portion of HCV E2 polypeptide contemplated encompasses regions of the E2 polypeptide that contain one or more conserved cysteines in its native form. In some embodiments, the portion is an immunogenic domain comprising conformational epitopes recognized by neutralizing or, in some embodiments, non-neutralising antibodies. There are various methods for determining suitable portions.

In some particular embodiments, variants including portions retain at least one desirable function of the parent E2 polypeptide such as, without limitation, receptor binding or binding by MAb 53. In addition, variants are selected that retain the ability to form greater amounts of monomer. As determined herein in some embodiments variants include portions of HCV E2 that encompass a disulphide 1, 4 and 8 or at least amino acids 429-644 are important for the CD81-binding site.

In other embodiments, variants include polypeptide or peptide that do not have one or more functional attributes of the parent polypeptide.

In accordance with the present invention, the inventors have determined that loss of a plurality of disulfides and/or the generation of free cysteine residues does not disrupt the overall folding and function of $E2_{661}$. The inventor(s) have determined that C581/C585 and C652/C677 are important for mediating E1 association and viral entry but not for the overall fold of E2 or assembly of a functional CD81 binding site.

As described in the Examples, the inventors have determined the number and position of conserved cysteines that can be mutated without loss of phenotypes such as secretion, heterodimerization, receptor binding, or binding by conformation-dependent antibodies: in addition, how individual or two or multiple cysteine disruptions modulate one or more of these functions. As illustrated herein, polypeptides can now be produced that retain conformational epitopes without receptor binding or alternatively wherein both of these functions are retained. This is surprising because disulfide bonds are proposed to stabilise the three dimensional structure and functional attributes of the E2 protein, specifically receptor binding and binding by antibodies that recognise conformational epitopes. While each of the conserved cysteines was identified as important for viral entry, the CD81 and H53 binding capability of E2 polypeptide was found to be strikingly tolerant to the presence of unpaired cysteine residues or absence of disulfide bonds. In an illustrative embodiment, simultaneous mutation of seven cysteines significantly increased monomer production and reduced dimer, trimer, and high molecular weight multimer production as determined by quantitative native-PAGE and gel filtration.

The numbering and nomenclature of conserved cysteines and mutations or disruptions thereof in E2 polypeptide follows that set out in Table 1. In particular, they are described by amino acid residue position within the HCV polypeptide sequences. For example, mutation 'C429A' refers to a cysteine to alanine substitution at amino acid 429 in HCV E2. The amino acid residue position and number may vary between genotypes or variants or depending upon where numbering commences. Conserved cysteines, 'cysteines' are also described by relative cysteine number position from the N-terminal to the C-terminal of the HCV E2 polypeptide, i.e. 1 to 18 in the full length HCV E2; 1 to 17 in $E_{661}$.

Throughout this specification, including the claims, all numbering of polypeptide residues of the HCV envelope glycoproteins E1 and E2 is based on the prototype HCV-H77 polyprotein sequence, Genbank Accession No. AF 009606. The mature form of glycoprotein E1 is encompassed by polyprotein residues 191 and 383, and the mature form of glycoprotein E2 is encompassed by polyprotein residues 384 and 746.

In addition, the cysteines are herein described by reference to the position of disulfides within the folded HCV E2 polypeptide as set out in FIG. 1. Other folded arrangements of the polypeptide are contemplated and the relative cysteine number of each cysteine in each disulfide in the folded molecule may be varied accordingly.

The numbering and nomenclature of disulfides follows that shown in Table 2 which also sets out their domain allocation. The assignment of different disulfides to domains I, II, or III of HCV E2 is also shown in Tables 1 and 2 and FIGS. 1 and 9.

Figure 1A:
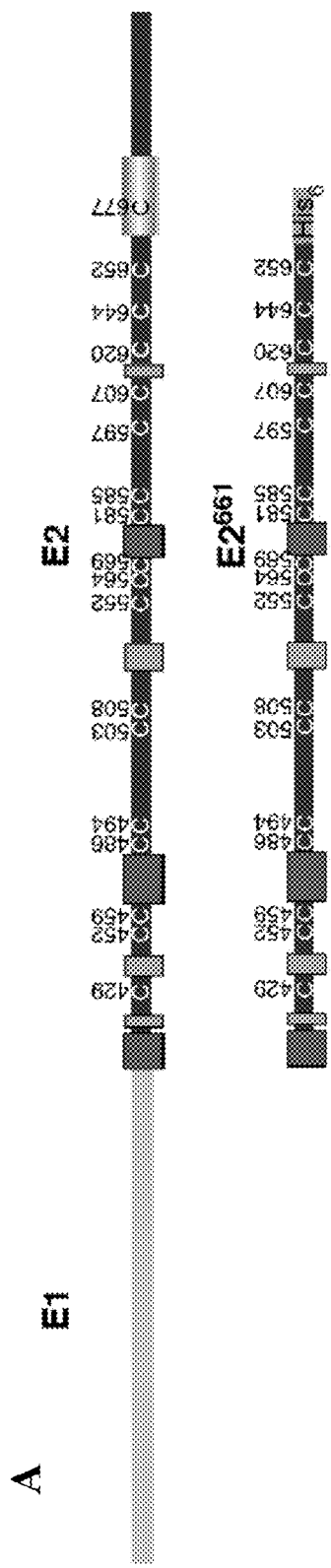
FIG. 1A through B are diagrammatic representations illustrating the location of conserved cysteines within HCV envelope glycoprotein E2. A. Schematic diagram of the E1E2 polyprotein and truncated E2 protein ($E2_{661}$). E1 sequence (polyprotein residues 191-383) is represented by light gray and E2 (384-746) in dark grey. The green boxes highlight the location of conserved CD81-binding motifs and the red boxes show the location of the three discrete variable sequences within E2: HVR1, HVR2 and igVR from the N- to C-terminus, respectively. The cylinder indicates the conserved membrane-proximal heptad-repeat or predicted 'stem' region. $E2_{661}$ is truncated at polyprotein residue 661 and has a C-terminal six-histidine tag. B. A schematic representation of the disulfide-bonding pattern within the E2 glycoprotein as modelled as a class II fusion protein (Krey et al., 2010 (supra)). The locations of domains I, II and III are labelled and the location of the predicted 'stem' region is indicated by the cylinder. HVR1, HVR2 and igVR sequences are also labelled and the predicted fusion peptide sequence (residues 502-520) within domain II is highlighted by a black-dashed line. The conserved cysteine residues (C) are marked and their corresponding disulfides indicated by a line bridging these amino-acids.

The cysteine/disulfide notation used herein study is summarized in FIG. 1.

In one broad embodiment, the present invention provides a plurality of modified HCV E2 polypeptides modified such that (i) one or two or more or all conserved cysteines in each polypeptide is mutated or disrupted or (ii) one or two or more or all disulfides in each polypeptide is mutated or disrupted at one or both cysteines.

In one embodiment, the specification enables a composition comprising a hepatitis C virus (HCV) Envelope 2 (E2) polypeptide including a receptor binding variant, wherein the polypeptide is modified to comprise: (i) a cysteine mutated or disrupted at 2, 3, or 4 cysteines selected from C452, C486, C569, and C597; and wherein the polypeptide forms substantially fewer multimers by intermolecular disulfide bonding relative to the HCV E2 polypeptide without cysteine modification. In some embodiments, the modified polypeptide substantially retains CD81- or H53-binding.

In other embodiments, the polypeptide further comprises a cysteine mutated or disrupted at 1, 2, 3 or 4 of C581, C585, C652 and C677.

In some embodiments, the polypeptide further comprises mutation or disruption of C581 and C585.

In other embodiments, the polypeptide further comprises mutation or disruption of C652 or C652 and C677.

In another illustrative embodiment, C452, C486, C569, C597, C581 and C585 are mutated or disrupted.

In yet another embodiment, C452, C486, C569, C597, C581, C585, and C652 are mutated or disrupted.

In another embodiment, the specification enables a composition comprising a hepatitis C virus (HCV) Envelope 2 (E2) polypeptide including a receptor binding variant, wherein the polypeptide is modified to comprise: (i) a cysteine mutated or disrupted at 2, 3, or 4 cysteines selected from C452, C486, C569, and C597; and wherein the polypeptide forms substantially fewer multimers by intermolecular disulfide bonding relative to the HCV E2 polypeptide without cysteine modification. In some embodiments, the modified polypeptide substantially retains H53-binding.

As used herein the phrases "substantially fewer multimers" or "substantially less multimers" refer to a polypeptide that forms less than 70% multimers, or less than 65%, or less than 60%, or less than 55%, or less than 50%, or less than 45% or less than 40% multimers (by weight).

In some embodiments, the phrase refers to less than 15% or less than 10% dimers.

In some embodiments, the phrase refers to less than 15% or less than 10% trimers.

In some embodiments, the phrase refers to less than 40% high molecular weight aggregates.

As used herein, the phrase "substantially retains CD81-binding" refers to a polypeptide having more than 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the level of CD81-binding by an HCV E2 polypeptide without cysteine modification or relative to a control polypeptide that does not have one or more modified cysteines.

As used herein, the phrase "substantially retains H53-binding" refers to a polypeptide having more than 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the level of H53-binding by an HCV E2 polypeptide without cysteine modification or relative to a control polypeptide that does not have one or more modified cysteines.

In another aspect, the specification enables a composition comprising a hepatitis C virus (HCV) Envelope 2 (E2) polypeptide including a receptor binding variant, wherein the polypeptide is modified to comprise: (i) a cysteine mutated or disrupted at 2, 3, or 4 cysteines selected from C452, C486, C569, and C597 wherein the polypeptide folds as at least 40%, or at least 45%, or at least 50%, or at least 55%, or at least 60%, or at least 65%, or at least 70% monomers.

In some embodiments, the polypeptide folds as less than 70% multimers, or less than 65%, or less than 60%, or less than 55%, or less than 50%, or less than 45% or less than 40% multimers by intermolecular disulfide bonding relative to the HCV E2 polypeptide without cysteine modification.

In some embodiments, the HCV E2 polypeptide is E2661 or a receptor binding portion thereof.

In some embodiments, the modified HCV E2 polypeptides further comprise a deletion of one or more variable regions.

In some embodiments therefore, the specification provides a composition of comprising a hepatitis C virus (HCV) Envelope 2 (E2) polypeptide including a receptor binding variant, wherein the polypeptide is modified to comprise: (i) a cysteine mutated or disrupted at 2, 3, or 4 cysteines selected from C452, C486, C569, and C597; and wherein the polypeptide forms substantially fewer multimers by intermolecular disulfide bonding relative to the HCV E2 polypeptide without cysteine modification. In some embodiments, the modified polypeptide substantially retains H53-binding wherein the HCV E2 polypeptide comprises a deletion in 1, 2, or 3 variable regions selected from HVR2, HVR1 and IgVR.

The terms 'polypeptide' 'protein' and 'peptide' and 'glycoprotein' are to be used interchangeably and mean a polymer of amino acids not limited to any particular length. The term does not exclude modifications such as myristylation, glycosylation, phosphorylation and addition or deletion of signal sequences.

E2 polypeptides or a protein or protein complex comprising same may be produced by recombinant or synthetic or a combination of these routes as known in the art.

'Synthetic' sequences, as used herein, include polynucleotides whose expression has been optimised as described herein, for example, by codon substitution, deletions, replacements and/or inactivation of inhibitory sequences. 'Wild-type' or 'native' or 'naturally occurring' sequences, as used herein, refers to polypeptide encoding sequences that are essentially as they are found in nature or prior to cysteine modification. The subject polynucleotide sequences may be codon optimised as known in the art.

Recombinant production may be produced by expression in eukaryotic or prokaryotic cells. Eukaryotic cells include mammalian, plant, yeast and insect cells as known in the art.

Cysteines may be disrupted by blocking by chemical means such as by sulphonation or alkylation. In some embodiments, blocking may be reversible or irreversible. Reversible blocking may be achieved chemically or enzymatically. Disruption or removal of disruption may also be achieved by use of chemical cross-linkers as known in the art.

Mutation or disruption of cysteines includes modification of nucleic acid encoding an HCV E2 polypeptide to encode an amino acid that does not have the ability to form disulfide bonds. Typically mutation is achieved by site directed mutagenesis protocols known in the art as described in Sambrook et al., 1989 (supra), Chapter 13. The term further includes modification of cysteines in situ by chemical or enzymatic methods that prevent disulfide formation.

Generally, cysteines may be engaged in intramolecular or intermolecular disulfide bonds (referred to as 'oxidized E2') or may be disrupted, e.g., by sulphonation (referred to as 'sulphonated E2') or alkylation (referred to as 'alkylated E2'). Alternatively, the cysteines carry a free thiol-group (referred to as 'reduced E2').

A disulphide bond is a covalent bond formed between the sulfhydryl groups of two cysteines. A cysteine may be engaged with another cysteine in an intramolecular (within a single E2 molecule) or intermolecular (between two or more E2 molecules) disulfide bond (referred to as 'oxidized E2') or may be disrupted, e.g., by reduction (reduced E2), by sulphonation (referred to as 'sulphonated E2') or alkylation (referred to as 'alkylated E2'). Alternatively, the cysteines are unpaired and not engaged in inter- or intra-molecular disulphide bonds and carry a free thiol-group (referred to as 'unpaired cysteines' or 'free thiols' or 'reduced cysteines'. In some embodiments, wherein the HCV E2 polypeptide is a truncated ectodomain of E2, if a cysteine absent as a result of truncation, this is taken to be a disrupted cystein.

An 'irreversibly disrupted cysteine' is a cysteine wherein the cysteine thiol-group is irreversibly protected. In particular, 'irreversible protection' or 'irreversible blocking' by chemical means refers to alkylation, preferably alkylation of a cysteine in a protein with an alkylating agents, such as, for example, active halogens, ethylenimine or N-(iodoethyl)trifluoro-acetamide. Alkylation of cysteine thiol-groups refers to the replacement of the thiol-hydrogen. Alkylation can be performed by any method known in the art, such as, for example, use of active halogens I, Br, Cl or F. Examples of active halogens are methyliodide, iodoacetic acid, iodoacetamide, and 2-bromoethylamine.

A 'reversibly disrupted cysteine' is a cysteine of which the cysteine thiol-groups is reversibly protected. In particular, the term 'reversible protection' or 'reversible disruption' as used herein contemplates covalently binding of modification agents to the cysteine thiol-groups, as well as manipulating the environment of the protein such, that the redox state of the cysteine thiol-groups remains (shielding). Reversible protection of the cysteine thiol-groups can be carried out chemically or enzymatically.

The term 'reversible disruption by enzymatical means' as used herein contemplates reversible disruption mediated by enzymes, such as for example acyl-transferases, e.g. acyltransferases that are involved in catalysing thio-esterification, such as palmitoyl acyltransferase.

The term 'reversible disruption by chemical means' as used herein contemplates reversible protection: (1) by modification agents that reversibly modify cysteinyls such as for example by sulphonation and thio-esterification; (2) by modification agents that reversibly modify the cysteinyls of the present invention such as, for example, by heavy metals, in particular $Zn^{2+}$, $Cd^{2+}$, mono-, dithio- and disulfide-compounds (e.g. aryl- and alkylmethanethiosulfonate, dithiopyridine, dithiomorpholine, dihydrolipoamide, Ellmann reagent, aldrothiol™ (Aldrich), dithiocarbamates), or thiolation agents (e.g. gluthathion, N-Acetyl cysteine, cysteineamine). Dithiocarbamate comprise a broad class of molecules possessing an $R_1R_2NC(S)SR_3$ functional group, which gives them the ability to react with sulphydryl groups.

Thiol containing compounds are preferentially used in a concentration of 0.1-50 mM, more preferentially in a concentration of 1-50 mM, and even more preferentially in a concentration of 10-50 mM; (3) by the presence of modification agents that preserve the thiol status (stabilise), in particular antioxidantia, such as for example DTT, dihydroascorbate, vitamins and derivates, mannitol, amino acids, peptides and derivates (e.g. histidine, ergothioneine, carnosine, methionine), gallates, hydroxyanisole, hydoxytoluene, hydroquinon, hydroxymethylphenol and their derivates in concentration range of 10 μM-10 mM, more preferentially in a concentration of 1-10 mM; (4) by thiol stabilising conditions such as, for example, (i) cofactors as metal ions ($Zn^{2+}$, $Mg^{2+}$), ATP, (ii) pH control (e.g. for proteins in most cases pH 5 or pH is preferentially thiol $pK_a$ (2); e.g. for peptides purified by Reversed Phase Chromatography at about pH 2). Combinations of reversible protection as described in (1), (2), (3) and (4) may be applied.

The removal of the reversible protection state of the cysteine residues can be accomplished chemically or enzymatically by, e.g.: a reductant, in particular DTT, DTE, 2-mercaptoethanol, dithionite, $SnCl_2$, sodium borohydride, hydroxylamine, TCEP, in particular in a concentration of 1-200 mM, more preferentially in a concentration of 50-200 mM; removal of the thiol stabilising conditions or agents by e.g. pH increase; enzymes, in particular thioesterases, glutaredoxine, thioredoxine, in particular in a concentration of 0.01-5 μM, even more particular in a concentration range of 0.1-5 μM.; or combinations of the above described chemical and/or enzymatical conditions.

By 'derived from' is meant naturally occurring forms and functional variants of naturally occurring forms and therefore includes sequences directly or indirectly derived from an organism. For example, a viral polypeptide is 'derived from' a particular polypeptide and HCV (viral polypeptide) if it is (i) encoded by an open reading frame of a polynucleotide of that virus (viral polynucleotide), or (ii) displays sequence similarity to polypeptides of that virus as described herein. A heterologous polypeptide is not derived from the same virus. A heterologous molecule or agent may be derived from any source, not necessarily from an organism.

In some embodiments, modified HCV E2 polypeptides are provided that fold predominately as monomers or as monomers at higher level than controls without the subject cysteine modification and/or with a reduced level of multimers compared to controls. It is proposed, in some embodiments, that modified HCV E2 polypeptides as described herein having two or more of conserved cysteines 1 to 16 mutated or disrupted have a reduced tendency to form intermolecular disulfide bonds while retaining conformational capabilities such as the overall fold of E2 and/or receptor binding capabilities. Accordingly, in some embodiments, it is proposed that the present invention provides HCV E2 polypeptides comprising even a plurality of disrupted conserved cysteines that in various embodiments are able to fold and form functional polypeptides capable of receptor binding or retaining native conformation and further comprises a reduced level of aberrant disulfide bonds compared to controls without these cysteines modifications.

In another broad embodiment, the present invention provides a modified HCV E2 polypeptide modified such that at least one or more conserved cysteines are mutated or disrupted and wherein the polypeptide forms substantially more monomers than a control HCV E2 polypeptide that does not comprise the modified cysteines.

In some embodiments, the modified polypeptide forms at least 40%, at least 50% or at least 60% monomers. Methods for determining or quantifying the proportions of monomer or multimer in a sample are known in the art.

In some embodiments, the modified polypeptide forms at least 40%, at least 45%, at least 50%, at least 55%, at least 60%, at least 65% or at least 70% monomers.

In another embodiment, the present invention provides a modified HCV E2 polypeptide modified such that at least one or more conserved cysteine residues are mutated or disrupted and wherein the polypeptide forms substantially less multimers than a control HCV E2 polypeptide that does not comprise the modified cysteines.

In some embodiments, the modified polypeptide forms less than 70% multimers, or less than 60%, or less than 50% or less than 40% multimers.

In some embodiments, the modified polypeptide forms less than 70% multimers, or less than 65%, or less than 60%, or less than 55%, or less than 50%, or less than 45% or less than 40% multimers.

Reference to 'multimer' includes dimers, trimers, tetramers, dimer-dimers, trimer-dimers, and further oligomers, and high molecular weight aggregates. Typically, disulfide-bonded multimers are dissociated under reducing conditions.

In some embodiments, the invention provides a proteinaceous molecule comprising a modified HCV E2 polypeptide as described herein. In an illustrative embodiment, the protein is a covalent complex comprising E1 and E2 polypeptides or a polyprotein comprising at least E1 and E2 of HCV. In some embodiments, the molecule comprises a heterologous protein or molecule (agent).

In some embodiments, the invention provides a proteinaceous molecule comprising a modified HCV E2 polypeptide as described herein. In an illustrative embodiment, the protein is a complex comprising E1 and E2 polypeptides or a polyprotein comprising at least E1 and E2 of HCV. In some embodiments, the molecule comprises a heterologous protein or molecule.

In some embodiments, the present invention provides a modified HCV polypeptide modified such that one or more of the following conserved cysteines are mutated or disrupted: C581, C585, C652, C677, C494, C486, C459, C452, C564, C597, C569 and C620.

In some embodiments, C581 and/or C585 are mutated or disrupted.

In some embodiments, C652 and/or C677 are mutated or disrupted.

In some embodiments, C486, C452, C564 and C597 are mutated or disrupted.

In some embodiments, C486, C452, C569, and C652 are mutated or disrupted.

In some embodiments, C581, C585, C486, C452, C569, and C652 are mutated or disrupted.

In some embodiments, C581, C585, C486, C452, C569 and C597 are mutated or disrupted.

In some embodiments, C581, C585, C486, C452, C569, C597 and C652 are mutated or disrupted.

Figure 1B:
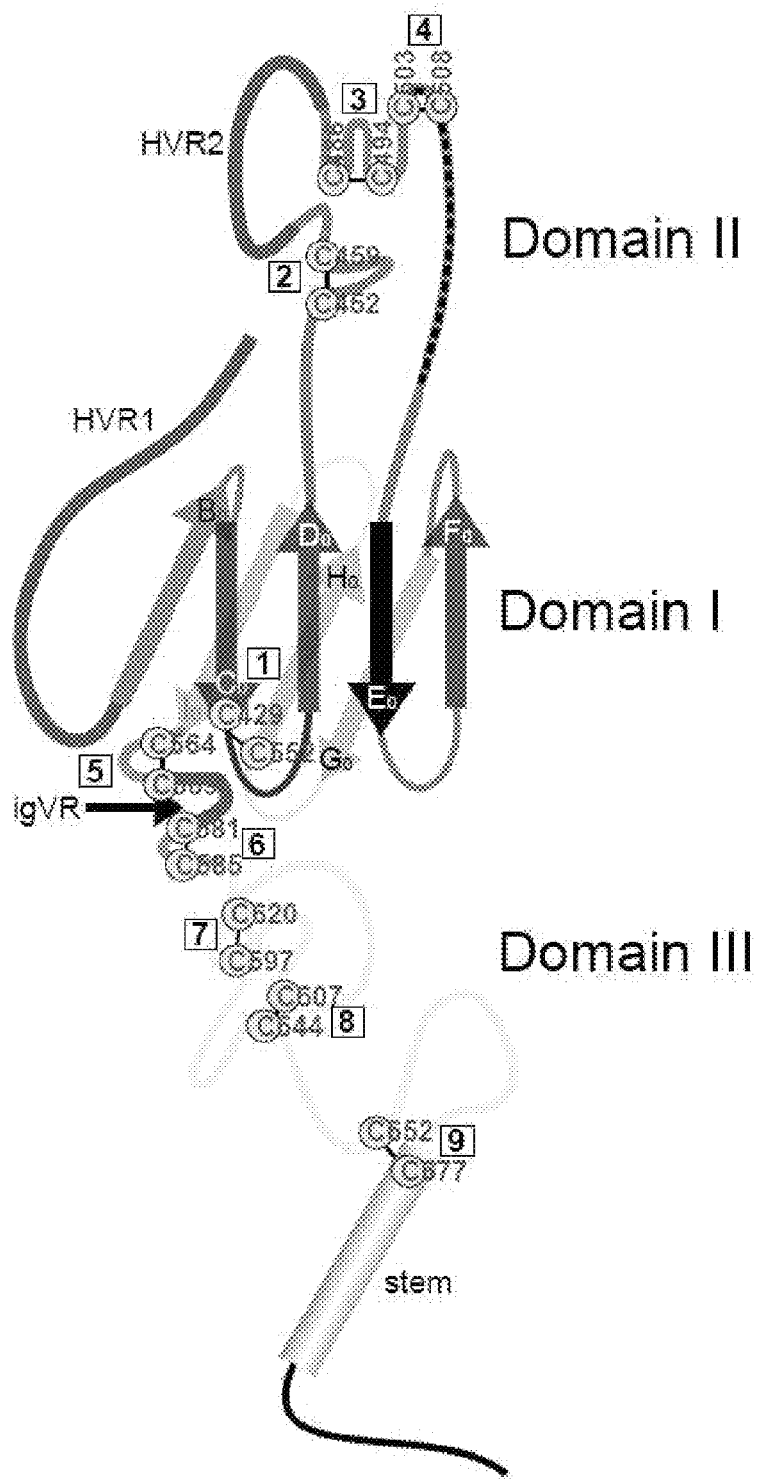

In some embodiments, two cysteine residues are mutated or disrupted at one disulfide within domain III as shown in FIG. 1B. In some embodiments C581 and C585 are mutated and/or C652 and C677 are mutated or disrupted. In some embodiments, C607 and C644 is not mutated or disrupted.

In some embodiments, one or two cysteines are mutated or disrupted at two or more disulfides selected from disulfides 1 to 9.

In some illustrative embodiments, a cysteine at disulfides 2 and 3 are mutated or disrupted. In one exemplified embodiment C452 and C486 are mutated.

In some illustrative embodiments, a cysteine at disulfides 2 and 5 are mutated or disrupted. In one exemplified embodiment C452 and C569 are mutated.

In some illustrative embodiments, a cysteine at disulfides 3 and 5 are mutated or disrupted. In one exemplified embodiment C486 and C569 are mutated.

In some illustrative embodiments, a cysteine at disulfides 2 and 7 are mutated or disrupted. In one exemplified embodiment C452 and C597 are mutated.

In some illustrative embodiments, a cysteine at disulfides 3 and 7 are mutated or disrupted. In one exemplified embodiment C486 and C597 are mutated.

In some illustrative embodiments, a cysteine at disulfides 5 and 7 are mutated or disrupted. In one exemplified embodiment C569 and C597 are mutated.

In some embodiments, a cysteine at two or more of disulfides 2, 3, 5, and 6 are mutated or disrupted. In further embodiments, a cysteine at two or more of disulfides 2, 3, 5, 6 and 7 are mutated or disrupted. In a further embodiment, a cysteine at two or more of disulfides 2, 3, 5, 6, 7 and 9 are mutated or disrupted. In an exemplified embodiment residues C452, C486, C569, C581, C585, C652 and C597 or any combination thereof are mutated.

In some embodiments, a cysteine residue is not mutated or disrupted at one or more of disulfide position 1, 2, 4, 8. In some embodiments, the cysteine not mutated at disulfide 2 is C459. In some embodiments, the cysteine not mutated at disulfide 8 is C607. In some embodiments, a modified HCV E2 polypeptide comprising one or two cysteine mutations at one or more of disulfide positions 1, 2, 4, 8 exhibit one or more of reduced binding to receptor such as CD81, an increased proportion of dimer or multimer or reduced recognition by antibodies that recognise conformation epitopes. Different cysteine mutations have differential effects on E2 polypeptide function as determined herein and based upon the present description, the skilled person can select a cysteine-modified polypeptide that retains conformational capacity such as binding by conformation-sensitive antibody (e.g. H53) and/or receptor binding (such as CD81 binding) and form significantly more monomer than controls without the specific cysteine modification.

In some embodiments disulfides 1, 4, and 8 are not mutated or disrupted.

In some embodiments, modified HCV E2 polypeptides further comprise deletions in one or more variable regions, HVR2, HVR1 and igVR as described in International Publication No. WO 2008/022401 incorporated herein in its entirety by reference.

In some embodiments, the E2 polypeptide has a truncated receptor binding domain, such as $E2_{661}$, lacking a conserved cysteine at the C-terminal end of the polypeptide (C677) or a variant form thereof.

In some embodiments, the modified polypeptide does not exhibit substantially reduced receptor binding relative to a control polypeptide without the modification. In some embodiments, the modified polypeptide exhibits enhanced receptor binding relative to a control E2 polypeptide without the modification. In an illustrative embodiment, receptor binding is CD81 binding, however, the invention extends to modified polypeptide that display a range of receptor binding activities.

In a further embodiment, the modified polypeptide does not exhibit substantially reduced binding by conformational antibodies, such as H53 binding, relative to a control HCV E2 polypeptide that does not have one or more modified cysteines.

In some embodiments the unmodified E2 polypeptide is a truncated receptor binding domain (e.g. amino acids 341-661) of the full length E2 (e.g. amino acids 384-746) lacking a conserved cysteine at the C-terminal end of the polypeptide (C677) or a modified form thereof wherein the modification does not comprise mutation or disruption of a cysteine.

In some embodiments the modified HCV E2 polypeptide comprises one or more detectable or purification tags or markers to facilitate detection or purification.

The present invention is not limited to a particular detection marker and extends to qualitative or quantitative detection using any of the commonly used reporter molecules in detection assays, such as enzymes, fluorophore and radionuclide containing molecules and chemilluminescent molecules.

By 'detection marker' or 'detection tag' is meant a molecule or particle which, by its chemical nature, provides an analytically identifiable signal which allows the detection of an HCV polypeptide. As will be well recognised, a wide variety of different reporter systems are available and those allowing rapid visual detection are clearly the most useful in the context of, for example, point of care diagnostics.

In some embodiments, the detection marker is a visually detectable reporter molecule such as a colloidal particle or microparticle. Colloidal metal and metalloid particles include those comprising gold, silver, platinum, iron, copper, selenium; metal complexes such as cyclopentadienylmanganese (I) tricarbonyl, gold cluster; and microparticles such as latex and dyed latex particles. The detectable modification is conveniently selected from: a fluorescence molecule, a chromogen, a catalyst, an enzyme, a dye such as an infrared dye, a flurochrome, a chemiluminescent, bioluminescent or phosphorescent moiety, a lanthanide ion, a radioisotope or a visual label such as gold or silver nanoparticles. Fluorescent molecules are particularly well established however, this is a rapidly moving field and the present invention is in no way limited to the use of any particular detectable modification. In some embodiments distinguishable compounds such as fluorophores, dyes or particles are used to facilitate combinatorial analyses. In the case of a direct visual label, use may be made of a colloidal metallic or non-metallic particle, a dye particle, bioluminescent enzymes, an enzyme or a substrate, an organic polymer, a latex particle, a liposome, or other vesicle containing a signal producing substance and the like. Especially preferred labels of this type include large colloids, for example, metal colloids such as those from gold, selenium, silver, tin and titanium oxide. In one embodiment in which an enzyme is used as a direct visual label, biotinylated residues are incorporated.

Suitable fluorochromes include, but are not limited to, fluorescein isothiocyanate (FITC), tetramethylrhodamine isothiocyanate (TRITC), R-Phycoerythrin (RPE), and Texas Red. Other exemplary fluorochromes include those discussed by Dower et al. (International Publication WO 93/06121). Reference also may be made to the fluorochromes described in U.S. Pat. No. 5,573,909 (Singer et al), U.S. Pat. No. 5,326,692 (Brinkley et al). Alternatively, reference may be made to the fluorochromes described in U.S. Pat. Nos. 5,227,487, 5,274,113, 5,405,975, 5,433,896, 5,442,045, 5,451,663, 5,453,517, 5,459,276, 5,516,864, 5,648,270 and 5,723,218. Commercially available fluorescent labels include, for example, fluorescein phosphoramidites such as Fluoreprime (Pharmacia), Fluoredite (Millipore) and FAM (Applied Biosystems International), Texas Red, NBD, coumarin, dansyl chloride and rhodamine. Radioactive reporter molecules include, for example, $^{32}P$, which can be detected by an X-ray or phosphoimager techniques.

The present invention extends to qualitative or quantitative detection using any of the commonly used reporter molecules in detection assays known in the art such as enzymes, fluorophores or radionuclide containing molecules, chemilluminescent molecules and binding molecules such as binding pairs. In the case of an enzyme immunoassay, an enzyme is conjugated to a second antibody generally by means of glutaraldehyde or periodate. Commonly used enzymes include horseradish peroxidase, glucose oxidase, beta galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates which yield a fluorescent product rather than the chromogenic substrates listed above. In all cases, the enzyme labelled antibody is added to the first antibody antigen complex, allowed to bind, and the excess reagent is washed away. A solution containing the appropriate substrate is then added to the complex of antibody-antigen antibody. The substrate will react with the enzyme linked to the second antibody, giving a qualitative visual signal, which may be further quantified, usually spectrophotometrically, to give an indication of the amount of antigen which is present in the sample. Alternatively, fluorescent compounds, such as fluorescein and rhodamine are chemically coupled to antibodies without altering their binding capacity. When activated by a illumination with light of a particular wave length, the fluorochrome labelled antibody absorbs the light energy inducing a state of excitability in the molecule followed by emission of the light at a characteristic wavelength visually detectable with a microscope. The term 'binding partner' or 'binding pair' is a reference to complementary molecules which bind or interact with each other via a reversible non-covalent or covalent attachment determined by their structure. Exemplary proteinaceous binding partners include antibody-antigen, enzyme-substrate, biotin-streptavidin, biotin-antibiotin antibodies, digoxigenin-anti-digoxigenin antibodies mannose/maltose/amylose-mannose/maltose/amylose-binding protein and cytokine/chemokine receptor interactions. Other binding relationships are known to those skilled in the art, such as for example those employing glutathione, nickel-chelators and leucine zipper binding pairs (c-Jun and vFos) and any such binding relationship is included herein. Binding pairs may be used in detection and/or purification. Affinity chromatography typically uses binding pairs or ligand substrate interactions to purify a polypeptide of interest.

In another aspect, the present invention provides kits comprising one or more modified HCV E2 polypeptides of the present invention. Kits are contemplated for diagnostic, prognostic, therapeutic or prophylactic applications as well as for use in designing and/or screening for HCV E2 binding molecules or HCV receptor binding molecules.

Accordingly, the present specification provides a diagnostic kit or a solid substrate comprising a composition comprising a hepatitis C virus (HCV) Envelope 2 (E2) polypeptide including a receptor binding variant, wherein the polypeptide is modified to comprise: (i) a cysteine mutated or disrupted at 2, 3, or 4 cysteines selected from C452, C486, C569, and C597; and wherein the polypeptide forms substantially fewer multimers by intermolecular disulfide bonding relative to the HCV E2 polypeptide without cysteine modification. In some embodiments, the polypeptide substantially retains CD81- or H53-binding.

In some embodiments, the polypeptide further comprises a cysteine mutated or disrupted at 1, 2, 3 or 4 of C581, C585, C652 and C677.

In some embodiments, C581 and C585 are mutated or disrupted.

In some embodiments, C652 or C652 and C677 are mutated or disrupted.

In some embodiments, C452, C486, C569, C597, C581 and C585 are mutated or disrupted.

In some embodiments, C452, C486, C569, C597, C581, C585, and C652 are mutated or disrupted.

In some embodiments, the HCV E2 polypeptide is E2661 or a receptor binding portion or variant thereof. In some embodiments, the HCV E2 polypeptide comprises a deletion in 1, 2, or 3 variable regions selected from HVR2, HVR1 and IgVR.

In another aspect, the present invention provides a nucleic acid molecule encoding one or more of the herein disclosed modified HCV E2 polypeptides. In some embodiments, cysteine encoding codons (TGC/T) are deleted or modified to alanine encoding codons (GCT/C) or conservative substitutions such as serine encoding codons (AGT/C) or glycine (GGT/C/A/G), threonine (ACT/C/A/G), tyrosine (TAT/C), glutamine (GAA/G) or asparagine (AGA/G). Alternatively, any other amino acid or a linker sequence may be employed.

In some embodiments, the present invention provides plasmids, expression vectors or other constructs or human or non-human cells (host cells) comprising the subject nucleic acid molecules using art recognised protocol and published nucleic acid sequences or routine modifications thereof.

Accordingly, the present specification enables a host cell or host cell culture comprising a composition comprising a hepatitis C virus (HCV) Envelope 2 (E2) polypeptide including a receptor binding variant, wherein the polypeptide is modified to comprise: (i) a cysteine mutated or disrupted at 2, 3, or 4 cysteines selected from C452, C486, C569, and C597; and wherein the polypeptide forms substantially fewer multimers by intermolecular disulfide bonding relative to the HCV E2 polypeptide without cysteine modification. In some embodiments, the polypeptide substantially retains CD81- or H53-binding.

In some embodiments, the polypeptide further comprises a cysteine mutated or disrupted at 1, 2, 3 or 4 of C581, C585, C652 and C677.

In some embodiments, C581 and C585 are mutated or disrupted. In some embodiments, C652 or C652 and C677 are mutated or disrupted. In some embodiments, C452, C486, C569, C597, C581 and C585 are mutated or disrupted. In some embodiments, C452, C486, C569, C597, C581, C585, and C652 are mutated or disrupted.

In some embodiments, the polypeptide folds as at least 40%, or at least 45%, or at least 50%, or at least 55%, or at least 60%, or at least 65%, or at least 70% monomers.

In some embodiments, the polypeptide folds as less than 70% multimers, or less than 65%, or less than 60%, or less than 55%, or less than 50%, or less than 45% or less than 40% multimers by intermolecular disulfide bonding relative to the HCV E2 polypeptide without cysteine modification.

In some embodiments, the HCV E2 polypeptide is E2661 or a receptor binding portion or variant thereof.

In some embodiments, the HCV E2 polypeptide comprises a deletion in 1, 2, or 3 variable regions selected from HVR2, HVR1 and IgVR.

In another aspect, the present invention provides a method of selecting antibodies or antigen binding fragments thereof or other binding agents, comprising selecting antibodies or agents that bind to one or more of the subject modified HCV E2 polypeptides. In some embodiments, screening methods comprise selection of agents that do not bind to one or more of other subject HCV E2 polypeptides. Thus the invention provides a plurality of HCV E2 polypeptides capable of being used to probe HCV-host cell interactions.

Antibodies may be polyclonal or monoclonal. Further, antibodies may be selected for diagnostic, prognostic, therapeutic, prophylactic, screening or research purposes using criteria known to those of skill in the relevant art.

The terms 'antibody' and 'antibodies' include polyclonal and monoclonal antibodies and all the various forms derived from monoclonal antibodies, including but not limited to full-length antibodies (e.g. having an intact Fc region), antigen-binding fragments, including for example, Fv, Fab, Fab' and F(ab')$_2$ fragments; and antibody-derived polypeptides produced using recombinant methods such as single chain antibodies. The terms 'antibody' and 'antibodies' as used herein also refer to human antibodies produced for example in transgenic animals or through phage display, as well as antibodies, human or humanized antibodies, primatised antibodies or deimmunised antibodies. It also includes other forms of antibodies that may be therapeutically acceptable and antigen-binding fragments thereof, for example single domain antibodies derived from cartilage marine animals or Camelidae, or from libraries based on such antibodies. The selection of fragmented or modified forms of the antibodies may also involve consideration of any affect the fragments or modified forms have on the half-lives of the antibody or fragment.

In another aspect, the present invention provides a method of eliciting an immune response in a subject or patient, the method comprising administering to the subject an effective amount of a modified HCV E2 polypeptide as described herein.

In another aspect, the present invention provides a modified HCV polypeptide or a complex comprising same as described herein for use in the treatment or prevention of HCV infection in a subject.

In another aspect, the present invention provides a modified HCV polypeptide or a complex comprising same as described herein for use in producing an antibody or cellular immune response in a non-human animal subject.

Screening methods are further provided employing one or more of the subject HCV E2 polypeptides. Screening methods involving the subject polypeptides are directed at identifying binding molecules as known in the art. Binding molecules such as antibodies or antigen binding fragments, peptides, peptidomimetic, organic or inorganic molecules are routinely screened using art recognised protocols.

In another embodiment, the present invention also provides a method for producing a protein, the method comprising producing a nucleic acid construct comprising a sequence encoding the HCV E2 polypeptide and capable of directing expression of the polypeptide and introducing same into an expression vector and expressing same in a suitable cell. Proteins are produced by culturing the host cells for a period of time sufficient to allow for expression of the protein in the host cells or, more preferably, secretion of the protein into the culture medium in which the host cells are grown.

Accordingly, in some embodiments, the present specification provides a method of producing a composition comprising at least 40%, or at least 45%, or at least 50%, or at least 55%, or at least 60%, or at least 65%, or at least 70% monomeric HCV E2 polypeptide, the method comprising expressing a polypeptide in a host cell and isolating the expressed product, wherein the polypeptide is an HCV E2 polypeptide including a receptor binding variant, and wherein the polypeptide is modified to comprise: (i) a cysteine mutated or disrupted at 2, 3, or 4 cysteines selected from C452, C486, C569, and C597.

In some embodiments, the polypeptide further comprises a cysteine mutated or disrupted at 1, 2, 3 or 4 of C581, C585, C652 and C677

In some embodiments, C581 and C585 are mutated or disrupted.

In some embodiments, C652 or C652 and C677 are mutated or disrupted.

In some embodiments, C452, C486, C569, C597, C581 and C585 are mutated or disrupted.

In some embodiments, C452, C486, C569, C597, C581, C585, and C652 are mutated or disrupted.

In other embodiments, the invention provides a host cell or cell membrane preparation, virus like particles or proteoliposome, each comprising or encoding an HCV E2 polypeptide of the present invention. Methods for making proteoliposomes are described in the art.

In some embodiments, the cell is a eukaryotic host cell, preferably a yeast, avian, insect, plant or non-human mammalian cells. In other embodiments, the cell is the cell of a subject to be treated.

A 'coding sequence' or a sequence which 'encodes' a selected polypeptide, is a nucleic acid molecule which is transcribed (in the case of DNA) and translated (in the case of mRNA) into a polypeptide in vivo when placed under the control of appropriate regulatory sequences (or 'control elements'). The boundaries of the coding sequence are determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and synthetic DNA sequences. A transcription termination sequence may be located 3' to the coding sequence.

Typical 'control elements', which may be employed to provide expression include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

'Operably linked' refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof.

The term 'recombinant' may be used herein to describe a nucleic acid molecule and means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term 'recombinant' as used with respect to a protein or polypeptide means a polypeptide produced by expression of a recombinant polynucleotide.

'Recombinant host cells,' 'host cells,' 'cells,' 'cell lines,' 'cell cultures,' and other such terms denoting prokaryotic microorganisms or eukaryotic cell lines cultured as unicellular entities, are used interchangeably, and refer to cells which can be, or have been, used as recipients for recombinant vectors or other transfer DNA, and include the progeny of the original cell which has been transfected.

Suitable mammalian cell lines include, but are not limited to, BHK, VERO, HT1080, 293, 293T, RD, COS-7, CHO, Jurkat, HUT, SUPT, C8166, MOLT4/clone8, MT-2, MT-4, H9, PM1, CEM, myeloma cells (e.g., SB20 cells) and CEMX174 are available, for example, from the ATCC).

The synthetic DNA may be recombinantly expressed by molecular cloning into an expression vector containing a suitable promoter and other appropriate transcription regulatory elements, and transferred into prokaryotic or eukaryotic host cells to produce recombinant protein. Techniques for such manipulations are fully described by Sambrook et al., 1989 (supra); Ausubel et al., Current Protocols in Molecular Biology, Green Pub. Associates and Wiley-Interscience, New York, 1988.

For example, a construct for expression in yeast preferably contains a synthetic gene, with related transcriptional and translational control sequences operatively linked to it, such as a promoter (such as GAL10, GALT, ADH1, TDH3 or PGK), and termination sequences (such as the S. cerevisiae ADH1 terminator). The yeast may be selected from the group consisting of: Saccharomyces cerevisiae, Hansenula polymorpha, Pichia pastoris, Kluyveromyces fragilis, Kluyveromyces lactis, and Schizosaccharomyces pombe. See also Yeast Genetics: Rose et al., A Laboratory Course Manual, Cold Spring Harbor Laboratory, Cold Spring Harbor, N.Y., 1990. Nucleic acid molecules can be codon optimised for expression in yeast as known in the art (see Sharp and Cowe, Yeast, 7: 657-678, 1991).

Vectors available for cloning and expression in host cell lines are well known in the art, and include but are not limited to vectors for cloning and expression in mammalian cell lines or yeast (fungal) cells, vectors for cloning and expression in bacterial cell lines, vectors for cloning and expression in phage and vectors for cloning and expression in insect cell lines. The expressed proteins can be recovered using standard protein purification methods.

Translational control elements have been reviewed by M. Kozak (e.g., Kozak, Mamm Genome, 7(8): 563-74, 1996; Kozak, Biochimie., 76(9): 815-21, 1994; Kozak, J Cell Biol, 108(2): 229-241, 1989; Kozak and Shatkin, Methods Enzymol, 60: 360-375, 1979).

Purification can be carried out by methods known in the art including salt fractionation, ion exchange chromatography, gel filtration, size-exclusion chromatography, size-fractionation, and affinity chromatography.

Recombinant glycoproteins can be conveniently prepared using standard protocols as described for example in Sambrook, et al., 1989 (supra), in particular Sections 13, 16 and 17; Ausubel et al., Current Protocols in Molecular Biology, John Wiley & Sons Inc, 1994, in particular Chapters 10 and 16; and Coligan et al., 1995-1997 (supra), in particular Chapters 1, 5 and 6. The polynucleotides may be synthesised by chemical synthesis, e.g., using solution synthesis or solid phase synthesis as described, for example, in Chapter 9 of Atherton and Shephard, Peptide Synthesis. In Nicholson ed., Synthetic Vaccines, published by Blackwell Scientific Publications, and in Roberge et al., Science, 269(5221): 202-204, 1995.

"Subjects" contemplated in the present invention are humans or animals including laboratory or art accepted test or vehicle animals. "Patients" include human subjects in need of treatment or prophylaxis.

The present invention provides methods for producing neutralising antibodies to HCV comprising administering one or more of the subject HCV E2 polypeptides subject and selecting antibodies therefrom that are able to bind to HCV E2 and inter alia block receptor binding. Antibodies are tested, in some embodiments, for their ability to reduce virus infectivity or viral load.

The invention further provides methods of screening for antibodies or other binding agents that specifically bind the subject HCV polypeptide, the method comprising contacting a sample or solution comprising an antibody or other agent with a HCV polypeptide as described herein and determining binding relative to controls. Binding agents are then tested for their therapeutic or prophylactic ability, for example, to reduce infectivity, viral load or transmission.

The present invention contemplates a method of screening, the method comprising contacting a putative interacting compound with an I-ICV E2 polypeptide; and determining binding characteristics of an interaction between the putative interacting compound and the HCV polypeptide or its ability to bind to a receptor, such as CD81.

In another aspect therefore the present specification provides a composition for use in screening for binding agents that prevent host cell entry by hepatitis C virus wherein the composition comprises a hepatitis C virus (HCV) Envelope 2 (E2) polypeptide including a receptor binding variant, wherein the polypeptide is modified to comprise: (i) a cysteine mutated or disrupted at 2, 3, or 4 cysteines selected from C452, C486, C569, and C597; and wherein the polypeptide forms substantially fewer multimers by intermolecular disulfide bonding relative to the HCV E2 polypeptide without cysteine modification, and substantially retains CD81 binding.

In some embodiments, the polypeptide further comprises a cysteine mutated or disrupted at 1, 2, 3 or 4 of C581, C585, C652 and C677.

In some embodiments, C581 and C585 are mutated or disrupted.

In some embodiments, C652 or C652 and C677 are mutated or disrupted.

In some embodiments, C452, C486, C569, C597, C581 and C585 are mutated or disrupted.

In some embodiments, C452, C486, C569, C597, C581, C585, and C652 are mutated or disrupted.

In some embodiments, the polypeptide folds as at least 40%, or at least 45%, or at least 50%, or at least 55%, or at least 60%, or at least 65%, or at least 70% monomers.

In some embodiments, the polypeptide folds as less than 70% multimers, or less than 65%, or less than 60%, or less than 55%, or less than 50%, or less than 45% or less than 40% multimers by intermolecular disulfide bonding relative to the HCV E2 polypeptide without cysteine modification.

In some embodiments, the HCV E2 polypeptide is E2661 or a receptor binding portion thereof.

In some embodiments, the HCV E2 polypeptide comprises a deletion in 1, 2, or 3 variable regions selected from HVR2, HVR1 and IgVR.

The present invention further contemplates a method comprising contacting a sample from a subject with an HCV polypeptide as described herein or a complex comprising same; and determining an interaction between the sample and the HCV E2 polypeptide. In some embodiments, arrays of different E2 polypeptides from different HCV genotypes may be employed. In some embodiments, the sample is a sample comprising antibodies.

In some embodiments, the sample is from an infected subject. Control samples include samples from uninfected individuals. A sample may be from any part of the subject. Convenient samples include blood, serum, plasma, urine, sputum and the like.

Suitable assays are known to those of skill in the art and include ELISA, RIA and EIA-like assays and competitive assays. The subject assays are particularly useful for serosurveillance.

In some embodiments, the kits comprising the subject HCV E2 polypeptides are conveniently used for (or is for use in) diagnosis or prognosis of a viral infection, or pathogen monitoring or serosurveillance kits, optionally including packaging, instructions and various other components such as buffers, substrates, antibodies or ligands, control antibodies or ligands, and detection reagents.

The terms "effective amount" and "therapeutically effective amount" and "prophylactically effective amount" as used herein mean a sufficient amount of the present composition to provide the desired therapeutic, prophylactic or physiological effect. Undesirable effects, e.g. side effects, may sometimes manifest along with the desired therapeutic effect; hence, a practitioner balances the potential benefits against the potential risks in determining an appropriate 'effective amount'. The exact amount of agent required will vary from subject to subject, depending on the species, age and general condition of the subject, mode of administration and the like. Thus, it may not be possible to specify an exact 'effective amount'. However, an appropriate 'effective amount' in any individual case may be determined by one of ordinary skill in the art using routine experimentation. One of ordinary skill in the art would be able to determine the required amounts based on such factors as prior administration of agents, the subject's size, the severity of the subject's symptoms, viral load, and the particular composition or route of administration selected.

The invention provides a method for producing an antibody comprising immunising a non-human animal or screening expression products of a library of human immunoglobulin genes with an HCV polypeptide as described herein, a viral-like particle comprising same or a nucleic acid encoding same and isolating an antibody that binds specifically to the polypeptide or peptide of interest or to all or part of a pathogen comprising same.

In another embodiment, the invention provides an antibody or an antigen-binding fragment produced by the methods described herein using a subject protein, or a human or humanised form thereof. The antibody is preferably monoclonal rather than polyclonal and is preferably, humanised, deimmunised or is a human antibody.

As referred to above, in some embodiments, the present invention contemplates a use of a an HCV polypeptide as described herein or a virus like particle comprising same in the manufacture of a medicament for the treatment or prophylaxis of HCV.

The terms 'treatment' or 'prophylaxis' or 'therapy' are used interchangeably in their broadest context and include any measurable or statistically significant amelioration in at least some subjects in one or more symptoms of HCV or in the risk of developing advanced symptoms of HCV. Prophylaxis may be considered as reducing the severity or onset of a condition or signs of a condition. Treatment may also reduce the severity of existing conditions.

In accordance with these embodiments, the composition is generally administered for a time and under conditions sufficient to elicit an immune response comprising the generation of E2-specific antibodies. The compositions of the present invention may be administered as a single dose or application. Alternatively, the compositions may involve repeat doses or applications, for example the compositions may be administered 2, 3, 4, 5, 6, 7, 8, 9, 10 or more times.

The pharmaceutical composition comprising a subject HCV E2 polypeptide is contemplated to exhibit therapeutic activity when administered in an amount which depends on the particular case. A broad range of doses may be applicable. Considering a human subject, for example, from about 0.1 µg to 1 µg (i.e., including 0.1 µg, 0.2 µg, 0.3 µg, 0.4 µg, 0.5 µg, 0.6 µg, 0.7 µg, 0.8 µg and 0.9 µg) 0.5 µg to 50 µg, 1 µg to 10 µg, 2 µg to 200 µg, 0.1 mg to 1.0 mg (i.e., including 0.1 mg, 0.2 mg, 0.3 mg, 0.4 mg, 0.5 mg, 0.6 mg, 0.7 mg, 0.8 mg and 0.9 mg), from about 15 mg to 35 mg, about 1 mg to 30 mg or from 5 to 50 mg, or from 10 mg to 100 mg of protein may be administered per kilogram of body weight per day or per every other day or per week or per month. Therapeutic including prophylactic compositions may be administered at a dosage of about 0.1 to 20 mg/kg however dosages above or below this amount are contemplated in the ranges set out above. Dosage regimes may be adjusted to provide the optimum therapeutic response. For example, several divided doses may be administered daily, weekly, monthly or other suitable time intervals or the dose may be proportionally reduced as indicated by the exigencies of the situation. It is also possible to administer compositions in sustained release formulations.

Administration is generally for a time and under conditions sufficient to treat or prevent HCV infection. The agents may be administered in a convenient manner such as by the oral, intravenous (where water soluble), intraperitoneal, intramuscular, subcutaneous, intradermal, intrathecal or suppository routes or implanting (e.g. using slow release molecules). Administration may be systemic or local, although systemic is more convenient. References to systemic include intravenous, intraperitoneal, subcutaneous injection, infusion as well as administration via oral, rectal, vaginal and nasal routes or via inhalation which is advantageous. Other contemplated routes of administration are by patch, cellular transfer, implant, sublingually, intraocularly, topically or transdermally. Depending upon the severity or stage of disease and integrity of the blood brain barrier, suitable compositions are required to cross the blood brain barrier.

Pharmaceutical compositions are conveniently prepared according to conventional pharmaceutical compounding techniques. See, for example, Remington's Pharmaceutical Sciences, 18th Ed., Mack Publishing, Company, Easton, Pa., U.S.A., 1990. The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g. intravenous, oral or parenteral.

A 'pharmaceutically acceptable carrier' and/or a diluent is a pharmaceutical vehicle comprised of a material that is not otherwise undesirable i.e., it is unlikely to cause a substantial adverse reaction by itself or with the active agent. Carriers may include all solvents, dispersion media, coatings, antibacterial and antifungal agents, agents for adjusting tonicity, increasing or decreasing absorption or clearance rates, buffers for maintaining pH, chelating agents, membrane or barrier crossing agents. A pharmaceutically acceptable salt is a salt that is not otherwise undesirable. The agent or composition comprising the agent may be administered in the form of pharmaceutically acceptable non-toxic salts, such as acid addition salts or metal complexes, For oral administration, the compounds can be formulated into solid or liquid preparations such as capsules, pills, tablets, lozenges, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. Tablet may contain a binder such as tragacanth, corn starch or gelatin; a disintegrating agent, such as alginic acid; and a lubricant, such as magnesium stearate. If desired, tablets may be sugar-coated or enteric-coated by standard techniques. The active agent can be encapsulated to make it stable to passage through the gastrointestinal tract. See for example, International Patent Publication No. WO 96/11698.

For parenteral administration, the composition may be dissolved in a carrier and administered as a solution or a suspension. When the agents are administered intrathecally, they may also be dissolved in cerebrospinal fluid. For transmucosal or transdermal (including patch) delivery, appropriate penetrants known in the art are used for delivering the antagonist. For inhalation, delivery uses any convenient system such as dry powder aerosol, liquid delivery systems, air jet nebulizers, propellant systems. For example, the formulation can be administered in the form of an aerosol or mist. The agents may also be delivered in a sustained delivery or sustained release format. For example, biodegradable microspheres or capsules or other polymer configurations capable of sustained delivery can be included in the formulation. Formulations can be modified to alter pharmacokinetics and biodistribution. For a general discussion of pharmacokinetics, see, e.g., Remington's Pharmaceutical Sciences, 1990 (supra). In some embodiments the formulations may be incorporated in lipid monolayers or bilayers such as liposomes or micelles. Targeting therapies known in the art may be used to deliver the agents more specifically to certain types of cells or tissues.

The actual amount of active agent administered and the rate and time-course of administration will depend on the nature and severity of the disease. Prescription of treatment, e.g. decisions on dosage, timing, etc. is within the responsibility of general practitioners or specialists and typically takes into account the condition of the individual patient, the site of delivery, the method of administration and other factors known to practitioners. Examples of techniques and protocols can be found in Remington's Pharmaceutical Sciences, 1990 (supra).

Sustained-release preparations that may be prepared are particularly convenient for inducing immune responses. Examples of sustained-release preparations include semipermeable matrices of solid hydrophobic polymers containing the polypeptide, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers, and poly-D-(−)-3-hydroxybutyric acid. While polymers such as ethylene-vinyl acetate and lactic acid-glycolic acid enable release of molecules for over 100 days, certain hydrogels release proteins for shorter time periods. Liposomes may be used which are of the small (about 200-800 Angstroms) unilamellar type in which the lipid content is greater than about 30% cholesterol, the selected proportion being adjusted for the optimal therapy.

Stabilization of proteins may be achieved by modifying sulfhydryl residues, lyophilizing from acidic solutions, controlling moisture content, using appropriate additives, and developing specific polymer matrix compositions. The in vivo half life of proteins may be extended using techniques known in the art, including, for example, by the attachment of other elements such as polyethyleneglycol (PEG) groups. Prime-boost immunisation strategies as disclosed in the art are clearly contemplated. See for example International Publication No. WO/2003/047617. Thus, compositions may be in the form of a vaccine, priming or boosting agent.

The term 'isolated' means material that is substantially or essentially free from components that normally accompany it in its native state. For example, an 'isolated nucleic acid molecule', as used herein, refers to a nucleic acid or polynucleotide, isolated from the sequences which flank it in a naturally-occurring state, e.g., a DNA fragment which has been removed from the sequences that are normally adjacent to the fragment. Alternatively, an 'isolated polypeptide' and the like, as used herein, refer to in vitro isolation and/or purification of a protein from its natural cellular environment, and from association with other components of the cell. Without limitation, an isolated nucleic acid, polynucleotide, peptide, or polypeptide can refer to a native sequence that is isolated by purification or to a sequence that is produced by recombinant or synthetic means.

By 'effective amount,' in the context of treatment or prophylaxis of HCV is meant the administration of that amount of active to a subject, either in a single dose or as part of a series or slow release system that is effective for producing a therapeutic effect, in some subjects. The effective amount will vary depending upon the health and physical condition of the subject and the taxonomic group of individual to be treated, the formulation of the composition, the assessment of the medical situation, and other relevant factors. It is expected that the amount will fall in a relatively broad range that can be determined through routine trials.

Reference to functional variants include those that are distinguished from a naturally-occurring form or from forms presented herein by the addition, deletion and/or substitution of at least one amino acid residue. Thus, variants include proteins derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are generally biologically active, that is, they continue to possess one or more desired biological activity of the native protein (e.g., CD81 and H53 binding or equivalent markers of conformational capability excluding viral entry). Furthermore, variants are selected which continue to show enhanced monomer formation and less multimer formation. Variants may result from, for example, genetic polymorphism or from human manipulation. Biologically active variants of a viral polypeptide will typically have at least 40%, 50%, 60%, 70%, generally at least 75%, 80%, 85%, preferably about 90% to 95% or more, and more preferably about 98% or more sequence similarity or identity with the amino acid sequence for the polypeptide described herein as determined by sequence alignment programs described elsewhere herein using default parameters. A biologically active variant of a polypeptide may differ from that polypeptide generally by as much 100, 50 or 20 amino acid residues or suitably by as few as 1-15 amino acid residues, as few as 1-10, such as 6-10, as few as 5, as few as 4, 3, 2, or even 1 amino acid residue. The cysteine amino acid numbering designations may change if the amino acid sequence changes. However, the linear order of cysteines provides a workable reference point for the skilled person and all such variants are encompassed.

A variant polypeptide may be altered in various ways including amino acid substitutions, deletions, truncations, and insertions. Methods for such manipulations are generally known in the art. For example, amino acid sequence variants of a polypeptide can be prepared by mutations in the DNA as described in Example 9. Methods for mutagenesis and nucleotide sequence alterations are well known in the art. See, for example, Kunkel, *Proc. Natl. Acad. Sci. USA,* 82: 488-492, 1985; Kunkel et al., *Methods in Enzymol.,* 154: 367-382, 1987; U.S. Pat. No. 4,873,192; Watson et al., *Molecular Biology of the Gene, Fourth Edition*, Benjamin/Cummings, Menlo Park, Calif., 1987) and the references cited therein. Guidance as to appropriate amino acid substitutions that do not affect biological activity of the protein of interest may be found in the model of Dayhoff et al., *Atlas of Protein Sequence and Structure*, Natl. Biomed. Res. Found., Washington, D.C., 1978. Conservative substitutions, such as exchanging one amino acid with another having similar properties, are desirable as discussed in more detail below.

Variant polypeptides may contain conservative amino acid substitutions at various locations along their sequence, as compared to the reference amino acid sequence. A 'conservative amino acid substitution' is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as 'small' since their side chains are not sufficiently large, even if polar groups are lacking, to confer hydrophobicity. With the exception of proline, 'small' amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g., PAM120 matrix and PAM250 matrix as disclosed for example by Dayhoff et al., 1978, (supra), A model of evolutionary change in proteins. Matrices for determining distance relationships In Dayhoff, (ed.), *Atlas of protein sequence and structure*, National Biomedical Research Foundation, Washington D.C., Vol. 5, pp. 345-358; and by Gonnet et al., *Science,* 256(5062): 1443-1445, 1992, however, include proline in the same group as glycine, serine, alanine and threonine. Accordingly, for the purposes of the present invention, proline is classified as a 'small' amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further sub-classified as cyclic or noncyclic, and aromatic or nonaromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always nonaromatic. Dependent on their structural properties, amino acid residues may fall in two or more classes. For the naturally-occurring protein amino acids, subclassification according to this scheme is presented in the Table 3.

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional polypeptide can readily be determined by assaying its activity. Conservative substitutions are shown in Table 4 (below) under the heading of exemplary substitutions. More preferred substitutions are shown under the heading of preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity, such as CD81 or H53 binding.

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, *Biochemistry, third edition*, Wm.C. Brown Publishers, 1993.

Thus, a predicted non-essential amino acid residue in a polypeptide is typically replaced with another amino acid residue from the same side chain family. Alternatively, mutations can be introduced randomly along all or part of a polynucleotide coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined.

Accordingly, the present invention also contemplates variants of polypeptides provided herein or their biologically-active fragments, wherein the variants are distinguished from the provided sequences such as SEQ ID NO: 2 or 4 by the addition, deletion, or substitution of one or more amino acid residues. In general, variants will display at least about 30, 40, 50, 55, 60, 65, 70, 75, 80, 85, 90, 91, 92, 93, 94, 95, 96, 97, 98, 99% similarity to a reference polypeptide sequence. Desirably, variants will have at least 30, 40, 50, 55, 60, 65, 70, 75, 80, 85, 90, 91, 92, 93, 94, 95, 96, 97, 98, 99% sequence identity to a parent polypeptide sequence. Moreover, sequences differing from the disclosed sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100 or more amino acids but which retain the biological activity of the parent polypeptide are contemplated. The sequences set out in SEQ ID NOs: 2 and 4 include alanine substitutions for cysteines as compared to SEQ ID NOs: 1 and 3, respectively. Alanine may be substituted by other non-cysteine amino acids as understood in the art such as serine, valine, glycine, threonine, tyrosine, glutamine, asparagine, leucine or isoleucine.

In some embodiments, variant polypeptides differ from a parent polypeptide by at least one but by less than 50, 40, 30, 20, 15, 10, 8, 6, 5, 4, 3 or 2 amino acid residue(s). In another, variant polypeptides differ from the recited sequence by at least 1% but less than 20%, 15%, 10% or 5% of the residues. (If this comparison requires alignment the sequences should be aligned for maximum similarity. 'Looped' out sequences from deletions or insertions, or mismatches, are considered differences.) The differences are, suitably, differences or changes at a non-essential residue or a conservative substitution.

A 'non-essential' amino acid residue is a residue that can be altered from the wild-type sequence of an embodiment polypeptide without abolishing or substantially altering one or more of its functional activities as described herein. Suitably, the alteration does not substantially alter one of these activities, for example, the binding activity is at least 60%, 70% or 80% of the parent. An 'essential' amino acid residue is a residue that, when altered from the herein disclosed polypeptide, results in abolition of an activity of the parent molecule such that less than 60% of the parent binding activity is present.

In other embodiments, a variant polypeptide includes an amino acid sequence having at least about 50%, 55%, 60%, 65%, 70%, 75%, 80%, 85%, 90%, 91%, 92%, 93%, 94% 95%, 96%, 97%, 98% or more similarity to a corresponding sequence of a parent HCV E2 polypeptide comprising the amino acid sequence set out in SEQ ID NO: 2 or 4.

The present invention is further described by the following non-limiting Examples. Materials and methods used in the Examples are provided below.

Cell lines and antibodies. HEK 293T and Huh7 cells were maintained in Dulbecco's minimal essential medium supplemented with 10% fetal calf serum and 2 mM l-glutamine (DMF10). MAb H53 and A4 were kind gifts from Jean Dubuisson. Immunoglobulin 14 (IgG14) was purified from plasma obtained from an HIV-infected individual using protein G sepharose (GE Healthcare) according to the manufacturers instructions. MAb H53 has been reported to recognize a native epitope within E2 and coprecipitates non-covalently associated E1. This epitope is also independent of known CD81-binding sites and provides a broader screen for native conformational characteristics within E2. The human conformation sensitive monoclonal antibodies CBH 4B, 4D, and 4G specific to immunogenic domain A were a generous gift from Steven Foung (Keck et al., 2004 (supra)). MAb 183 is a mouse monoclonal antibody specific to the HIV-1 capsid protein available form the NIH AIDS Research and Reference Reagent Bank. MAb24 is a monoclonal antibody that recognizes a linear epitope within E2 (res 411-423). Rabbit polyclonal antibodies directed against the six-histidine epitope tag (anti-HIS, Rockland Biochemicals), fluorescence-conjugated anti-rabbit (IR-800, Rockland), fluorescence-conjugated anti-mouse (Alexa680, Invitrogen) and HRP-conjugated antibodies (DAKO) are all commercially available.

Expression vectors. The pcDNA4HisMax (Invitrogen)-based vector containing E1E2 sequences derived from the H77c genotype 1a, pE1E2, has been previously described (Drummer et al. *FEBS Lett* 546: 385-90, 2003). The HIV-1 luciferase reporter vector pNL4-3.LUC.R–E– was obtained from N. Landau through the NIH AIDS Research and Reference Reagent program. In vitro mutagenesis was performed by standard overlap extension PCR to introduce cysteine (TGC/T) to alanine (GCT/C) substitutions. The inserted DNA sequences were confirmed using Big-Dye terminator chemistry and ABI automated sequencing. The pcDNA3 (Invitrogen)-based vector containing sequences encoding a truncated E2 protein (polyprotein residues 384 and 661) downstream of a tissue plasminogen activator leader sequence has also been described ($pE2_{661}$). Mutant $E2_{661}$-his sequences were amplified from the corresponding pE1E2 vectors using PCR primers to introduce a C-terminal six-histidine epitope tag as well as NheI and XbaI restriction sites for insertion into $pE2_{661}$. All vectors were transfected into HEK 293T cells using Fugene 6 (Roche) according to the manufacturer's instructions.

Radioimmunoprecipitation (RIP) and Western blotting. Radiolabelling of E1E2-HIV-1 pseudotyped particles was performed in 293T cells seeded at $3.5\times10^5$ cells per well in six-well tissue-culture dishes and cotransfected with 1 ug each of pNL43.LUC.R⁻E⁻ plus either pE1E2 or empty pcDNA4HisMax vector as previously described. 24 hrs post-transfection, the tissue-culture media was replaced with 75 uCi Trans[35]S-label (ICN, Costa Mesa, Calif.) in cysteine- and methionine-deficient DMF10 for 18 hrs. The tissue-culture fluid was clarified and then subject to centrifugation at 14,000×g for 2hrs at 4° C. The virus pellet was lysed in RIP lysis buffer (0.6M KCl, 0.05M Tris, pH 7.4, 1 mM EDTA, 0.02% sodium azide) and immunoprecipitated with MAb H53 and IgG14 or MAb183 prior to non-reducing sodium dodecyl sulfate-polyacrylamide gel electrophoresis (SDS-PAGE) and radioisotope imaging. E2 as detected by MAb H53 was quantified using ImageQuant software (GE Healthcare). The intracellular expression of E1E2 was also determined by lysis of the remaining cell monolayer with Western lysis buffer (PBS pH 7.4 containing 1% Tx 100, 1 mM EDTA), SDS-PAGE analysis and transfer to nitrocellulose membrane and detected using MAbA4 (anti-E1) and MAb24 (anti-E2) and a fluorescently conjugated goat anti-mouse Alexa 680 antibody (Invitrogen). Immunoblots were imaged using a fluorescent scanner (Odyssey; LI-COR).

Radiolabelling of secreted $E2_{661}$-his was performed using 293T cells seeded at $3.5\times10^5$ cells/well in six-well tissue-culture dishes (Nunc) and transfected with 2 ug of $pE2_{661}$ or the empty pcDNA3 vector as previously described. 24 hrs post-transfection, the cells were treated with cysteine- and methionine-deficient DMF10 (MP Biomedicals) for 30 mins prior to addition of 75 uCi Trans[35]S-label (ICN, Costa Mesa, Calif.) for 1 h and then transferred into serum-reduced media (OptiMEM, Invitrogen) for 6 h. The tissue culture fluid was clarified by centrifugation at 14,000×g for 10 mins and immunoprecipitated with MAb H53 or anti-HIS antibodies prior to SDS-PAGE analysis and radioisotope imaging. Expression of unlabelled $E2_{661}$ for CD81-binding assays was performed by transfection of 293T cells as described above. Twenty-four hours post-transfection, the tissue-culture fluid was transferred into OptiMEM and harvested every 24 h for 72 h. The clarified tissue-culture fluid was concentrated approximately 10-fold prior to reducing SDS-PAGE and transfer of proteins to nitrocellulose membrane. Expression of $E2_{661}$-his was normalized by immunoblotting with anti-HIS (Rockland) and the fluorescence-conjugated IR-800 antibody (Rockland) Immunoblots were analysed using an Odyssey LI-COR fluorescent scanner and quantification software.

E1E2-pseudotyped HIV-1 particle (HCVpp) entry assay. Pseudotyped particle entry assays were performed as previously described (Drummer et al. 2003 (supra)). HEK 293T cells were cotransfected with 1 ug each of pNL43.LUC.R–E– plus either pE1E2 or empty pcDNA4HisMax vector. At 72 hrs post-transfection, culture supernatants were filtered (0.45 µM) and applied in triplicate to Huh7 monolayers seeded at $3\times10^4$/well in 48-well tissue-culture dishes(Nunc). At 72 h post-infection, Huh7 cells were lysed and measured for luciferase activity using the Promega luciferase substrate system and a Fluostar (BMG Labtechnologies) fitted with luminescence optics.

Solid-phase binding assays: CD81-LEL binding and GNA-lectin capture. The expression and purification of a chimera composed of maltose-binding protein (MBP) linked to the CD81 large extracellular loop (LEL) between residues 113 to 201 (MBP-LEL[113-201]) has been previously described (Drummer et al., *Biochem Biophys Res Commun* 328: 251-257, 2005; Drummer et al., *J Virol* 76: 11143-7, 2002). This dimeric form of the CD81-LEL has been used to extensively characterize E2-CD81 interactions and has been shown to be an excellent mimic of native CD81 and can interact with first extracellular loop (EC1) of Claudin-1 (Harris et al., *J Biol Chem* 285: 21092-102, 2010). In addition, it reflects the homodimers observed in crystal structures of hCD81-LEL as well as the homotypic interactions between cell-associated full-length CD81. The L441M mutation within the E2 CD81-binding site was also included as a control for non-specific binding. The binding of lysed HCVpp to MBP-LEL[113-201] has also been previously described (Drummer et al., 2006 (supra)). Briefly, 96-well enzyme-linked immunosorbant assay (Nunc Maxisorb) plates were coated with 5 ug/mL of dimeric MBP-LEL[113-201] in PBS overnight. Any uncoated sites were blocked using PBS containing 10 mg/mL of bovine serum albumin solution ($BSA_{10}PBS$) prior to washing with PBS containing 0.05% Tween-20 (PBST). The HCVpp lysates were normalized for monomeric E2 content as detected by RIP with MAb H53 and applied to immobilised MBP-LEL[113-201] at serial two-fold dilutions in PBST containing 5 mg/mL BSA ($BSA_5PBST$). Bound E2 was detected by MAb H53 and rabbit anti-mouse immunoglobulin-horseradish peroxidase (HRP) conjugate (DAKO). This E2-antibody complex was developed using tetramethylbenzidine (TMB) substrate according to the manufacturer's instructions (Sigma).

To assay binding of $E2_{661}$-his proteins to MBP-LEL[113-201], total secreted $E2_{661}$-his was first normalized for monomeric E2 content as detected by Western blotting with anti-HIS (Rockland) as described above. The $E2_{661}$-his proteins were then applied to the MBP-LEL[113-201] coated EIA plates at serial two-fold dilutions. Bound E2 was detected using anti-HIS and goat anti-rabbit immunoglobulin-HRP conjugate (DAKO) and developed with TMB. As a protein loading control, EIA plates were also coated with lectin derived from Galanthus nivalis Agglutinin (GNA-lectin, Sigma) at 0.5mg/mL in PBS. Uncoated sites were blocked with $BSA_{10}PBS$ prior to $E2_{661}$-his proteins being applied across the plate at the same starting concentration used for the CD81-binding assay. Bound E2 was detected by anti-HIS applied across the plate at serial two-fold dilutions in BSA$_5$PBST and an anti-rabbit HRP-conjugated antibody. All binding was measured as a function of absorbance at 450 nm (with 620 nm subtraction) using a Fluostar fitted with absorbance optics and calculated as a percentage of maximal WT binding.

Lectin-affinity purification of E2$_{661}$-his and blue-native PAGE analysis. E2$_{661}$-his proteins were expressed and metabolically-labelled as described above. The clarified tissue-culture fluid was bound to GNA-lectin conjugated agarose beads (Vector Laboratories) overnight at 4° C. The tissue-culture fluid was removed and the remaining beads washed in PBS. Any bound proteins were eluted in 2-bead volumes of 1M mannose for 1 hr at 4° C. A fraction of the eluent was subject to reducing SDS-PAGE analysis and radioisotope imaging to quantify relative expression using ImageQuant software (GE Healthcare). The normalized proteins were then analysed by 4-16% blue-native PAGE at 4° C. according to Wittig et al., Nat Protoc 1: 418-28, 2006. 5 ug of purified thyroglobulin (660 kDa), ferritin (880/440), aldolase (158), conalbumin (75) and ovalbumin (45) (GE Healthcare) were used as size-standard markers. Non-covalently associated, dimeric MBP-LEL[113-201] (110 kDa) was also used as a control for native conditions. The Coomassie stained markers were marked with radiolabelled material prior to radioisotope imaging. Total E2$_{661}$-his and the proportion of each different species was quantified using ImageQuant software (GE Healthcare).

Sequences. The following sequences were synthetically constructed for expression in mammalian systems. A synthetic gene encoding the E2 protein fragment (residues 384-661; strain H77c) was constructed by Geneart AG (Regensburg, Germany). The human trypsinogen signal peptide (MNPLLILTFVAAALA) was appended in-frame to the N-terminus of E2 mature protein in order to facilitate secretion of the mature polypeptide into the expression medium. A Kozak sequence was introduced just before the N-terminus to increase translational initiation and a (His)$_6$ sequence was added in-frame to enable subsequent purification of the secreted proteins by immobilised metal affinity chromatography. Two stop codons were added after the His-tag at the C-terminus to ensure efficient translational termination. The codon usage of the E2-his cDNA was adapted to the codon bias of Homo sapiens genes. A Kpn1 I restriction site at the 5' end of the cDNA and a Xho I restriction site was introduced at the 3' end in order to ligate the GeneartcDNA into pcDNA3 and pcDNA 3.1 plasmids (Invitrogen). The DNA encoding these sequences were verified by big dye terminator sequencing.

```
>WT E2661
                                             (SEQ ID NO: 1)
MNPLLILTFVAAALAETHVTGGNAGRTTAGLVGLLTPGAKQNIQLINTN

GSWHINSTALNCNESLNTGWLAGLFYQHKFNSSGCPERLASCRRLTDFA

QGWGPISYANGSGLDERPYCWHYPPRPCGIVPAKSVCGPVYCFTPSPVV

VGTTDRSGAPTYSWGANDTDVFVLNNTRPPLGNWFGCTWMNSTGFTKVC

GAPPCVIGGVGNNTLLCPTDCFRKHPEATYSRCGSGPWITPRCMVDYPY

RLWHYPCTINYTIFKVRMYVGGVEHRLEAACNWTRGERCDLEDRDRSEH

HHHHH
```

```
>WT E2661 M + C597A
                                             (SEQ ID NO: 2)
MNPLLILTFVAAALAETHVTGGNAGRTTAGLVGLLTPGAKQNIQLINTN

GSWHINSTALNCNESLNTGWLAGLFYQHKFNSSGAPERLASCRRLTDFA

QGWGPISYANGSGLDERPYAWHYPPRPCGIVPAKSVCGPVYCFTPSPVV

VGTTDRSGAPTYSWGANDTDVFVLNNTRPPLGNWFGCTWMNSTGFTKVC

GAPPAVIGGVGNNTLLAPTDAFRKHPEATYSRAGSGPWITPRCMVDYPY

RLWHYPCTINYTIFKVRMYVGGVEHRLEAACNWTRGERADLEDRDRSEH

HHHHH
```

```
>Δ123 E2661
                                             (SEQ ID NO: 3)
MNPLLILTFVAAALAETHQNIQLINTNGSWHINSTALNCNESLNTGWLA

GLFYQHKFNSSGCPERLASCGSSGCWHYPPRPCGIVPAKSVCGPVYCFT

PSPVVVGTTDRSGAPTYSWGANDTDVFVLNNTRPPLGNWFGCTWMNSTG

FTKVCGAPPCGSSGCPTDCFRKHPEATYSRCGSGPWITPRCMVDYPYRL

WHYPCTINYTIFKVRMYVGGVEHRLEAACNWTRGERCDLEDRDRSEHHH

HHH
```

```
>Δ123 E2661 M + C597A
                                             (SEQ ID NO: 4)
MNPLLILTFVAAALAETHQNIQLINTNGSWHINSTALNCNESLNTGWLA

GLFYQHKFNSSGAPERLASCGSSGAWHYPPRPCGIVPAKSVCGPVYCFT

PSPVVVGTTDRSGAPTYSWGANDTDVFVLNNTRPPLGNWFGCTWMNSTG

FTKVCGAPPAGSSGAPTDAFRKHPEATYSRAGSGPWITPRCMVDYPYRL

WHYPCTINYTIFKVRMYVGGVEHRLEAACNWTRGERADLEDRDRSEHHH

HHH
```

Expression of proteins. For nickel affinity purification, proteins were expressed in FreeStyle™ 293-F cells (Invitrogen) cultured in FreeStyle™ Expression Medium (Invitrogen) supplemented with penicillin/streptomycin/fungizone (Invitrogen). All cells were maintained at 37° C. in humidified incubators with an atmosphere of 8% $CO_2$. Transient expression of each of the proteins was carried out in FreeStyle™ 293-F cells by transfection with the pcDNA3.1-based expression plasmids and 293fectin transfection reagent (Invitrogen) according to the manufacturer's instructions. The cells in a total volume of 180 ml were transfected at a final concentration of $1 \times 10^6$ viable cells/ml and incubated in a sterile shaker flask (Corning) for 5 days on an orbital shaker (IKA) rotating at 150 rpm in a 37° C. humidified incubator with an atmosphere of 8% $CO_2$. Twenty-four hours after transfection the cell cultures were supplemented with Tryptone N1 (Organotechnie, France) to a final concentration of 0.5% v/v. Typically the cell cultures were harvested 5 days after transfection. Protein expression was examined by electrophoresis of a sample of cell culture supernatant using 4-20% Tris-Glycine SDS polyacrylamide gel and the proteins visualised by staining with Coomassie Blue reagent. For protein purification, cell culture supernatants were harvested by centrifugation at 2500 rpm and then passed through a 0.45 μM filter (Nalgene) prior to chromatography.

Nickel affinity purification. Following filtration the cell culture supernatants were subjected to immobilised metal affinity chromatography (IMAC) using Nickel sepharose to purify the wild type and variant E2-his proteins. The purification procedure is described below:

1. Buffers: Ni-MAC Buffer A (50 mM NaH2PO4 pH 8.0, 300 mMNaCl, 10 mM imidazole). Ni-MAC Buffer B (Elution) (50 mM NaH2PO4 pH 8.0, 300 mMNaCl, 500 mM imidazole).

2. Protocol: Procedures 2 to 6 were carried out at 4-8° C. 1 ml Ni Sepharose 6 Fast Flow resins (GE Healthcare) in a 10 ml Poly-Prep columns (Bio-Rad) were washed with 5 volumes of ddH2O. The columns were equilibrated with 10 ml Ni-MAC Buffer A. Samples were loaded onto the columns, and break-through (B/T) collected. The columns were washed with 10 ml Ni-MAC Buffer A. The proteins were eluted with 5 ml Ni-MAC Buffer B (Elution) and 1 ml fractions collected. Peak fractions were identified using 96-well plate format Bradford Assay and Coomassie-stained SDS-polyacrylamide gel electrophoresis (SDS-PAGE) gels. Peak fractions were pooled and dialysed in 1× PBS overnight at 4° C. Following dialysis protein concentrations were determined using 96-well plate format Bradford Assay and 1 mg/ml BSA for a standard curve.

Gel filtration chromatography. A Superdex 200 column (PC3.2/30) was equilibrated in S buffer (0.3M NaCl, 0.1M TrisHCl, 1 mM EDTA, 0.02% Azide, pH 8.0). Approximately 300 μg of protein was loaded and run at 0.5 ml/min and the absorbance monitored at 280 nm.

Antibodies. The epitope recognised by monoclonal antibody 24 (MAb 24) is specific to a conserved epitope located between residues 411-428 of E2. The epitope recognised by monoclonal antibody 44 (MAb 44) is specific to an epitope located between residues 512-529 of the genotype 1 E2 sequence. The epitope recognised by MAb 53 is conformation dependent {Deleersnyder, 1997 #288}.

Immunoprecipitation. Radiolabelling of secreted E2661-his was performed using 293T cells seeded at $3.5 \times 10^5$ cells/well in six-well tissue-culture dishes (Nunc) and transfected with 2 μg of pE2661 or the empty pcDNA3 vector as described herein. 24 hrs post-transfection, the cells were incubated in cysteine- and methionine-deficient DMF10 (MP Biomedicals) for 30 mins prior to addition of 100 μCi Trans$^{35}$S-label (ICN, Costa Mesa, Calif.) for 4 h and then transferred into serum-reduced media (OptiMEM, Invitrogen) for 18 h. The tissue culture fluid was clarified by centrifugation at 14,000×g for 10 mins and immunoprecipitated with MAb H53 antibodies prior to SDS-PAGE analysis and radioisotope imaging.

EXAMPLE 1

Individual Cysteine Disulfide Substitution Mutations in the Context of the Full-length E2 Glycoprotein Coexpressed with E1

Figure 2A:
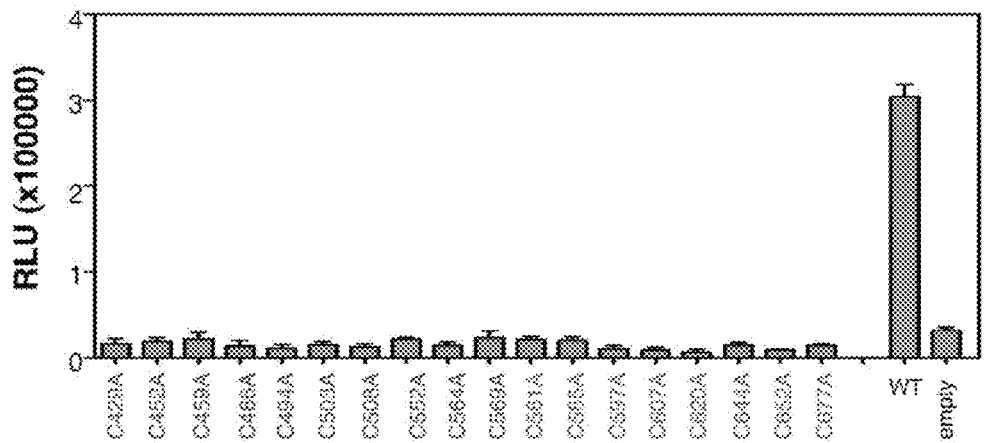
FIG. 2A through C illustrate individual cysteine to alanine mutations in glycoprotein E2 have diverse effects on E2 folding and function in HCVpp. A. Entry into Huh7 cells as mediated by E1E2-pseudotyped HIV-1 virus (HCVpp) containing E2 glycoproteins with individual cysteine to alanine substitution mutations. Entry of HCVpp into Huh7 cells is measured as a function of relative luciferase units (RLU). B. Maturation and incorporation into HCVpp by E2 glycoproteins containing individual cysteine to alanine substitution mutations. Non-reducing SDS-PAGE analysis of HCVpp radioimmunoprecipitated using the anti-E2 conformation-dependent MAb H53 as an indicator of E2 folding, maturation and non-covalent heterodimerization with E1. Controls for uniform HCVpp production (p24) as well as intracellular expression and processing of E1 and E2 determined in western blots of transfected cell lysates are also shown. The percentage CD81 binding at a ¼ dilution of HCVpp derived from FIG. 2C is shown (Bottom). C. Binding of HCVpp containing E2 glycoproteins with individual cysteine to alanine substitution mutations to the large extracellular loop (LEL) of CD81. Binding of HCVpp containing individual Cys-to-Ala mutations to MBP-LEL$^{113-201}$ as detected by MAb H53. The L441M mutation within the E2 CD81-binding site represents a control for non-specific interactions.
Figure 2B:
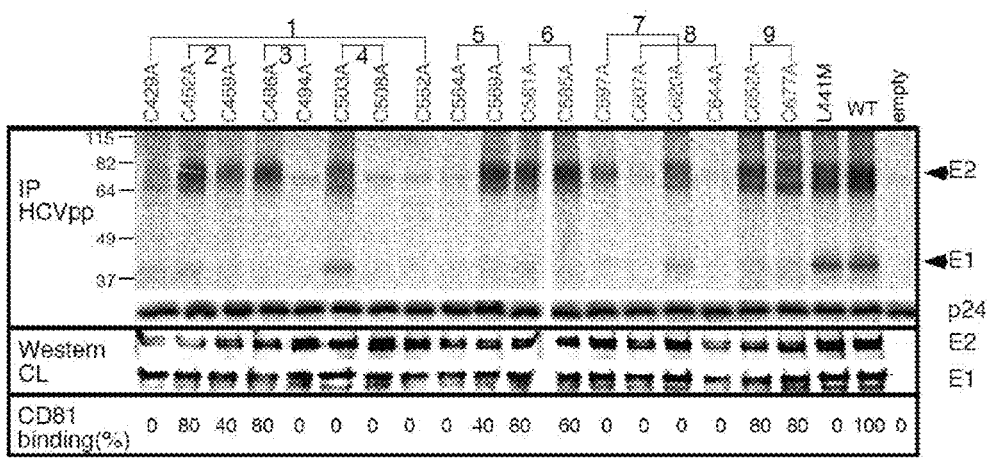

The assignment of disulfides in relation to the domain structure of E2, as proposed by Krey et al., 2010 (supra), is shown in FIG. 1 and Table 2. The effects of substituting individual cysteines to alanine on E2 folding and function were assessed in the context of E1E2 derived from the genotype 1a isolate H77c in HCVpp. The Cys-to-Ala substitutions abolished the ability of HCVpp to infect Huh7 hepatoma cells, indicating that the 9 disulfides of E2 are critical for cellular entry competence (FIG. 2A). Western blot analysis of transfected cell lysates with MAb H52 (directed to E2) and MAb A4 (directed to E1) indicated that E1 and E2 were expressed at wild-type levels (FIG. 2B). However, the use of a conformation-dependant E2 specific MAb, 1453, in immunoprecipitations of biosynthetically labelled HCVpp revealed that the mutations had caused defects in the glycoprotein complex.

Figure 2C:
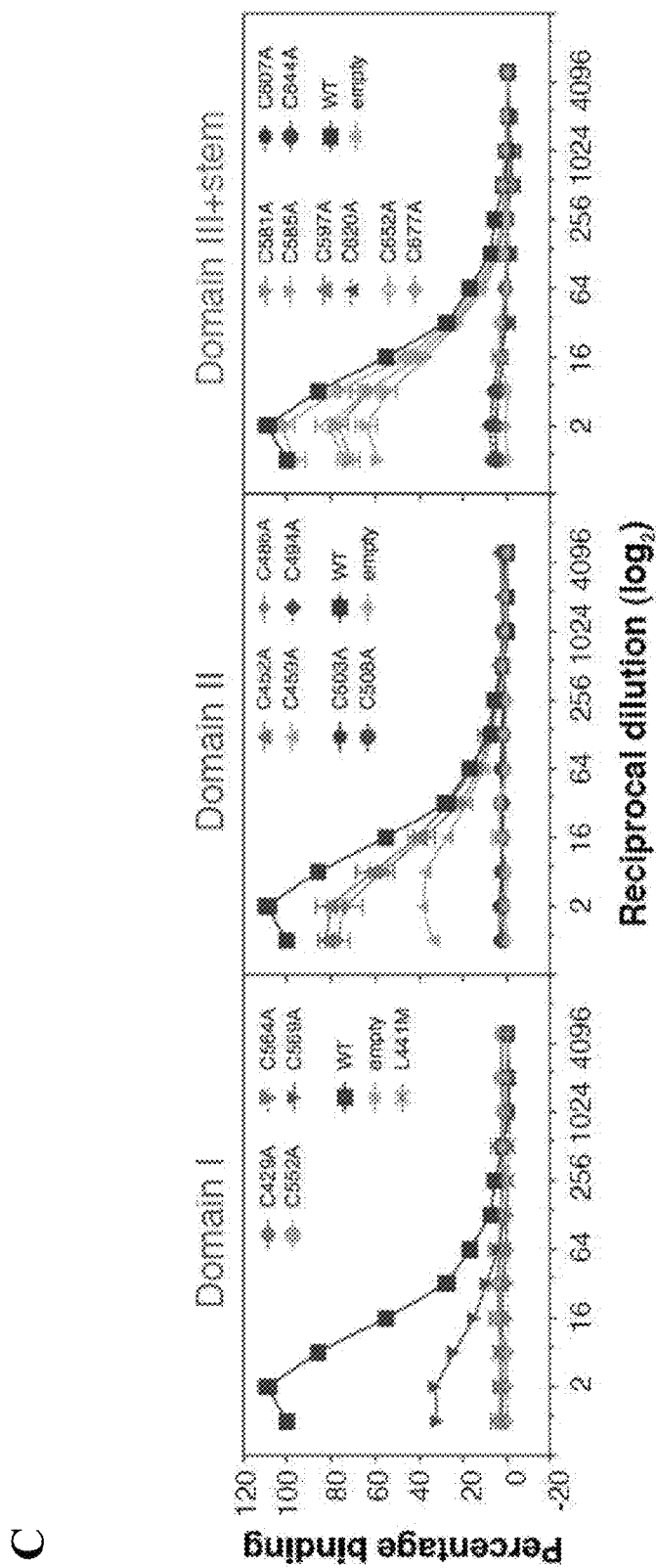

Domain I. Little or no HCVpp-associated E2 was immunoprecipitated by H53 for the disulfide 1 mutants C429A and C552A, respectively, consistent with folding and/or virion incorporation defects. A solid-phase CD81-binding assay utilizing a recombinant form of the CD81 large extracellular loop (LEL) fused to maltose binding protein (MBP-LEL$^{113-201}$), revealed the absence of LEL-binding activity for both mutants (FIG. 2C). These data are consistent with the proposed role of C429 and C552 in forming a long-range disulfide within the central beta-sandwich of domain I. The mutation of C564 and C569, which form disulfide 5 at the base of domain I, resulted in discordant effects on E2 folding and function with H53-reactive E2 obtained for C569A but not for C564A. Despite the incorporation of C569A into HCVpp, this mutant failed to heterodimerize with E1 and exhibited a 70%-reduction in CD81 binding ability (FIG. 2C).

Domain II comprises disulfides 2 (C452-C459), 3 (C486-C494), and 4 (C503-C508) formed by relatively short-range bonding between adjacent cysteine residues. The C452A mutant (disulfide 2) incorporated wild-type levels of E2 into HCVpp, whereas its counterpart, C459A, had a notable reduction in H53-reactive E2; both mutants failed to heterodimerize with E1. Reduced CD81-binding function was also observed: 80% for C452A and 40% for C459A. The C486A mutant (disulfide 3) was incorporated into HCVpp at WT levels whereas its disulfide-bonding partner, C494A, was absent. The C486A mutant failed to heterodimerize with E1 but retained ~80% of WT LEL-binding activity. The mutation of disulfide 4 cysteines also led to discordant effects with H53-reactive E2 in association with E1 being obtained for C503A but not for C508A. Both mutants lacked CD81-binding function.

Domain III comprises disulfides 6 (C581-C585), 7 (C597-C620) and 8 (C607-C644), and is connected to the stem region via disulfide 9 (C652-C677). The participation of C597 and C620 in forming disulfide 7 has not been confirmed and is therefore putative (Krey et al., 2010 (supra)). Whereas H53-reactive E2 was obtained from HCVpp at wild-type levels for C581A and C585A (disulfide 6), these mutants failed to heterodimerise with E1 and exhibited a 20-40% reduction in CD81-binding. For the putative disulfide 7, C597A led to a significant reduction in H53-precipitable E2, whereas C620A presented as an E1E2 complex; both mutants lacked LEL-binding function. The disulfide 8 mutations, C607A or C644A, were not tolerated, as H53 reactive E2 was not detected in HCVpp. Finally, while both C652A and C677A (disulfide 9) were incorporated into HCVpp at wild-type levels, they exhibited a reduction in heterodimerization with E1. Both mutants, however, retained substantial CD81 binding, consistent with their location adjacent to (C652) or within (C677) the E2 stem, which is distal to the CD81 binding region and domain III.

EXAMPLE 2

Simultaneous Mutagenesis of Cysteine Pairs Involved in Disulfide Formation

Figure 3A:
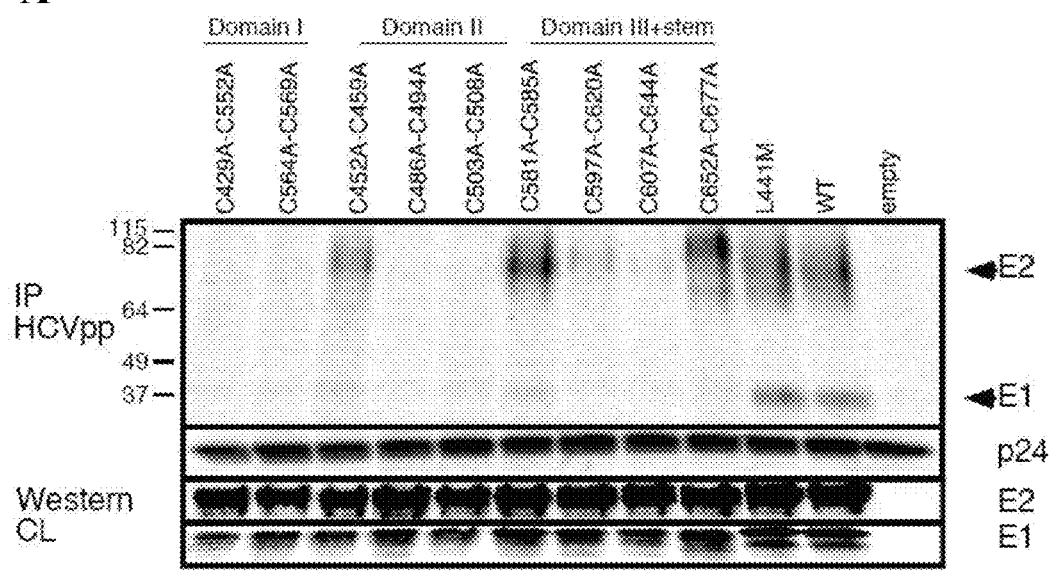
FIG. 3A through B illustrate the role of the proposed disulfide pairs in glycoprotein E2 within HCVpp. A. Maturation and incorporation into HCVpp by E2 glycoproteins containing pair-wise cysteine to alanine substitution mutations. Non-reducing SDS-PAGE analysis of HCVpp radioimmunoprecipitated with the anti-E2 conformation-dependent MAb H53 as an indicator of E2 folding, maturation and non-covalent heterodimerization with E1. Controls for HCVpp production (p24) and intracellular expression and processing of E1 and E2 determined in western blots of transfected cell lysates are also shown. B. Binding of HCVpp containing E2 with pair-wise cysteine to alanine substitution mutations to the large extracellular loop (LEL) of CD81. Binding of HCVpp containing pair-wise Cys-to-Ala mutations to MBP-LEL$^{113-201}$ as detected by MAb H53. The L441M mutation within the E2 CD81-binding site represents a control for non-specific interactions.
Figure 3B:
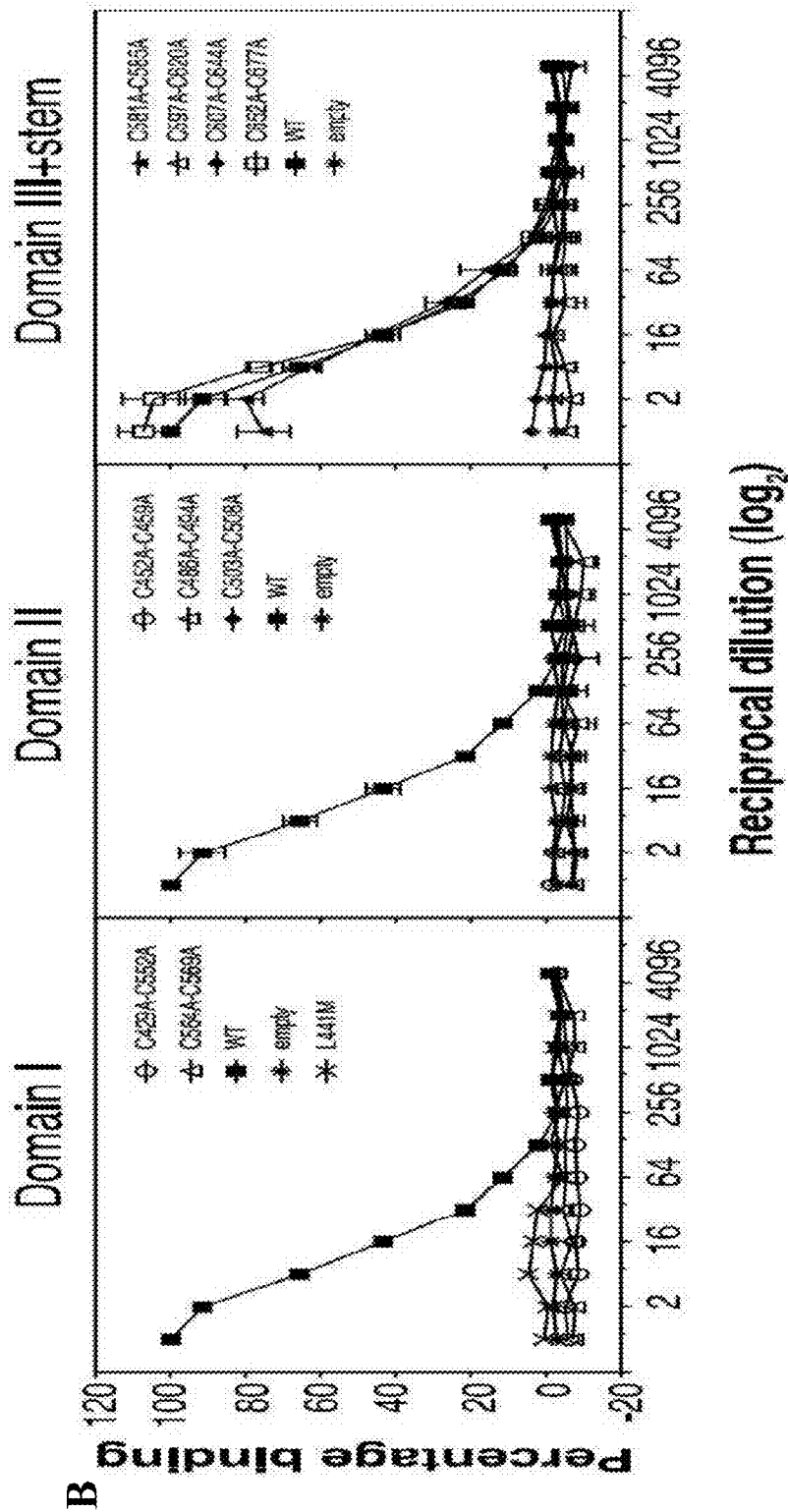

A Cys-to-Ala scan of the HIV envelope glycoprotein gp120/gp41 complex revealed that mutations of individual cysteines did not favour a functional protein fold, whereas simultaneous Ala substitutions rescued both folding and function in two of ten disulfides (van Anken et al., *Mol Biol Cell* 19:4298-309, 2008). To alleviate the tendency for protein misfolding due to the presence of unpaired cysteines simultaneous Ala-replacement of each disulfide pair was undertaken. The intracellular expression and polyprotein processing to E1 and E2 was confirmed for the double Cys-to-Ala mutants by western blotting (FIG. 3A), however HCVpp entry activity was absent (data not shown). The incorporation of H53-reactive E2 into HCVpp was observed for C452A/C459A (Domain II), C581A/C585A and C652A/C677A (Domain III), the latter failing to heterodimerize with E1 (FIG. 3A). In these three cases, the component single mutants were also incorporated into HCVpp (see FIG. 2B). Of these three mutants, C581A/C585A and C652A/C677A retained CD81 binding activity (FIG. 3B). An H53-reactive E2 protein associated with HCVpp was not observed for the other double mutants. These data indicate that 2 disulfides within domain III, C581-C585 and C653-C677, are not required for efficient E2 glycoprotein incorporation into HCVpp and CD81-binding function. These data also indicate that the functional defects associated with particular Cys-to-Ala mutations are not alleviated by removal of the unpaired Cys following substitution of the disulfide-bonding partner.

EXAMPLE 3

Individual Cysteine and Pair-wise Disulfide Substitution Mutations in the Truncated E2 Glycoprotein (E2$_{661}$-his)

Figure 4A:
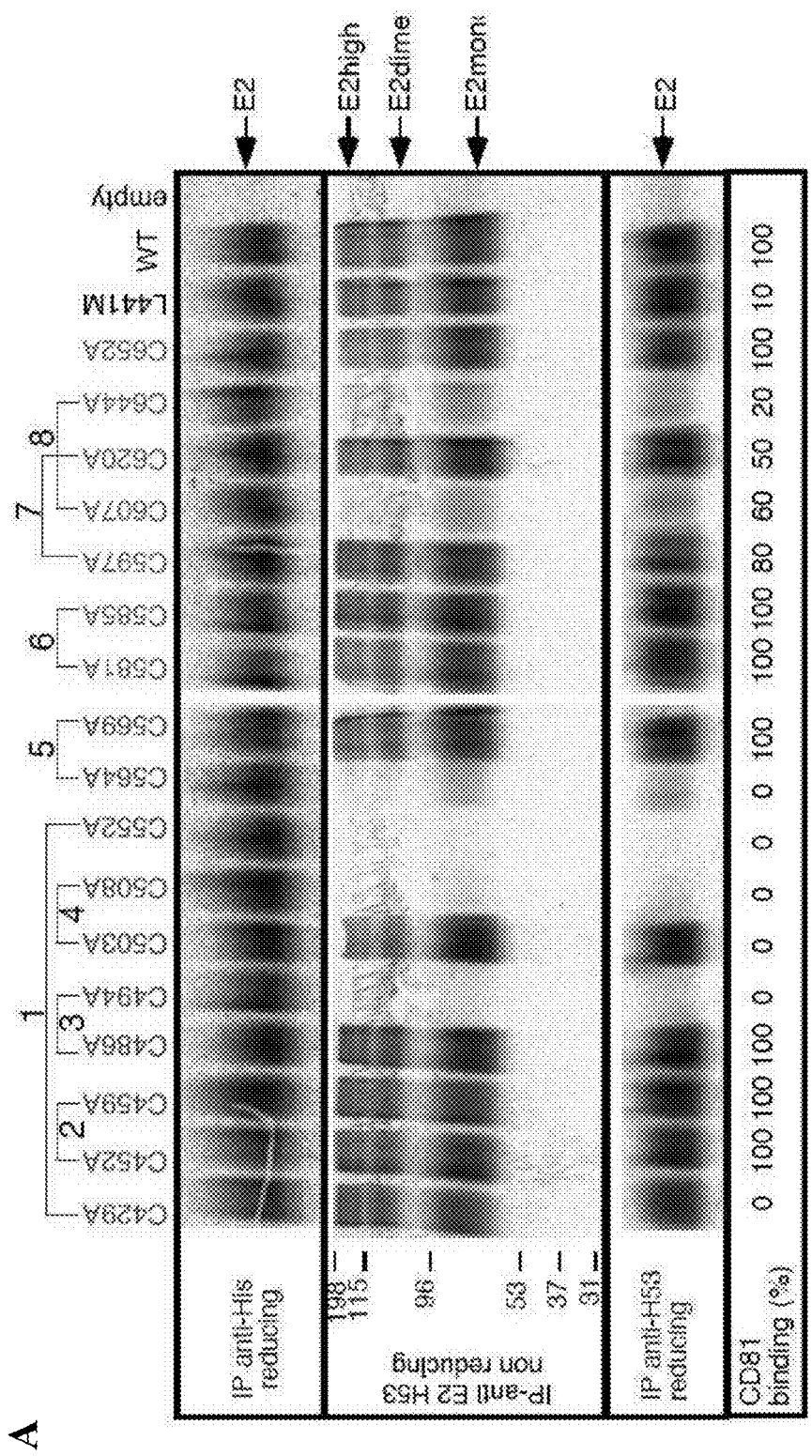
FIG. 4A through B illustrates individual cysteine to alanine mutations in glycoprotein E2 have diverse effects on E2 folding and function in $E2_{661}$-his. A. Expression, secretion and folding of $E2_{661}$-his proteins containing individual cysteine to alanine substitution mutations. SDS-PAGE analysis of radiolabelled, secreted $E2_{661}$-his containing individual cysteine to alanine immunoprecipitated with anti-HIS (top panel) or anti-E2 conformation-dependent MAb H53 under non-reducing (middle) and reducing (second bottom) conditions. The migration of monomeric (E2mono), dimeric (E2dimer) and higher molecular mass forms (E2high) of $E2_{661}$-his under non-reducing conditions is indicated. The percentage CD81 binding at a ¼ dilution of $E2_{661}$-his derived from FIG. 4B is shown (Bottom) B. Binding to CD81-LEL by $E2_{661}$-his proteins containing individual cysteine to alanine substitution mutations. Binding of secreted $E2_{661}$-his containing single Cys-to-Ala mutations to MBP-LEL$^{113-201}$ as detected by rabbit anti-his antibody. The L441M mutation within the E2 CD81-binding site represents a control for non-specific interactions. Loading controls for the same $E2_{661}$-his proteins are also shown (right panel) as captured by lectin and detected by anti-HIS.

The effects of Cys-to-Ala mutations were next assessed in the context of the receptor-binding domain of E2 (residues 384-661, E2$_{661}$-His), which folds independently of E1, retains the three domain architecture described by Krey et al., 2010 (supra) and retains CD81 and SRB1 binding functions. All mutants were secreted from transfected 293T cells at wild type levels, as indicated by immunoprecipitation of metabolically labelled proteins with anti-His antibody via the C-terminal hexa-His tag (FIG. 4A, top panel). The MAb H53-reactivity profile of all but one of the E2$_{661}$-His mutants largely reflected that observed for the corresponding E1E2 mutants (FIG. 4A, 2$^{nd}$ and 3$^{rd}$ panel and see FIG. 2B). Thus, Cys residues that are essential for H53 reactivity include C494, C508 (DII), C552, C564 (DI), C607 and C644 (DIII), whereas C452, C459, C486, C503 (DII), C569, C581, C585 (DI), C597, C620, and C652 (DIII) are dispensable for this function (FIG. 4A, 2$^{nd}$ and 3$^{rd}$ panel). The C429A mutant was an outlier, as H53 binding was not altered in the context of E2$_{661}$-His but recognition by H53 was reduced in virion-incorporated E1E2. An examination of the H53-reactive mutants by SDS-PAGE under non-reducing conditions (FIG. 4A, second panel) revealed a ladder of bands corresponding to monomer (~60-80 kDa), dimer (~100-110 kDa) and higher-order species, which were also observed for wild type.

Figure 4B:
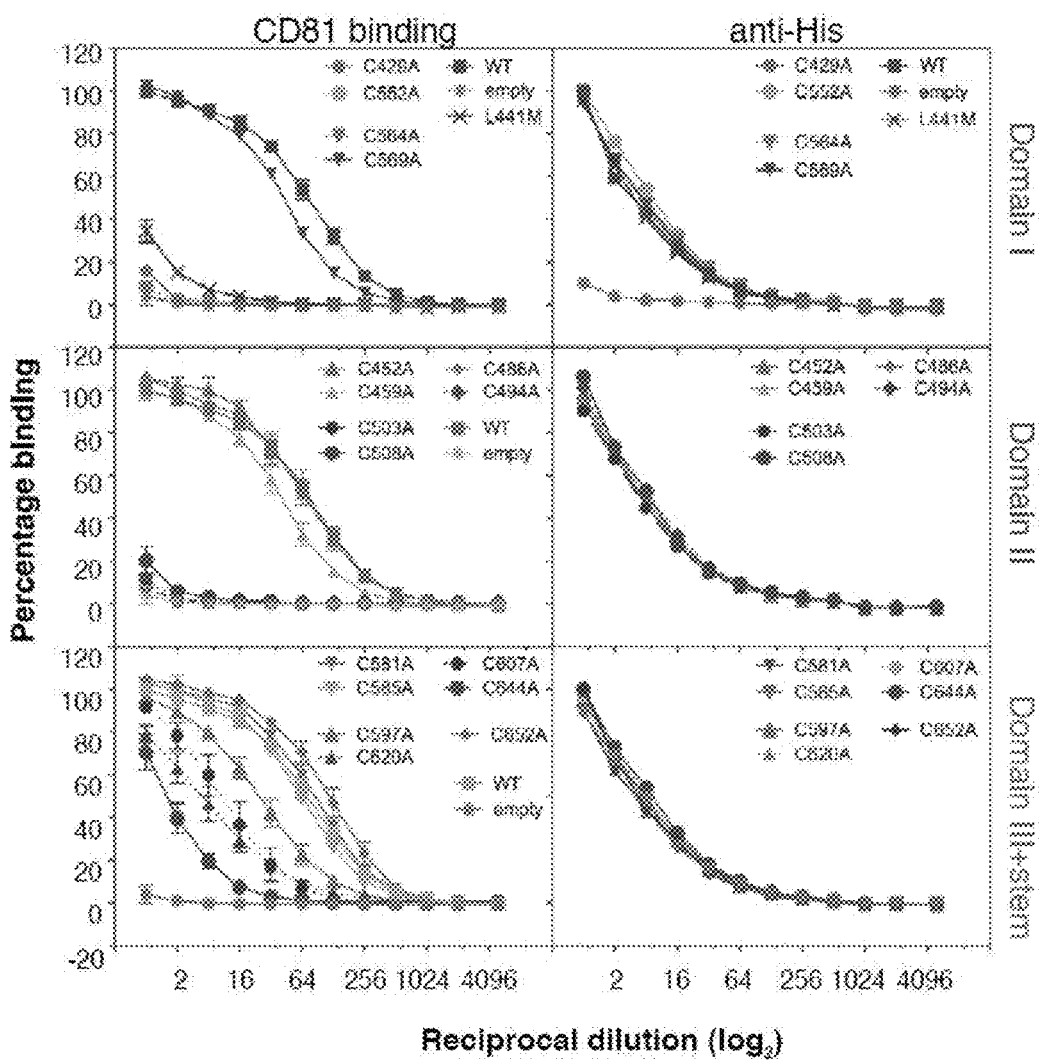

The presence of the C-terminal hexa-His tag in E2$_{661}$-His enabled CD81 LEL binding activity to be assessed independently of H53 reactivity (FIG. 4A, bottom panel; FIG. 4B). Three patterns of LEL reactivity relative to H53 reactivity were discerned when the Cys-to-Ala mutants were considered according to disulfide pairing: (1) Loss of H53 reactivity following Ala-substitution of at least 1 Cys of a disulfide pair predicted a decrease in or loss of LEL-binding function for both mutants: C429-C552 (DI) and C503-C508 (DII); (2) The level of H53 reactivity following Ala-substitution of either Cys contributing to a disulfide predicted the level of LEL-binding function for both mutants: C581-C585 (DIII), C452-C459 (DII), C597-C620 (DIII) and C607-C644 (DIII); (3) One cysteine within a disulfide pair was dispensable for H53 and CD81 reactivity while the other was essential for these functions: C569 (disulfide 5, DI) and C486 (disulfide 3, DII) are not required for acquisition of the H53 fold or CD81 binding function. Mutation of the free Cys at 652 did not affect H53 or CD81-LEL binding suggesting that this residue is dispensable for the E2$_{661}$ fold.

EXAMPLE 4

Mutation of Disulfide Pairs in the E2 Receptor-binding Domain (E2$_{661}$)

Figure 5A:
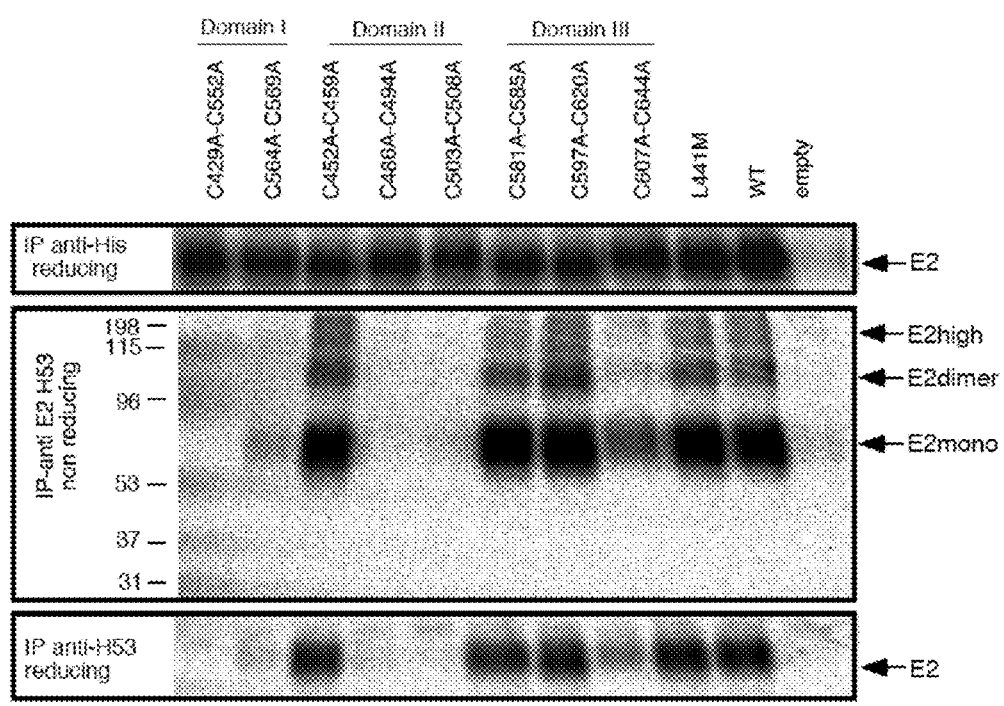
FIG. 5A through C illustrates the role of proposed disulfides in folding and function in $E2_{661}$-his. A. Expression, secretion and folding of $E2_{661}$-his proteins containing pair-wise cysteine to alanine substitution mutations. SDS-PAGE analysis of radiolabelled, secreted $E2_{661}$-his containing cysteine to alanine mutations of the proposed disulfide pairs immunoprecipitated with anti-HIS (top panel) or anti-E2 conformation-dependent MAb H53 under non-reducing (middle) and reducing (bottom) conditions. The migration of monomeric (E2mono), dimeric (E2dimer) and higher molecular mass forms (E2high) of $E2_{661}$-his under non-reducing conditions is indicated. B. Binding to CD81-LEL by $E2_{661}$-his proteins containing individual cysteine to alanine substitution mutations. Binding of secreted $E2_{661}$-his containing pair wise Cys-to-Ala mutations of the proposed disulfides to MBP-LEL$^{113-201}$ as detected by rabbit anti-His antibody. The L441M mutation within the E2 CD81-binding site represents a control for non-specific interactions. Loading controls for the same $E2_{661}$-his proteins are also shown (right panel) as captured by lectin and detected by anti-HIS. C. Conformational changes within domain A. Selected mutants were assessed for their ability to be detected by conformation sensitive antibodies specific to immunogenic domain A (Keck et al., J Virol 78: 9224-32, 2004). Radiolabelled $E2_{661}$-his proteins were immunoprecipitated with the indicated MAbs and examined under non-reducing conditions.
Figure 5B:
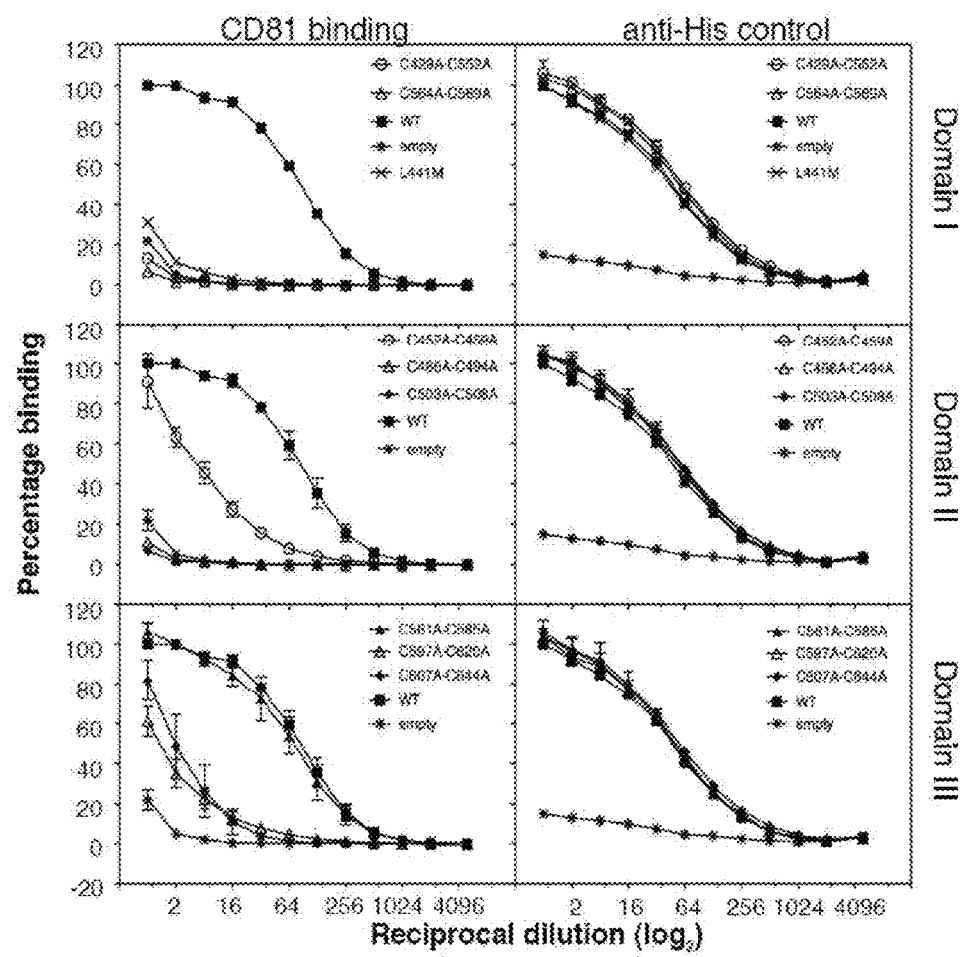
Figure 5C:
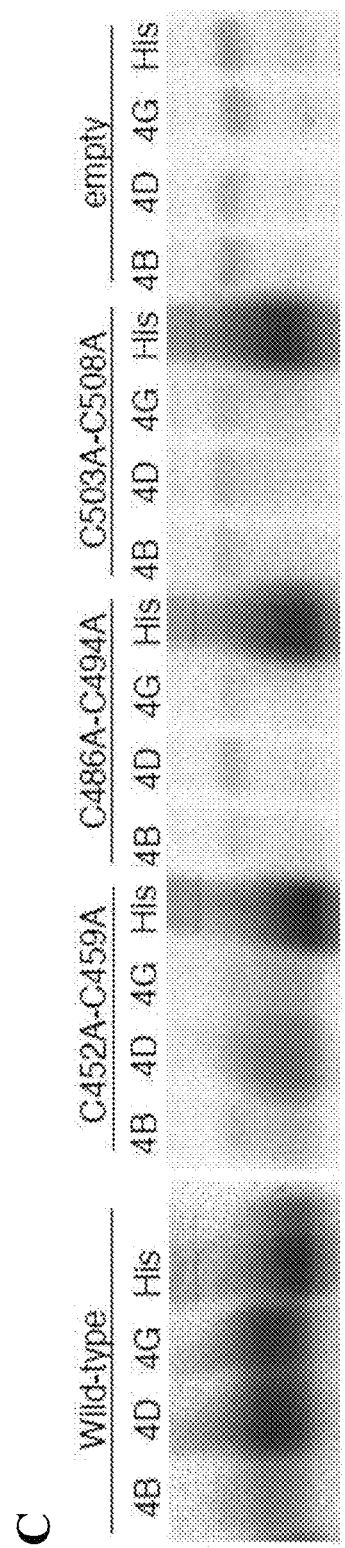

The presence of an unpaired cysteine within single Cys-to-Ala E2$_{661}$-his mutants could lead to misfolded protein due to the formation of non-native disulfides. Therefore, it was determined whether or not simultaneous Ala replacement of Cys residues participating in disulfide formation could rescue the phenotype of defective single Cys-to-Ala mutants in the context of E2$_{661}$-His. The MAb H53 and LEL reactivity of C452A/C459A, C581A/C585A, C597A/C620A and C607A/C644A was retained, although the CD81-LEL binding activity of the double mutants tended to be lower than that of the component single mutants (FIG. 5A, B). Notably, the single component mutations of C452A/C459A had WT CD81-LEL binding function but the double mutant retained only 40% of this activity. By contrast, the combination of single Cys-to-Ala mutations associated with loss of LEL binding function by one or both component cysteines [C429A/C552A (DI), C564A/C569A (DI), C486A/C494A (DII) and C503A/C508A (DID] did not restore function. The conformation-dependant MAbs, CBH-4B, -4D and -4G were used to probe the conformation of domain II mutants. FIG. 5C shows that MAb reactivity was markedly decreased (CBH-4B and -4G for C452A/C459A, 40% LEL binding) or absent (C486A/C494A and C503A/C508A) indicating that the double mutations had altered the conformation of domain II. These data show that disulfides 1 and 5 (DI) and disulfides 3 and 4 (DII) are essential for maintenance of a WT fold and LEL binding activity while disulfides 2 (DII), 7 and 8 (DIII) are not strictly required but contribute to H53 and LEL binding activity. By contrast, C581A/C585A (DIII) is dispensable for these functions.

EXAMPLE 5

Multiple Free Cysteines Tolerated Within the E2 Fold

Figure 6A:
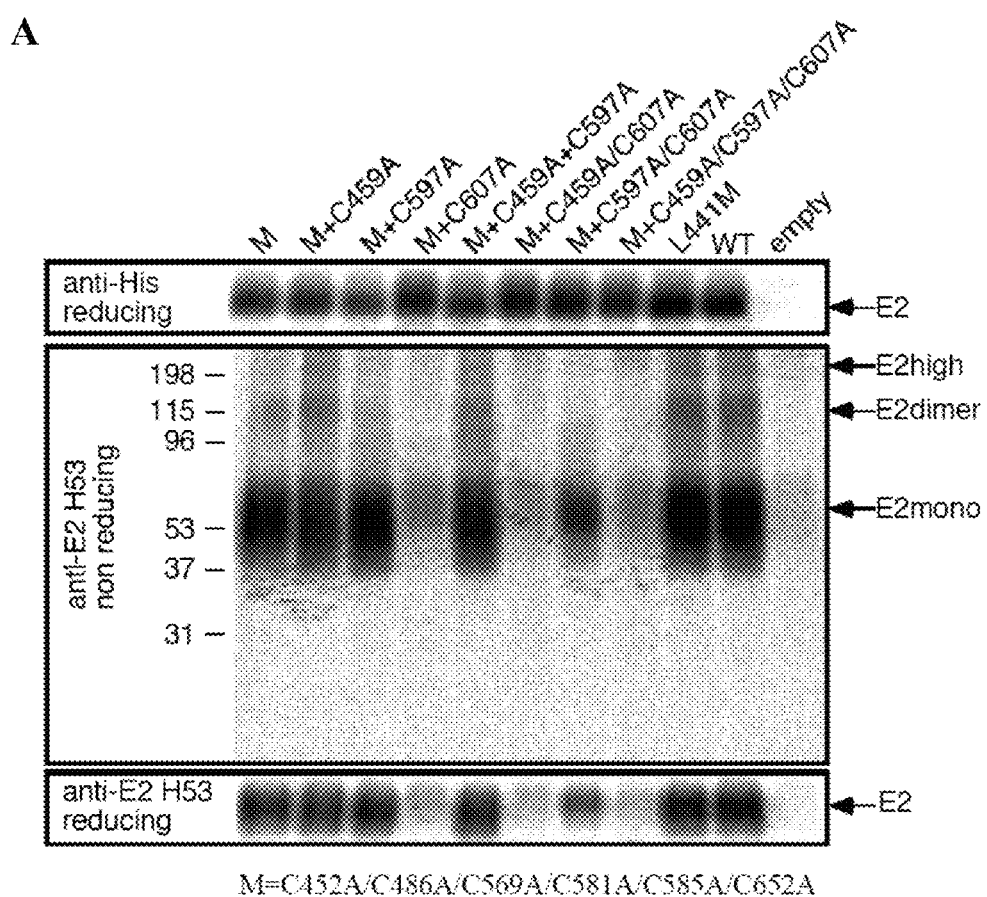
FIG. 6A through B illustrates the role of conserved cysteine residues in the formation of disulfide-linked oligomers or aggregates of truncated E2 ($E2_{661}$-his). A. Secretion and folding of $E2_{661}$-his containing multiple cysteine to alanine substitution mutations. SDS-PAGE analysis of radiolabelled, secreted $E2_{661}$-his containing multiple cysteine to alanine mutations immunoprecipitated with anti-HIS (top panel) or anti-E2 conformation-dependent MAb H53 under non-reducing (middle) and reducing (bottom) conditions. The migration of monomeric (E2mono), dimeric (E2dimer) and higher molecular mass forms (E2high) of $E2_{661}$-his under non-reducing conditions is indicated. The 'M' construct represents simultaneous mutations at positions C452, C486, C569, C581, C585 and C652. B. Binding to CD81-LEL by $E2_{661}$-his proteins containing multiple cysteine to alanine substitution mutations. Binding of secreted $E2_{661}$-his containing multiple Cys-to-Ala mutations to MBP-LEL$^{113-201}$ as detected by rabbit anti-His antibody. The L441M mutation within the E2 CD81-binding site represents a control for non-specific interactions. Loading controls for the same $E2_{661}$-his proteins are also shown (right panel) as captured by lectin and detected by anti-HIS.
Figure 6B:
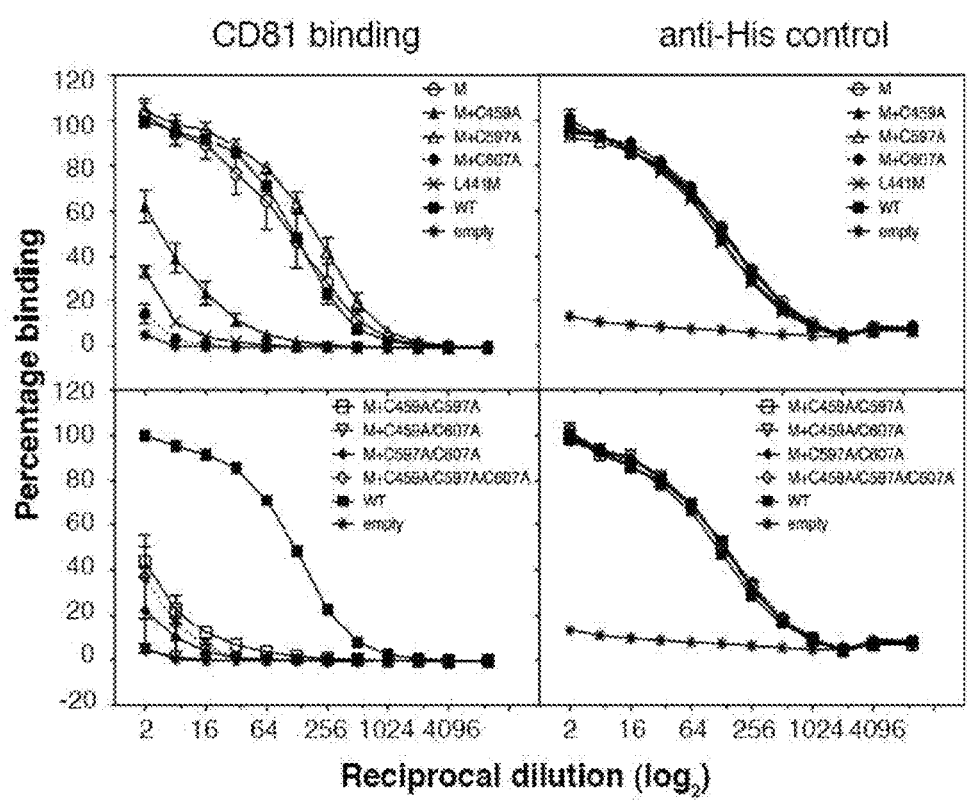

The pairwise analysis of individual cysteines involved in forming a disulfide by Ala replacement revealed that the absence of a Cys residue at 452, 459, 486, 569, 581, 585 or 652 is not necessarily unfavourable for E2 folding. In order to examine how the E2 fold tolerates the presence of unpaired Cys residues, E2$_{661}$-His mutants containing multiple Cys-Ala replacements were subjected to phenotypic analysis. Initially, Cys-Ala mutations exhibiting a WT phenotype (C452A, C486A, C569A, C581A, C585A and C652A) were combined in E2$_{661}$-his (designated 'M'). The M mutant exhibited wild type levels of H53 and LEL reactivity (FIGS. 6A and B), indicating that free cysteines at multiple positions are tolerated by the E2 fold. Further mutations, C459A, C597A and C607A, which affect CD81-binding function to varying degrees (see FIG. 4), were added individually to the M construct. The H53 and LEL binding characteristics of the M+C597A and M+C607A mutants were largely consistent with those of the individual C597A and C607A mutants (wild-type versus diminished H53 and LEL reactivity, respectively). By contrast, M+C459A exhibited an ~16-fold reduction in LEL binding, which does not correspond to the wild-type LEL binding activity of C459A. The simultaneous introduction of C459A, C597A and C607A in various combinations to M adversely affected H53 recognition and/or LEL binding function (FIG. 6). These data indicate that the LEL-binding competent fold of $E2_{661}$ possesses a strikingly high level of tolerance to the presence of unpaired Cys residues.

EXAMPLE 6

Conformational Plasticity Within the E2 Receptor Binding Domain

To further investigate the tolerance of $E2_{661}$-his to disulfide mutation, pair-wise mutations of C452A (Domain II), C486A (Domain II), C569A (Domain I) and C597A (Domain III) were introduced in different combinations; the individual mutants retain H53 reactivity and CD81 binding (FIGS. 4A and B). All double mutants were efficiently expressed and secreted as detected by anti-HIS, MAb H53 and retained WT or near-WT levels of CD81 binding (FIG. 7). The antigenic profiles of C452A-C486A and C452-C459A and C459A-C494A were also investigated using domain II reactive conformation sensitive MAbs. The C452A-C486A mutant exhibited wild-type levels of CBH-4B and CBH-4D reactivity while reactivity with CBH-4G was diminished In contrast, C459A-C494A failed to be recognized by any of the domain II specific MAbs. This is in contrast to the results obtained following mutation of the predicted disulfide pairs involving C569A and C486A where H53 reactivity and CD81 binding was abrogated (FIGS. 5A and B). Together the results suggest that (i) C452 is not required for acquisition of the native fold of the E2 receptor binding domain thus C459 does not require participation in a disulfide bond (ii) C597 and a disulfide pair involving this residue is not required for acquisition of the H53 epitope and CD81 binding (iii) simultaneous mutation of C486 and C494 was detrimental to H53 reactivity and CD81 binding, however, mutation of C452 and C486, C486 and C569 or C486 and C597 is tolerated for these functions suggesting that C494 does not require participation in a disulfide bond.

EXAMPLE 7

Intermolecular Disulfide-formation Between $E2_{661}$-his Molecules

Whidby et al., 2009 (supra) reported an increase in the monomer:dimer ratio of $E2_{661}$-His (genotype 2a) following replacement of the free Cys at position 652 with Ser. In contrast to these observations, a significant decrease in $E2_{661}$-His dimer or higher-order oligomers for C652A following H53 immunoprecipitation and non-reducing SDS-PAGE was not observed (FIG. 4A). To rule out possible thiol-disulfide rearrangement due to sample boiling, or selective immunoprecipitation by the conformation-dependent MAb (H53), radiolabelled $E2_{661}$-His proteins were purified using GNA lectin affinity chromatography for blue-native PAGE analysis. As shown in FIG. 8A, wild type and C652A $E2_{661}$-His proteins presented as monomeric, dimeric, trimeric and higher-order species with almost identical electrophoretic profiles. The quantitation of E2 species indicated an ~10%-increase in monomer for C652A relative to WT. This increase was not due to a reduction in the dimeric or trimeric forms, but rather conversion of higher molecular mass species to monomer. The electrophoretic profile of other individual Cys-to-Ala mutants were similar to that of wild type (data not shown). The 'M+597A' mutant, which retains H53 and LEL binding activities, exhibited a monomer yield-increase to approximately 60% of total protein, more than double that observed for WT and C652A with a marked reduction in all higher molecular mass species (FIG. 8B). These data obtained under native conditions are consistent with the reduction in higher molecular mass species detected by immunoprecipitation with MAb H53 and SDS-PAGE analysis (FIG. 6A). These data indicate that aberrant disulfides formed in the presence of C452, C486, C569, C581, C585, C597 (i.e. absent from M+C597A) contribute to the formation of high-order $E2_{661}$-His species.

EXAMPLE 8

Discussion

Hepatitis C Virus glycoprotein E2 performs the critical functions of mediating attachment of virions to cellular receptors that include CD81 and is a target of the humoral immune response. Following attachment of HCV to cell surface receptors, viral fusion proceeds and is believed to be dependent on the association of E2 with glycoprotein E1. Previous studies have shown that heterodimerization is mediated via the transmembrane domains of E1 and E2 and the membrane proximal region of E2 (residues 675-599) (Ciczora et al., *J Gen Virol* 86: 2793-8, 2005; Ciczora et al., *J Virol* 81: 2372-81, 2007; Drummer and Poumbourios, *J Biol Chem* 279: 30066-72, 2004). The biosynthetic folding pathway of E1 and E2 has not been fully elucidated. Critical to folding of a functional form of the E1E2 heterodimer are the 8 and 18 conserved Cysteine residues present in E1 and E2, respectively. Glycoprotein E2 is believed to have three immunogenic domains based on the results of monoclonal antibody mapping studies and the disulfide arrangement which allowed E2 to be modeled on a class II fusion protein (Keck et al., 2004 (supra); Krey et al., 2010 (supra)). As described herein, the invention is based upon a comprehensive mutagenesis analysis of individual cysteine residues in E2 and their proposed disulfide pairs according to that recently described by Krey et al., 2010 (supra) in the context of E1E2 and the isolated receptor binding domain ($E2_{661}$). The minimum number of disulfide bonds required for $E2_{661}$ to maintain biosynthesis, reactivity with a conformation dependent monoclonal antibody and CD8 1 binding has been delineated, revealing that $E2_{661}$ can tolerate a remarkable number of unpaired cysteines as well as loss of disulfide 6 and/or 9.

Domain I is believed to be comprised of 8 antiparallel β strands stabilized through two disulfides (1 and 5). The majority of the CD81 interaction surface is located in domain I but is believed to partially overlap with Domain III. Mutagenesis of either disulfide 1 or 5, revealed that both are essential for E2 to be virion incorporated, and for $E2_{661}$ to fold into a structure that binds conformation dependent antibody H53 and CD81. Thus disulfide 1 and 5 are essential for domain I structural integrity (C429/555 and C564/569 in FIG. 9). However, domain I tolerates the presence of free thiol groups in other domains as simultaneous mutation of C452, C486, C569, C581, C585, C597 and C652 maintained H53 and CD81 reactivity at wild-type levels. Furthermore, the propensity of $E2_{661}$ to fold into higher molecular weight species (dimer, trimer and higher order oligomers) was reduced in the multiple mutant C452A, C486A, C569A, C581A, C585A, C597A and C652A, resulting in a significant increase in the amount of monomeric $E2_{661}$ secreted from transfected cells. These data suggest that free thiols at residues C459, C494, C564 and C620 are tolerated within $E2_{661}$ and are beneficial to minimize aberrant disulfide formation.

Domain II extends from B sheet D0 and E0 and is characterized by the presence of three disulfides formed through pairings of adjacent Cys residues. The absence of long range disulfides led to the suggestion that this domain may be flexible (Krey et al., 2010 (supra)). The use of monoclonal antibodies that describes three immunogenic domains suggested that domain A may be flexible and capable of movement in response to low pH (Keck et al., *J Virol* 79: 13199-208, 2005). Mutagenesis of the disulfide pairs within domain II reveals that C486/C494 (disulfide 3) and C503/C508 (disulfide 4) are essential for virion-incorporation of E2, and formation of the H53 epitope, reactivity of domain A antibodies and CD81 binding sites. It is inferred that domain II corresponds to domain A. Although distal to the CD81 binding sites, disulfides 3 and 4 are directly adjacent to hypervariable region 2 and a predicted fusion loop within Domain II, respectively. This suggests that the formation of this structure is essential for formation of the adjacent Domain I/III substructure and their associated functions. By contrast, mutagenesis of C452/C459 (disulfide 2) maintained partial reactivity to H53, domain A antibodies and CD81 binding, suggesting it is less important to the structural integrity of E2. Indeed, single mutation of either C452 or C459 creating a free thiol at this site was tolerated for H53 reactivity and CD81 binding in both virion incorporated E2 and $E2_{661}$.

Figure 7A:
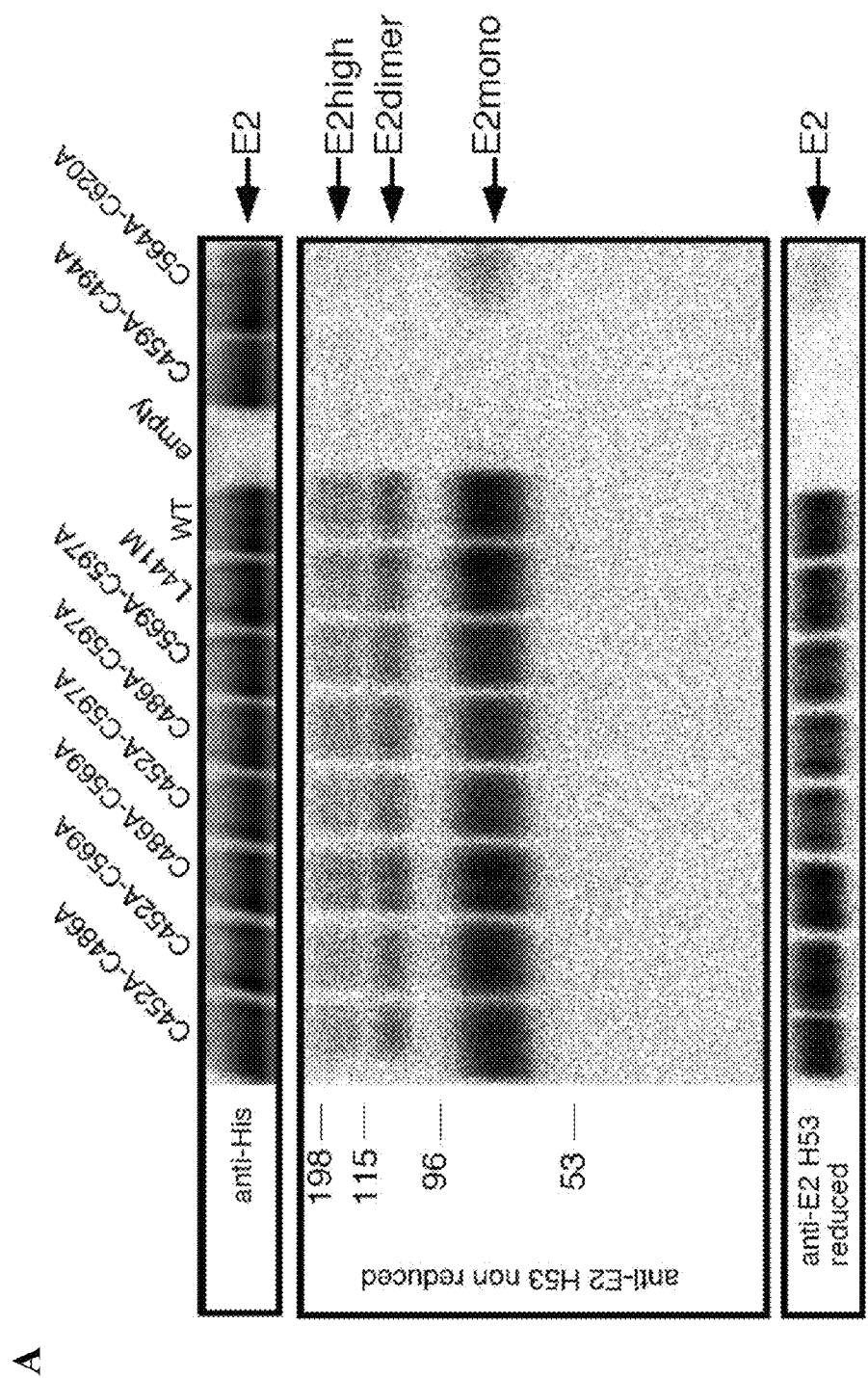
FIG. 7A through C illustrates mutagenesis of alternative disulfide pairs in truncated E2 ($E2_{661}$-his). A. Expression, secretion and folding of $E2_{661}$-his proteins containing alternative pair-wise cysteine to alanine substitution mutations. Pairwise cysteine to alanine mutation was performed of non-essential cysteines in $E2_{661}$-his. SDS-PAGE analysis of radiolabelled, secreted $E2_{661}$-his immunoprecipitated with anti-HIS (top panel) or anti-E2 conformation-dependent MAb H53 under non-reducing (middle) and reducing (bottom) conditions. The expected migration of monomeric (E2mono), dimeric (E2dimer) and higher molecular mass (E2high) forms of $E2_{661}$-his under non-reducing conditions is indicated. B. Binding to CD81-LEL by $E2_{661}$-his proteins containing pair-wise cysteine to alanine substitution mutations. Binding of secreted $E2_{661}$-his containing alternative pair wise Cys-to-Ala mutations to MBP-LEL$^{113-201}$ as detected by rabbit anti-His antibody. The L441M mutation within the E2 CD81-binding site represents a control for non-specific interactions. Loading controls for the same $E2_{661}$-his proteins are also shown (right panel) as captured by lectin and detected by anti-HIS. C. Conformational changes within domain A. Selected mutants were assessed for their ability to be detected by conformation sensitive antibodies specific to immunogenic domain A (Keck et al., 2004 (supra)). Radiolabelled $E2_{661}$-his proteins were immunoprecipitated with the indicated MAbs and examined under non-reducing conditions.
Figure 7B:
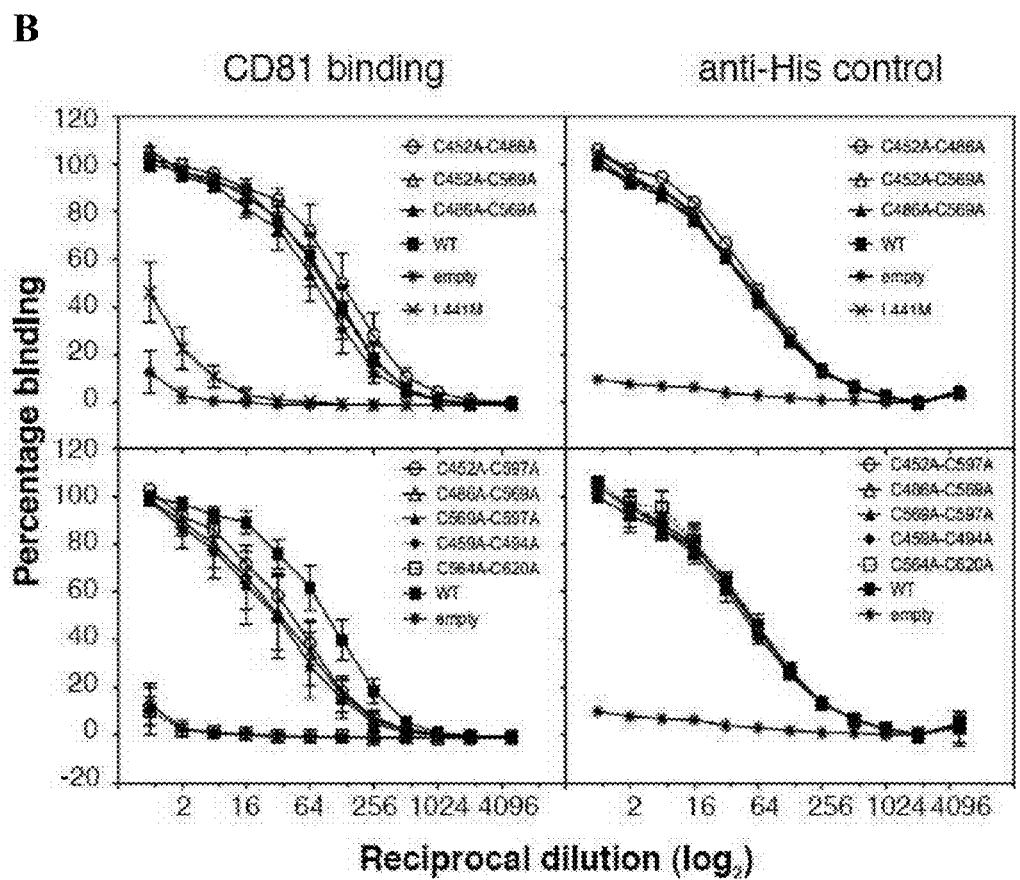
Figure 7C:
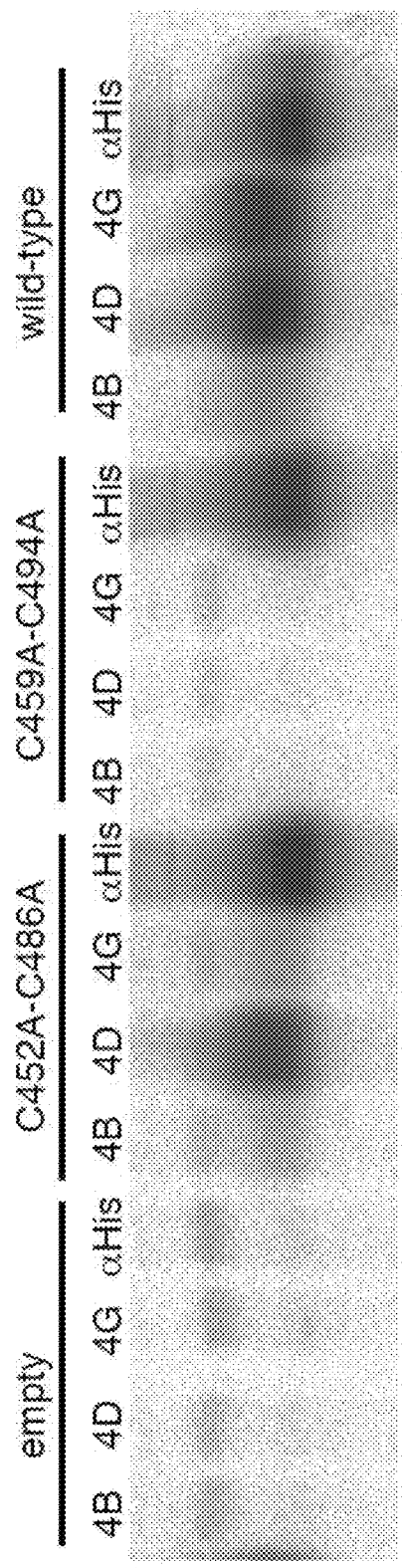

The degree of tolerance of $E2_{661}$ to the presence of unpaired cysteines was explored by mutagenesis of one residue from each of two pairs. The residues analysed were chosen on the basis that single mutations did not alter CD81 binding or H53 reactivity. Mutation of C452 (within disulfide 2) and C486 (within disulfide 3) or C564 and C569 (within disulfide 5) resulted in the expression of H53 reactive $E2_{661}$ that retained wild-type levels of CD81 binding. This result is in contrast to the complete removal of disulfide 2 (452/459) that resulted in a 60% decrease in CD81 binding activity. These results suggest that a free thiol at C459 or C494 within domain II is more favorable than complete removal of either of disulfides 2 or 3 to formation of the CD81 binding site located within domain I and III. This may suggest that C452, C486 and C569 are responsible for aberrant disulfide formation during the biosynthesis of E2 that decreases the yield of properly folded $E2_{661}$. It is predicted that there is less oligomeric forms of $E2_{661}$ with these mutants either individually and/or in combination. Alternatively, these amino acids may be in disulfide exchange forming labile disulfides, with C452/C459 an end product of this exchange mechanism and alternative pairings of C452 with C486 and C569 intermediate pairings. It is unlikely that C452 is involved in a stable disulfide with C486 in domain II as removal of this Cys pair reduced reactivity of domain A antibodies despite retaining wild-type CD81 binding. Furthermore, mutagenesis of C459/C494 (the alternative pair likely if C452 and C486 were disulfide paired) abolished H53 and CD81 binding (FIG. 7).

The pattern of effects observed for virion-incorporated E2 and $E2_{661}$ was similar for both the single cysteine mutations and the double substitutions of proposed disulfides (FIG. 9). This confirms that the disulfide arrangement of full length E2 expressed in association with E1 and the isolated receptor-binding domain is similar and largely validates the arrangement proposed by Krey et al., 2010 (supra). The exceptions to this are disulfides 7 and 8 within domain III. Mutagenesis of either disulfide resulted in a loss of H53 reactivity and CD81 binding in E1E2 but these functions were maintained in $E2_{661}$. The data suggest that expression of E2 containing the stem region and TMD with glycoprotein E1, increases the susceptibility of domain III to structural changes as a result of disulfide 7 and 8 mutagenesis.

As described herein, the formation of a CD81 binding competent structure for $E2_{661}$ requires the presence of only three disulfides; C429/552 (Domain I), C503/508 (Domain II) and C607/677 (Domain III). For the remaining cysteines the disulfide can either be removed (C581/585, C652/677) or unpaired C494, C459, C569 and C620 without affecting this conformational capability. In addition, the presence of free thiols at C494, C459, C569 and C620 is unexpectedly favourable to formation of larger amounts of monomeric $E2_{661}$.

In a Cys-to-Ala mutagenesis study of HIV-1 gp120/gp41, hierarchical effects of mutagenesis were observed for the ten disulfides with the majority of mutations adversely effecting folding of the envelope complex (van Anken et al., 2008 (supra)). The effect of single Cys-to-Ala mutations was recapitulated in the double mutation within a pair with respect to folding and association of gp120/gp41. In one case, the single cys-to-ala mutation was detrimental to viral replication while removal of the pair restored replication. In contrast, in HCV E2, individual mutation of cysteines within three disulfides resulted in discordant effects. Mutation of C564, C494 and C508 abolished H53 reactivity and CD81 binding while the cysteines within their disulfide pairs, C569, C486 and C503, maintained one or both of these functions. This suggests that the location or orientation of the cysteines is such that single mutagenesis results in the remaining cysteine of the pair forming aberrant disulfides ablating H53 and CD81 binding. Conversely, the steric environment of its partner Cys when present as a free thiol prevents its particpation in forming aberrant disulfides and E2 folding proceeds into a quasi-native structure. Alternatively, the removal of the hydrophilic side chain by mutation to alanine is detrimental to the local conformation and the H53 and CD81 reactivity is lost. Mutagenesis of C564, C508 and C494 to Ser will resolve this possibility.

Each of the 9 disulfides of HCV E2 is strictly required for the formation of an entry competent structure. This is in contrast to what has been observed for HIV-1 gp120/gp41 were two disulfides are not essential for virus replication (van Anken et al., 2008 (supra)). In E2, HCVpp incorporating the disulfide 6 mutant maintained H53 reactivity, heterodimerization with E1 and CD81 binding but failed to enter cells. It is likely that its defect occurs post-CD81 binding and may be related to conformational changes either induced by interactions with other cellular receptors such as SR-B1, claudin-1 and occludin, or low pH dependent conformational changes associated with viral fusion. Disulfide 6 is located adjacent to the igVR that has been proposed to act as hinge between domains I and III (Krey et al., 2010 (supra)). In the flavivirus glycoprotein E, exposure to low pH changes the centre of mass of domain III displacing it 33 Å such that the virion-membrane anchored stem and adjoining TMD now apposes the target membrane anchored fusion loop, driving membrane merger (Bressanelli et al., *Embo J* 23: 728-38, 2004). Our data suggests that disulfide 6 may be essential for the igVR of E2 to perform a similar function.

The results of this study provide new insights on E1E2 structure and function and reveal new methods for synthesising larger amounts of monomeric E2 that retains CD81 binding function. In addition, this study validates the proposed disulfide arrangement of E2 and confirms that the isolated E2 receptor binding domain and virion incorporated E2 are likely to have the same disulfide arrangement. The modified HCV E2 RBD provides therefore a lead candidate for the production of a prophylactic vaccine and crystallization studies to resolve the three dimensional structure.

EXAMPLE 9

Simultaneous Mutation of C452A, C486A, C569A, C581A, C585A, C597A and C652A (M+C597A) in Both Wild-Type $E2_{661}$ and $\Delta 123$ $E2_{661}$ Result in the Expression of a Secreted Form of E2 that is Recognized by Conformation Dependent Monoclonal Antibody H53

To examine whether simultaneous mutation of C452A, C486A, C569A, C581A, C585A, C597A and C652A could also prevent the formation of intermolecular disulphide bonding in a second modified form of E2661 in which the three variable regions, hypervariable region 1 (HVR1), hypervariable region 2 (HVR2) and the intergenotypic variable region (igVR) are removed (HVR1) or replaced (HVR2 and igVR) with flexible Gly-Ser-Ser-Gly linkers. The example shows that mutation of C452A, C486A, C569A, C581A, C585A, C597A and C652A in both WT $E2_{661}$ and $\Delta 123$ $E2_{661}$ results in the expression of similar amounts of protein from transfected 293T cells which is immunoprecipitated by conformation dependent monoclonal antibody H53. This demonstrates that simultaneous mutation of C452A, C486A, C569A, C581A, C585A, C597A and C652A does not affect the level of protein expression or the conformation of WT $E2_{661}$ and $\Delta 123$ $E2_{661}$ as detected by MAb H53. (See for example, FIG. 10).

EXAMPLE 10

WT $E2_{661}$ (M+C597A) and $\Delta 123$ $E2_{661}$ (M+C597A) Proteins are Recognized by Neutralizing Monoclonal Antibodies and Conformation Dependent Antibody H53

Next, it was determined whether WT $E2_{661}$ and $\Delta 123$ $E2_{661}$ with simultaneous mutations of C452A, C486A, C569A, C581A, C585A, C597A and C652A could be recognized by monoclonal antibodies capable of preventing the infection of liver cells with HCV in vitro. Monoclonal antibodies were serially diluted in enzyme immunoassay plates coated with similar amounts of $E2_{661}$ M+C597A, $\Delta 123$ $E2_{661}$M+C597A and the non-mutated forms of $E2_{661}$ and $\Delta 123$ $E2_{661}$. The results show that both MAb 24 (411-428) and MAb 44 (512-529) recognized the wild-type and M+C597A proteins at similar levels relative to the loading control (anti-His directed to C-terminal epitope tag) and were similar to the binding observed with conformation dependent non neutralizing antibody H53. These results indicate that mutation of C452A, C486A, C569A, C581A, C585A, C597A and C652A did not alter the antigenicity of $E2_{661}$ or $\Delta 123$ $E2_{661}$ as recognized by H53, MAb 24 and MAb 44. (See for example, FIG. 11)

EXAMPLE 11

WT $E2_{661}$ (M+C597A) and $\Delta 123$ $E2_{661}$ (M+C597A) Proteins are Recognized by Immune Serum Raised to WT $E2_{661}$ and $\Delta 123$ $E2_{661}$ It was confirmed that $E2_{661}$ (M+C597A) and $\Delta 123$ $E2_{661}$ (M+C597A) proteins were recognized by immune serum generated to the non-mutated parental forms of $E2_{661}$ and $\Delta 123$ $E2_{661}$. Immune serum was generated to $E2_{661}$ and $\Delta 123$ $E2_{661}$ by vaccinating guinea pigs with 100 µg of protein three times at three weekly intervals. The final bleed was serially diluted ½ log onto enzyme immune assay plates coated with similar amounts of the parental non mutated $E2_{661}$, the parental non mutated $\Delta 123$ $E2_{661}$, $E2_{661}$ (M+C597A) or $\Delta 123$ $E2_{661}$ (M+C597A). Immune serum recognized each of the proteins similarly further confirming that $E2_{661}$ (M+C597A) and $\Delta 123$ $E2_{661}$ (M+C597A) retain the conformation of their parental counterparts. (See for example, FIG. 12)

EXAMPLE 12

WT $E2_{661}$ (M+C597A) and $\Delta 123$ $E2_{661}$ (M+C597A) Proteins Bind CD81

It was next verified that both the $E2_{661}$ (M+C597A) and $\Delta 123$ $E2_{661}$ (M+C597A) proteins retained the ability to bind a recombinant form of the cellular receptor CD81. Serial dilutions of $E2_{661}$ (M+C597A) and $\Delta 123$ $E2_{661}$ (M+C597A) were added to enzyme immune assay plates coated with 5 µg/ml CD81. Bound $E2_{661}$ was detected with anti-His immunoglobulins and goat anti-rabbit horse-radish peroxidase conjugated antibodies. The MBP-LEL[113-201] E2 binding mutant F186S was included to reveal the background level of binding obtained with each of the proteins (WT $E2_{661}$ shown). The results demonstrate that the parental non-mutated forms of $E2_{661}$ and $\Delta 123$ proteins displayed similar levels of binding to CD81 as their $E2_{661}$ (M+C597A) and $\Delta 123$ $E2_{661}$ (M+C597A) counterparts. These results provide evidence that the CD81 interaction surface formed in $E2_{661}$ (M+C597A) and $\Delta 123$ $E2_{661}$ (M+C597A) is retained by simultaneous mutations C452A, C486A, C569A, C581A, C585A, C597A and C652A. (See for example, FIG. 13)

EXAMPLE 13

Figure 8A:
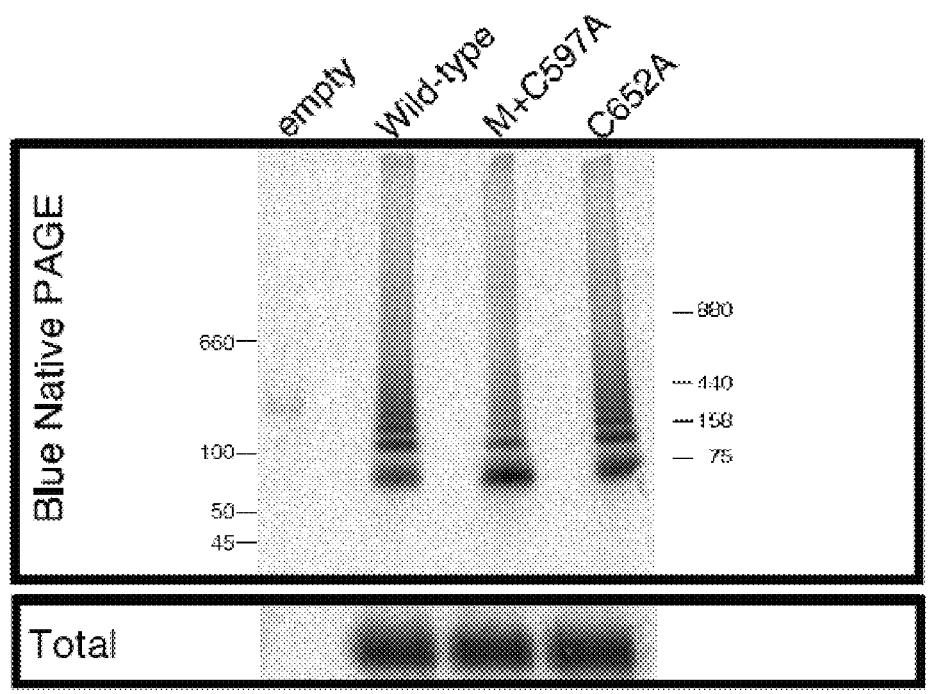
FIG. 8A through B illustrates the propensity of $E2_{661}$-his containing the minimum number of cysteine residues to form monomeric, dimeric and higher molecular mass forms of E2. A. Comparison of disulfide-linked multimers formed by $E2_{661}$-his containing C652A or 'M+C597A' mutations. Blue-native PAGE analysis of lectin-affinity purified radiolabelled $E2_{661}$-his representing either C652A, 'M+C597A' or WT proteins as detected by radioisotope imaging (top panel).
Figure 8B:
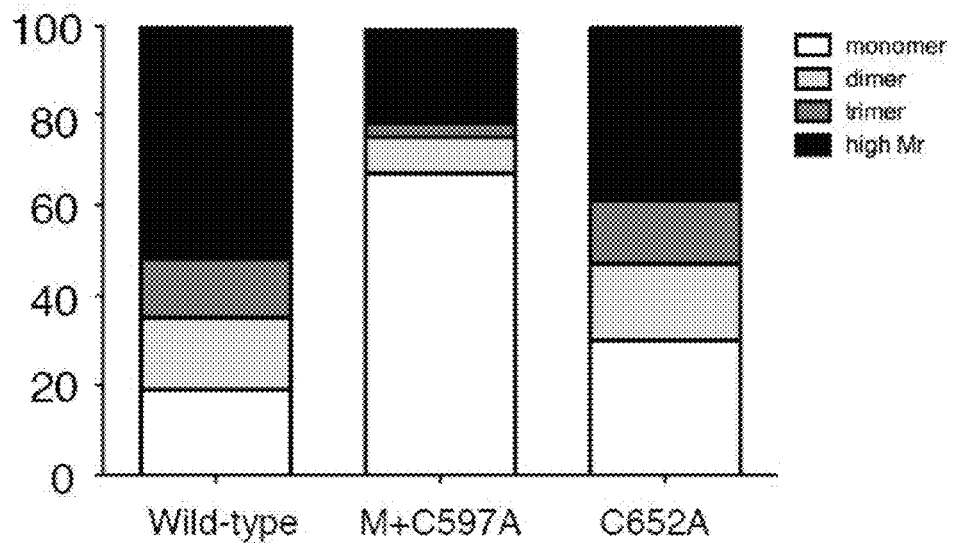

Gel Filtration Chromatography of (A) WT $E2_{661}$ (M+C597A) and (B) $\Delta 123$ $E2_{661}$ (M+C597A) Proteins Blue native PAGE data (FIG. 8) showed that the amount of monomeric $E2_{661}$ was increased from approximately 20% in the parental form of $E2_{661}$ to approximately 70% of $E2_{661}$ M+C597A. The oligomerization of $E2_{661}$ was examined using gel filtration chromatography using a Superdex 200 size exclusion column. In this system, nickel affinity purified proteins are loaded directly onto equilibrated columns and the proteins separated according to their size and shape. The data show that the parental non-mutated forms of $E2_{661}$ and $\Delta 123$ $E2_{661}$ are comprised of a heterogeneous mixture of $E2_{661}$ consistent with the molecular mass of monomer and dimer, trimer and higher molecular weight species. By contrast, the simultaneous mutation of C452A, C486A, C569A, C581A, C585A, C597A and C652A results in the production of a single species of $E2_{661}$ consistent with the expected molecular mass of monomeric glycosylated $E2_{661}$(A) and $\Delta 123$ $E2_{661}$ (B). These results suggest that formation of intermolecular disulfides in E2661 is likely mediated by one or more of C452, C486, C569, C581, C585, C597 and C652 and that simultaneous mutation of C452A, C486A, C569A, C581A, C585A, C597A and C652A abolishes the formation of intermolecular disulfides in $E2_{661}$ whilst retaining the ability of E2661 to bind CD81 and its recognition by neutralizing (MAb 24, MAb 44) and conformation dependent antibodies (H53). (See for example, FIG. 14)

EXAMPLE 14

Immune Serum Inhibition of the Binding of E2 to the Cell Surface Receptor CD81

The ability of the immune sera to inhibit the binding of HCV glycoprotein E2 to CD81 is an indicator of the ability of immune serum to inhibit the ability of HCV to enter target cells. The ability of immune sera generated to WT $E2_{661}$ (M+C597A) and $\Delta123$ $E2_{661}$his (M+C597A) to block the interaction between $E2_{661}$his protein and the recombinant form of the large extracellular loop of CD81 (MBP-LEL$^{113-201}$) is examined in a solid phase enzyme immunoassay.

In an illustrative example, serial dilutions of immune sera are mixed with 100 ng of either H77c or JFH1 WT $E2_{661}$his proteins before addition to MBP-LEL$^{113-201}$ coated immunoassay plates. Bound $E2_{661}$his will be detected using anti-His antibody. The 80% inhibition titre is calculated for each serum sample and plotted as a dot-plot. The data will show whether animals vaccinated with WT $E2_{661}$ (M+C597A) and $\Delta123$ $E2_{661}$his (M+C597A) elicit high titres of antibody capable of inhibiting the E2-CD81 interaction using both homologous H77c and heterologous JFH1 $E2_{661}$. This will also demonstrate that the M+C597A form of both the WT and $\Delta123$ $E2_{661}$his protein is immunogenic and elicits antibody capable of inhibiting E2-CD81 binding.

EXAMPLE 15

Homologous Neutralization of H77c HCVpp

The ability of immune sera to mediate homologous neutralization will be determined using retroviral pseudotyped particles containing the H77c E1E2 glycoproteins. Serial dilutions of heat inactivated immune sera are admixed with HCVpp and added to Huh7.5 cells for 4 h. After washing, cells are incubated for a further 3 days and luciferase activity quantitated in the cell lysate. The titre of antibody required to mediate 50% and 80% neutralization will be determined.

EXAMPLE 16

Immune Sera to Mediate Cross Neutralization of Cell Culture Derived J6-JFH1

The ability of immune sera to mediate heterologous neutralization will be determined using J6-JFH1 cell culture derived HCV. Serial dilutions of immune sera will be mixed with J6-JFH1 cell culture derived HCV and added to Huh7.5 cells. The luciferase activity in supernatant fluid will be quantitated 44 h after infection. The titre of antibody required to mediate 50% and 80% neutralization will be determined.

EXAMPLE 17

Further Discussion

In the context of HCVpp, each of the nine disulfides of HCV E2, and their corresponding cysteine residues, were shown to be absolutely required for the formation of an entry competent structure. Characterisation of the effect of these mutations on E2 folding and CD81 binding activity using the conformation-dependent monoclonal antibody H53, polyclonal anti-E2 antibody and recombinant CD81 generated similar phenotypic profiles for both virion-incorporated E2 and $E2_{661}$. This confirms that the disulfide arrangement of full-length E2 expressed in association with E1 and the isolated receptor-binding domain is largely similar. The notable exceptions to this were mutation of disulfides 7 or 8 within domain III that resulted in a loss of H53 reactivity and/or CD81 binding in the context of E1E2, but were partially tolerated within $E2_{661}$. These 1 data suggest that the expression of E2 containing the stem regions and TMD with glycoprotein E1 increases the susceptibility of domain III to structural changes as a result of these mutants.

The pattern of effects on H53 reactivity and CD81 LEL binding observed for the disulfide mutants also largely validated the model of E2 proposed by Krey et al. For example, domain I (DI) is predicted to comprise of 8 antiparallel β-strands stabilized through two disulfides (1 and 5). The majority of the CD81 interaction surface is located in domain I but is also proposed to partially overlap with Domain III. Mutagenesis revealed disulfide 1 to be required for virion-incorporation of E2 and for $E2_{661}$ to fold into a structure that binds conformation dependent antibody H53 and CD81, consistent with an essential role for this relatively long-range disulfide in maintaining the structural integrity of E2. Conversely, disulfide 9 was not essential for the formation of either the H53 epitope or LEL binding consistent with its location distal to the CD81-binding site and overlapping the proposed 'stem' region (Drummer et al., 2004 (surpa)). Mutation of disulfide 9 also corresponded to a loss of E1 contacts in agreement with previous reports of heterodimerisation determinants within this region (Drummer et al., 2004 (surpa)).

In the context of HCVpp, the disulfide 6 mutant maintained H53 reactivity, heterodimerisation with E1 (albeit at reduced levels) and CD81 binding, but was not entry competent. It is likely that its defect occurs post-CD81-binding and may be related to conformational changes either induced by interactions with other cellular receptors such as SR-B1, Claudin-1 and/or Occludin, or low-pH induced conformational changes associated with viral fusion. Disulfide 6 is located adjacent to the igVR that has been proposed to act as a hinge between domains I and III. In flavivirus glycoprotein E, exposure to low pH changes the centre of mass of domain III, displacing it 33 Å, such that the viral membrane anchored stem and adjoining TMD now appose the target 1 membrane anchored fusion loop, driving membrane merger. As taught herein, disulfide 6 may be essential for the igVR of E2 to perform a similar function.

Domain II extends from β-sheets D0 and E0 of domain I and is characterized by the presence of three disulfides formed through pairings of neighbouring cysteine residues. The absence of long-range disulfides led to the suggestion that this domain may be a relatively flexible region within E2. Mutagenesis of disulfide pairs within domain II reveals that formation of disulfide 4 was essential for virion incorporation of E2, H53 epitope assembly and CD81-binding function. Although distal to the CD81-binding sites, disulfide 4 overlaps the predicted fusion loop. This suggests that the formation of this structure is essential for formation of the adjacent domain I/III substructure and their associated functions. By contrast, mutagenesis of disulfide 2 (C452-C452) in $E2_{661}$ maintained partial reactivity to H53 and CD81-LEL suggesting that it is less important to the structural integrity of E2. Interestingly, individual mutation of either C452 or C459 to create a free thiol at either site resulted in wild type levels of H53 reactivity and CD81-LEL binding and was therefore more favorable than complete removal of disulfide 2. It is possible that within the prefusion virion incorporated form of E1E2, C452 and C459 exist in a reduced state or form a labile disulfide in the domain II substructure, where formation of disulfide 2 represents an end product of thiol disulfide exchange.

Also taught is a high degree of tolerance for the loss of predicted disulfide bonds within $E2_{661}$ folding and/or function as disruption of disulfides 3, 4 and 5 via mutations at residues C486, C503 and C569 maintained WT H53 reactivity and/or CD81-LEL binding However, discordant effects were observed upon mutation of their disulfide-bonding partners—C494, C508 or C564, respectively—that saw the loss of these functions. Pair-wise mutation of 1 these residues corresponding to their predicted disulfides did not alleviate this loss of function phenotype indicating that the presence of a free thiol was unlikely to be responsible for misfolding via the formation of aberrant disulfides as previously described in a similar cysteine mutagenesis study of the HIV gp120/gp41 complex (26). This would indicate that the Cys-to-Ala mutation at these sites was detrimental to local conformation within E2 resulting in a loss of H53 and CD81 binding. Removal of the hydrophilic side-chain by mutation to an alanine may have contributed to this phenotype. Introduction of serine rather than alanine at these positions may reduce alanine induced conformational defects and clarify the role of these cysteines in E1E2 function.

The minimal number of cysteine residues required for $E2_{661}$ to maintain WT biosynthesis, H53 reactivity and CD81 binding was delineated using a phenotypic mutagenesis approach. Simultaneous introduction of C452A, C486A, C569A, C597A, C581A, C585A and C652A (M+C597A) resulted in the expression of wild-type levels of $E2_{661}$ that maintained H53 and CD81 binding activity. This suggested that C459, C494, C564 and C620 exist as free thiols as there was no evidence that these residues engaged in a specific, alternative pattern of disulfide bonding. Consistent with the presence of free thiols, the M+C597A mutant also displayed a reduced propensity to form higher molecular weight species resulting in a significant increase in the amount of monomeric $E2_{661}$ secreted from transfected cells that was not observed for any of the individual mutants. Together these data indicate that free thiols at positions 459, 494, 564 and 620 are tolerated in a CD81 binding-competent $E2_{661}$ structure and that their predicted disulfide-bonding partners (C452, C486, C569 and C597) are available to engage in a complex pattern of aberrant, intermolecular disulfide bonds during $E2_{661}$ biosynthesis. As the cysteine mutagenesis results obtained with $E2_{661}$ largely residues also include determinants for disulfide-mediated, intermolecular contacts between E2 molecules, as well as between E1 and E2, as has been recently described on the surface of the mature HCV virions (Vieyres et al., 2010 (supra)).

In summary, the results of this study provide new insights into E1E2 structure and suggest that virion-incorporated E2 and soluble $E2_{661}$ share a similar disulfide bonding arrangement. We have reported that the formation of a CD81-competent structure of $E2_{661}$ strictly requires the presence of three disulfides across each of the three predicted domains: C429-C552A (DI), C503-C508 (DII) and C607-C644 (DIII). For the remaining cysteines, the disulfide can either be removed (C581-C585 or C652-C677) or unpaired (C459, C494, C564 or C620) without affecting this basic conformational requirement. Our data also suggests that the presence of unpaired thiols within E2 may reflect a mechanism for intra- or intermolecular disulfide exchange. In addition, the removal of, C452, C486, C569, C581, C585, C597 and C652 is somewhat unexpectedly favorable to the formation of larger amounts of functional, monomeric $E2_{661}$ and may signal a new approach to synthesizing larger amounts of soluble E2 as a lead candidate for crystallization studies and the resolution of a three dimensional structure.

As described in Examples 9 to 13, the ability to simultaneously mutate the seven cysteines to alanine (M+C597A) whilst retaining CD81 binding, recognition by conformation dependent antibodies and substantially increasing the yield of monomer is not restricted to the parental form of recombinant $E2_{661}$. Mutation of C452A, C486A, C569A, C581A, C585A, C597A and C652A in a recombinant form of $E2_{661}$ where the three variable regions have been removed (Δ123) also resulted in its expression as a monomeric protein by gel filtration and the protein retained wild-type levels of CD81 binding and H53 reactivity. These data suggest that the formation of disulphide linked forms of Δ123 can also be prevented by mutations C452A, C486A, C569A, C581A, C585A, C597A and C652A.

Many modifications will be apparent to those skilled in the art without departing from the scope of the present invention.

TABLE 1

The location of conserved cysteines in HCV glycoprotein E2

| Mutation | Relative position | Domain assignment |
| --- | --- | --- |
| C429A | 1 | I |
| C452A | 2 | II |
| C459A | 3 | II |
| C486A | 4 | II |
| C494A | 5 | II |
| C503A | 6 | II |
| C508A | 7 | II |
| C552A | 8 | I |
| C564A | 9 | I |
| C569A | 10 | I |
| C581A | 11 | III |
| C585A | 12 | III |
| C597A | 13 | III |
| C607A | 14 | III |
| C620A | 15 | III |
| C644A | 16 | III |
| C652A | 17 | III |
| C677A | 18 | stem |

TABLE 2

Disulfide pairing of the 18 Cys residues of HCV glycoprotein E2

| Pair | Domain | Disulfide number |
| --- | --- | --- |
| C429-C552 | I | 1 |
| C564-C569 | I | 5 |
| C581-C585 | III | 6 |
| C452-C459 | II | 2 |
| C486-C494 | II | 3 |
| C503-C508 | II | 4 |
| C597-C620 | III | 7 |
| C607-C644 | III | 8 |
| C652-C677 | III | 9 |

TABLE 3

Suitable naturally occurring proteogenic amino acids

| Amino Acid | one letter code | three letter code |
| --- | --- | --- |
| L-alanine | A | Ala |
| L-arginine | R | Arg |
| L-asparagine | N | Asn |
| L-aspartic acid | D | Asp |
| L-cysteine | C | Cys |
| L-glutamine | Q | Gln |
| L-glutamic acid | E | Glu |
| glycine | G | Gly |
| L-histidine | H | His |
| L-isoleucine | I | Ile |
| L-leucine | L | Leu |
| L-lysine | K | Lys |
| L-methionine | M | Met |
| L-phenylalanine | F | Phe |
| L-proline | P | Pro |
| L-serine | S | Ser |
| L-threonine | T | Thr |

TABLE 3-continued

Suitable naturally occurring proteogenic amino acids

| Amino Acid | one letter code | three letter code |
|---|---|---|
| L-tryptophan | W | Trp |
| L-tyrosine | Y | Tyr |
| L-valine | V | Val |

TABLE 4

Amino acid sub-classification

| Sub-Classes | Amino Acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

TABLE 5

Exemplary and Preferred Amino Acid Substitutions

| Original Residue | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

BIBLIOGRAPHY

Atherton and Shephard, *Peptide Synthesis. In Nicholson ed, Synthetic Vaccines*, published by Blackwell Scientific Publications, Chapter 9

Ausubel et al., *Cell Immunol.*, 193(1): 99-107, 1999

Ausubel et al., *Current Protocols in Molecular Biology*, Green Pub. Associates and Wiley-Interscience, New York, 1988

Ausubel et al., *Current Protocols in Molecular Biology*, John Wiley & Sons Inc, Chapters 10 and 16, 1994

Bandyopadhyay and Temin, *Mol. Cell. Biol.* 4: 749-754, 1984

Berglund et al., *Biotechnology* 11: 916-920, 1993

Berkner et al., *BioTechniques* 6: 616-629, 1988

Berkner, *Curr. Top. Microbiol. Immunol.* 158: 39-66, 1992

Bird, *Science* 242: 423, 1988

Breakefield and Geller, *Mol. Neurobiol.* 1: 339-371, 1987

Bressanelli et al., *Embo J* 23: 728-38, 2004

Buchschacher and Panganiban, *J. Virol.* 66: 2731-2739, 1982

Carter et al., *Bio/Technology* 10: 163-167, 1992

Carter et al., *Proc. Nat. Acad. Sci.* 89: 4285 1992

Ciczora et al., *J Gen Virol* 86: 2793-8, 2005

Ciczora et al., *J Virol* 81: 2372-81, 2007

Clackson et al., *Nature* 352: 624-628, 1991

Coligan et al., *Current Protocols in Protein Science*, John Wiley & Sons, Inc. Chapters 1, 5 and 6, 1995-1997

Colowick and Kaplan, eds., *Methods In Enzymology*, Academic Press, Inc.

Dayhoff et al., *Atlas of Protein Sequence and Structure*, Natl. Biomed. Res. Found., Washington, D.C., 1978

Dayhoff, (ed.), *Atlas of protein sequence and structure*, National Biomedical Research Foundation, Washington D.C., Vol. 5, pp. 345-358

Drummer and Poumbourios, *J Biol Chem* 279: 30066-72, 2004

Drummer et al. *FEBS Lett* 546: 385-90, 2003

Drummer et al., *Biochem Biophys Res Commun* 328: 251-257, 2005

Drummer et al., *J Virol* 76: 11143-7, 2002

Drummer et al., *J Virol* 80: 7844-53, 2006

Fields and Knipe, eds, *Fundamental Virology*, 2nd Edition, 1991

Fields et al., eds, *Virology*, 3rd Edition, Lippincott-Raven, Philadelphia, Pa., 1996

Fink et al., *Ann. Rev. Neurosci.* 19: 265-287, 1996

Fink et al., *Hum. Gene Ther.* 3: 11-19, 1992

Fraser et al., *J Biol Chem* 2011, In print

Freese et al., *Biochem. Pharmacol.* 40: 2189-2199, 1990

Gonnet et al., *Science*, 256(5062): 1443-1445, 1992

Gorziglia and Kapikian, *J. Virol.* 66: 4407-4412, 1992

Harris et al., *J Biol Chem* 285: 21092-102, 2010

Helseth et al., *J. Virol.* 64: 2416-2420, 1990

Huston et al., *Proc. Natl. Acad. Sci. USA* 85: 5879, 1988

Johnson et al., *J. Virol.* 66: 2952-2965, 1992

Joklik ed., *Virology*, 3rd Edition, 1988

Jones et al., *Nature* 321: 522-525, 1986

Kabat et al., *Sequences of Proteins of Immunological Interest*, 5th Ed, US Department of Health and Human Services, PHS, NIH, NIH Publication No. 91-3242, 1991

Keck et al., *J Virol* 78: 9224-32, 2004

Keck et al., *J Virol* 79: 13199-208, 2005

Kielian and Rey, *Nat Rev Microbiol* 4: 67-76, 2006

Kohler and Milstein, *Nature* 256: 495-499, 1975

Kortt et al., *Protein Engineering* 10: 423, 1997

Kozak and Shatkin, *Methods Enzymol,* 60: 360-375, 1979

Kozak, *Biochimie.,* 76(9): 815-21, 1994

Kozak, *J Cell Biol,* 108(2): 229-241, 1989

Kozak, *Mamm Genome,* 7(8): 563-74, 1996

Krey et al., *PLoS Pathog* 6(2): e1000762, 2010

Kunkel et al., *Methods in Enzymol.*, 154: 367-382, 1987

Kunkel, *Proc. Natl. Acad. Sci. USA,* 82: 488-492, 1985

Larrick et al., *Bio/Technology* 7: 934, 1989

Liu et al., *Proc. Natl. Acad. Sci. USA* 84: 3439, 1987

Madzak et al., *J. Gen. Virol.* 73: 1533-1536, 1992

Mann and Baltimore, *J. Virol.* 54: 401-407, 1985

Margolskee, *Curr. Top., Microbiol. Immunol.* 158: 67-95, 1992

Marks et al., *J. Mol. Biol.* 222: 581-597, 1991

McCaffrey et al., *J Virol* 81: 9584-90, 2007

Miller et al., *J. Virol.* 62: 4337-4345, 1988

Miller et al., *Mol. Cell. Biol.* 5: 431-437, 1985
Miller, *Curr. Top. Microbiol. Immunol.* 158: 1-24, 1992
Morrison et al., *Proc. Nat. Acad. Sci.* 81: 6851, 1984
Moss, *Curr. Top. Microbiol. Immunol.* 158: 25-38, 1992
Moss, *Proc. Natl. Acad. Sci. USA* 93: 11341-11348, 1996
Muzyczka, *Curr. Top. Microbiol. Immunol.* 158: 97-129, 1992
Naldini et al., *Science* 272: 263-267, 1996
Newton and Graham eds., *PCR, Introduction to Biotechniques Series*, 2nd ed., Springer Verlag, 1997
Ohi et al., *Gene* 89: 279-282, 1990
Owsianka et al., *J Virol* 80: 8695-704, 2006
Padlan et al., *Mol. Immunol.* 28: 489-498, 1991
Page et al., *J. Virol.* 64: 5270-5276, 1990
Pedersen et al., *J. Mol. Biol.* 235: 959-973, 1994
Petropoulos et al., *J. Viol.* 66: 3391-3397, 1992
Presta, *Curr. Op. Struct. Biol.* 2: 593-596, 1992
Quantin et al., *Proc. Natl. Acad. Sci. USA* 89: 2581-2584, 1992
Ream et al., eds., *Molecular Biology Techniques: An Intensive Laboratory Course*, Academic Press, 1998
Reichmann et al., *Nature* 332: 323-329, 1988
Remington's Pharmaceutical Sciences, 18th Ed., Mack Publishing, Company, Easton, Pa., U.S.A., 1990
Roberge et al., *Science,* 269(5221): 202-204, 1995
Roccasecca et al., *J Virol* 77: 1856-67, 2003
Rose et al., *A Laboratory Course Manual*, Cold Spring Harbor Laboratory, Cold Spring Harbor, N.Y., 1990
Rosenfeld et al., *Cell* 68: 143-155, 1992
Russell and Hirata, *Nature Genetics* 18: 323-328, 1998
Sambrook et al., *Molecular Cloning: A Laboratory Manual*, Cold Spring Harbor Laboratory, Cold Spring Harbor, N.Y., Sections 13, 16 and 17, 1989
Schneider et al., *Nature Genetics* 18: 180-183, 1998
Sharp and Cowe, *Yeast,* 7: 657-678, 1991
Shimada et al., *J. Clin. Invest.* 88: 1043-1047, 1991
Sorge et al., *Mol. Cell. Biol.* 4: 1730-1737, 1984
Stratford-Perricaudet et al., *Hum. Gene Ther.* 1: 241-256, 1990
van Anken et al., *Mol Biol Cell* 19: 4298-309, 2008
Vieyres et al., *J Virol* 1810-10, 2011
Vieyres et al., *J Virol* 84(19): 10159-10168, 2010
Ward et al., *Nature* 334: 544, 1989
Watson et al., *Molecular Biology of the Gene, Fourth Edition*, Benjamin/Cummings, Menlo Park, Calif., 1987
Weir and Blackwell, eds., *Handbook of Experimental Immunology, Vols. I-IV*, Blackwell Scientific Publications, 1986
Whidby et al., *Journal of Virology* 83(21): 11078-11089, 2009
Wilkinson et al., *Nucleic Acids Res.* 20: 2233-2239, 1992
Winter and Harris, *TIPS* 14: 139, 1993
Wittig et al., *Nat Protoc* 1: 418-28, 2006
Zubay, *Biochemistry, third edition*, Wm.C. Brown Publishers, 1993

What is claimed is:

1. A composition, comprising a modified hepatitis C virus (HCV) Envelope 2 (E2) polypeptide including a modified receptor binding variant, comprising at least four mutated or disrupted cysteines selected from among C581, C585, C652, C677, C494, C486, C459, C452, C564, C597, C569 and C620, wherein the polypeptide forms substantially fewer multimers by intermolecular disulfide bonding relative to the HCV E2 polypeptide without cysteine modification, and substantially retains CD81 binding.

2. The composition of claim 1, wherein C486, C581 and C652 are mutated or disrupted.

3. The composition of claim 1, wherein C581, C585 and C652 are mutated or disrupted.

4. The composition of claim 1, wherein C452, C486, C581 and C652 are mutated or disrupted.

5. The composition of claim 1, wherein C569, C581, C585 and C652 are mutated or disrupted.

6. The composition of claim 1, wherein C452, C581, C585 and C652 are mutated or disrupted.

7. The composition of claim 1, wherein the polypeptide folds as at least 40%, or at least 45%, or at least 50%, or at least 55%, or at least 60%, or at least 65%, or at least 70% monomers.

8. The composition of claim 1, wherein the polypeptide folds as less than 70% multimers, or less than 65%, or less than 60%, or less than 55%, or less than 50%, or less than 45% or less than 40% multimers by intermolecular disulfide bonding relative to the HCV E2 polypeptide without cysteine modification.

9. The composition of claim 1, wherein the HCV E2 polypeptide is $E2_{661}$ or a receptor binding portion thereof.

10. The composition of claim 1, wherein the HCV E2 polypeptide further comprises a deletion in 1, 2, or 3 variable regions selected from among hypervariable region 2 (HVR2), HVR1 and intergenotypic variable region (IgVR).

11. The composition of claim 1, further comprising a physiologically or pharmaceutically acceptable carrier and/or diluent.

12. A method for the diagnosis or monitoring of HCV infection, or monitoring of an anti-HCV treatment protocol in a subject, comprising:
 contacting a sample from the subject with a composition of claim 1; and
 detecting an interaction between the sample and the composition.

13. A method for screening for binding agents that prevent host cell entry by hepatitis C virus, comprising:
 contacting a putative interacting compound with a composition of claim 1; and
 detecting an interaction between the putative interacting compound and the composition.

14. An isolated host cell or host cell culture, comprising the composition of claim 1.

15. A method of eliciting an immune response in a subject or patient, the method comprising administering to the subject a composition of claim 1 for a time and under conditions suitable to elicit an immune response.

16. A diagnostic kit or a solid substrate, comprising a composition of claim 1.

17. A method of producing a composition comprising at least 40%, or at least 45%, or at least 50%, or at least 55%, or at least 60%, or at least 65%, or at least 70% monomeric HCV E2 polypeptide, the method comprising:

expressing a modified HCV E2 polypeptide in a host cell; and isolating the expressed product, wherein the modified HCV E2 polypeptide includes a modified receptor binding variant comprising at least four mutated or disrupted cysteines selected from among C581, C585, C652, C677, C494, C486, C459, C452, C564, C597, C569 and C620.

18. The method of claim 17, wherein C486, C581 and C652 are mutated or disrupted.

19. The method of claim 17, wherein C581, C585 and C652 are mutated or disrupted.

20. The method of claim 17, wherein C452, C486, C581 and C652 are mutated or disrupted.

21. The method of claim 17, wherein C569, C581, C585 and C652 are mutated or disrupted.

22. The composition of claim 3, wherein C452, C581, C585 and C652 are mutated or disrupted.

23. The composition of claim 1, wherein C452, C486, C569, C581, C585 and C652 are mutated or disrupted.

24. The composition of claim 1, wherein C452, C486, C569, C581, C585, C597 and C652 are mutated or disrupted.

25. The method of claim 17, wherein C452, C486, C569, C581, C585 and C652 are mutated or disrupted.

26. The method of claim 17, wherein C452, C486, C569, C581, C585, C597 and C652 are mutated or disrupted.

* * * * *

UNITED STATES PATENT AND TRADEMARK OFFICE
CERTIFICATE OF CORRECTION

| | | |
|---|---|---|
| PATENT NO. | : 9,079,950 B2 | Page 1 of 1 |
| APPLICATION NO. | : 13/813929 | |
| DATED | : July 14, 2015 | |
| INVENTOR(S) | : Drummer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 73 days.

Signed and Sealed this
Nineteenth Day of January, 2016

Michelle K. Lee
*Director of the United States Patent and Trademark Office*